(12) United States Patent
Kim et al.

(10) Patent No.: US 7,723,376 B2
(45) Date of Patent: May 25, 2010

(54) 2-OXO-HETEROCYCLIC COMPOUNDS AND PHARMACEUTICAL COMPOSITIONS

(75) Inventors: Hwan Mook Kim, Daejeon (KR); Gyoon Hee Han, Gyeonggi-do (KR); Song Kyu Park, Daejeon (KR); Chang Woo Lee, Daejeon (KR); Sang Bae Han, Chungcheongbuk-do (KR); Ki Hoon Lee, Daejeon (KR); Yung Hee Kho, Gyeonggi-do (KR); Jin Hyuk Yang, Daejeon (KR); Bum Woo Park, Seoul (KR); Hyang Woo Lee, Gyeonggi-do (KR); Jeung Whan Han, Gyeonggi-do (KR); Dong Kyu Ryu, Daejeon (KR); Jin Ha Lee, Daejeon (KR); Tae Gyu Chun, Daejeon (KR); Yong Kee Kim, Gyeonggi-do (KR); Hee Yoon Lee, Daejeon (KR); Bong Yong Lee, Gyeonggi-do (KR); Jeom Yong Kim, Seoul (KR); Ji Duck Kim, Gyeonggi-do (KR); Kyunga Yu, Seoul (KR); Sun Young Kim, Seoul (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 653 days.

(21) Appl. No.: 10/564,653

(22) PCT Filed: Jul. 15, 2004

(86) PCT No.: PCT/KR2004/001764

§ 371 (c)(1),
(2), (4) Date: Jan. 14, 2006

(87) PCT Pub. No.: WO2005/004861

PCT Pub. Date: Jan. 20, 2005

(65) Prior Publication Data

US 2006/0173043 A1 Aug. 3, 2006

(30) Foreign Application Priority Data

| Jul. 15, 2003 | (KR) | 10-2003-0048153 |
| Jul. 15, 2003 | (KR) | 10-2003-0048154 |
| Jul. 7, 2004 | (KR) | 10-2004-0052713 |
| Jul. 7, 2004 | (KR) | 10-2004-0052714 |
| Jul. 7, 2004 | (KR) | 10-2004-0052715 |
| Jul. 7, 2004 | (KR) | 10-2004-0052716 |
| Jul. 7, 2004 | (KR) | 10-2004-0052718 |

(51) Int. Cl.
*A01N 43/36* (2006.01)
(52) U.S. Cl. .............. 514/423; 514/389; 514/183; 514/359; 514/408
(58) Field of Classification Search ............ 514/183
See application file for complete search history.

(56) References Cited

U.S. PATENT DOCUMENTS

| 5,712,300 A * | 1/1998 | Jacobsen ............ 514/389 |
| 5,981,490 A | 11/1999 | Baxter |
| 6,403,632 B1 | 6/2002 | Duan |
| 6,413,955 B1 | 7/2002 | Askew |
| 6,608,104 B2 | 8/2003 | Noe |
| 2003/0032625 A1 | 2/2003 | Jensen |
| 2007/0167486 A1 * | 7/2007 | Kho et al. ............ 514/317 |

FOREIGN PATENT DOCUMENTS

| GB | 1042640 A | 9/1966 |
| WO | 99/18074 A | 4/1999 |
| WO | 00/59285 A | 10/2000 |
| WO | 2004/101523 A | 11/2004 |

OTHER PUBLICATIONS

Duffy et al., 2005, Clinical chemistry, vol. 51, No. 3, pp. 494-503.*
Harold L. Newmark, Joanne R. Lupton, and Charles W. Young, Butyrate as a differentiating agent: pharmacokinetics, analogues and current status, Cancer Letters vol. 78, Issues 1-3 , Apr. 1, 1994, pp. 1-5.
Naoki Tsuji, Masaaki Kobayashi, Kazuo Nagashima, Yoshiharu Wakisaka and Kenzo Koizumi, A New Antifungal Antibiotic, Trichostation, Journal of Antibiotics, Oct. 30, 1975.
Victoria M. Richon, Stephane Emiliani, Eric Verdin, Yael Webb, Ronald Breslow, Richard A. Rifkind, and Paul A. Marks, A class of hybrid polar inducers of transformed cell differentiation inhibits histone deacetylases, PNAS 1998 95: 3003-3007.
Young Bae Kim, Kun-Hyung Lee, Kenji Sugita, Minoru Yoshida and Sueharu Horinouchi, Oxamflatin is a novel antitumor compound that inhibits mammalian histone deacetylase, Apr. 15, 1999, vol. 18, No. 15, pp. 2461-2470.
M Kijima, M Yoshida, K Sugita, S Horinouchi, and T Beppu, Trapoxin, an antitumor cyclic tetrapeptide, is an irreversible inhibitor of mammalian histone deacetylase, J. Biol. Chem., Oct. 1993; 268: 22429-22435.

(Continued)

*Primary Examiner*—Ardin Marschel
*Assistant Examiner*—Meghan Finn
(74) *Attorney, Agent, or Firm*—Kirk Hahn

(57) ABSTRACT

The present invention is related to novel use of 2-oxo-heterocyclic compounds having anticancer activity and the process for preparing them and a pharmaceutical composition comprising the same. The present invention provides a pharmaceutical composition for preventing and treating the cancer disease comprising lung cancer, bone cancer, pancreatic cancer, skin cancer, cancer of the head and neck, cutaneous or intraocular melanoma, uterine cancer, ovarian cancer, rectal cancer or cancer of the anal region, stomach cancer, colon cancer, breast cancer, gynecologic tumors, Hodgkin's disease, cancer of the esophagus, cancer of the small intestine, cancer of the endocrine system, sarcomas of soft tissues, cancer of the urethra, cancer of the penis, prostate cancer, chronic or acute leukemia, solid tumors of childhood, lymphocytic lymphonas, cancer of the bladder, cancer of the kidney or ureter, or neoplasms of the central nervous system, therefore, it can be used as the therapeutics for treating and preventing cancer diseases.

8 Claims, No Drawings

OTHER PUBLICATIONS

Hidenori Nakajima, Young Bae Kim, Hiroshi Terano, Minoru Yoshida, and Sueharu Horinouchi, FR901228, a Potent Antitumor Antibiotic, Is a Novel Histone Deacetylase Inhibitor, Experimental Cell Research 241, 126-133 (1998).

Sandra J. Darkin-Rattray, Anne M. Gurnett, Robert W. Myers, Paula M. Dulski, Tami M. Crumley, John J. Allocco, Christine Cannova, Peter T. Meinke, Steven L. Colletti, Maria A. Bednarek, Sheo B. Singh, Michael A. Goetz, Anne W. Dombrowski, Jon D. Polishook, and Dennis M. Schmatz, Apicidin: A novel antiprotozoal agent that inhibits parasite histone deacetylase, PNAS 1996 93: 13143-13147.

Akiko Saito, Takashi Yamashita, Yukiyasu Mariko, Yasuhito Nosaka, Katsutoshi Tsuchiya, Tomoyuki Ando, Tsuneji Suzuki, Takashi Tsuruo, and Osamu Nakanishi, A synthetic inhibitor of histone deacetylase, MS-27-275, with marked in vivo antitumor activity against human tumors, PNAS 1999 96: 4592-4597.

European Search Report, Sep. 30, 2009.

* cited by examiner

2-OXO-HETEROCYCLIC COMPOUNDS AND PHARMACEUTICAL COMPOSITIONS

This application is the U.S. National Phase under 35 U.S.C. §371 of International Application PCT/KR2004/001764, filed on Jul. 15, 2004, which claims priority to Korean Patent Application No. 10-2004-0052713 filed on Jul. 7, 2004; Korean Patent Application No. 10-2004-0052716, filed on Jul. 7, 2004; Korean Patent Application No. 10-2004-0052718, filed on Jul. 7, 2004; Korean Patent Application No. 10-2004-0052715, filed on Jul. 7, 2004; Korean Patent Application No. 10-2004-0052714, filed on Jul. 7, 2004; Korean Patent Application No. 10-2003-0048154, filed on Jul. 15, 2003; and Korean Patent Application No. 10-2003-0048153, filed on Jul. 15, 2003. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to novel use of 2-oxo-heterocyclic compounds having anticancer activity and the pharmaceutical compositions comprising the same.

BACKGROUND ART

Cancer is characterized that cell cluster called as tumor caused by abnormal and uncontrolled cell growth, is formed, permeated into neighboring tissue and severe to be transferred to other organ, which is called as neoplasia. Over than 20 million peoples per year are suffered with cancer in the world and among them 6 million people per year were died from the disease. The origin of cancer is classified into internal factor e.g., genetic factor, immunological factor etc and external factor e.g., various chemical substances, radioactive ray, virus etc. Cancer may occur when the balance between oncogene and tumor suppressor genes is collapsed by above explained factors.

Histone is a nuclear protein bound to nucleus DNA and reversible acetylation reaction of histones occurs at s-amino group of positively charged lysine tail with reversibility. Since the reaction relates to the formation of highly structure of chromatin, it is reported to be correlated with the regulation of the cell cycle and gene expression accompanied with non-histone proteins.

The balance of acetylated status is sustained with the regulation of two enzyme complexes, histone acetyltransferase (HAT) and histone deacetylase (HDAC), and the change of acetylation level is reported to be essential in the change of gene expression. Therefore, the acetylated state of histone can be regulated by compounds inhibiting HDAC activity, according to the structure, for example, (1) butyrate having short chain fatty acid structure (Newmark et al., *Cancer Lett.* 78, pp 1-5, 1994), (2) trichostatin A, suberoylanilide hydroxamic acid (SAHA) and oxamflatin having hydroxamic acid structure (Tsuji et al., *J. Antibiot.* (Tokyo) 29, pp 1-6, 1976; Richon et al., *Proc. Natl. Acad. Sci.* USA, 95, pp 3003-3007, 1998; Kim et al., *Oncogene* 18, pp 2461-2470, 1999), (3) cyclic tetrapeptide structure including the 2-amino-8-oxo-9, 10-epoxy-decanoyl (AOE); trapoxin A (Kijima et al., J. Biol. Chem. 268, 22429-22435, 1993), (4) cyclic tetrapeptide structure including the AOE; FR901228 and apicidin (Na-kjima et al., *Exp. Cell Res.* 241, pp 126-33, 1998; Darkin-Rattray et al., *Proc. Natl. Acad. Sci.* USA, 93, pp 13143-13147, 1996), (5) benzamide structure; MS-27-275 (Saito et al., *Proc. Natl. Acad. Sci. USA,* 96, pp 4592-4597, 1999).

It has been known that these compounds inhibit HDAC enzyme, induce hyper-acetylation of histone protein, cause to hyper-expression of a specific protein family such as tumor inhibiting factor and inhibit the growth of cancer cell resulting in cancer cell death. Accordingly, the compound inhibiting HDAC selectively can be developed to be a promising candidate drug inhibiting cancer cell and inducing to cell death.

However, there has been not reported or disclosed about novel oxopiperidine compound showing potent inhibiting activity of HDAC activity and anticancer activity in any of above cited literatures, the disclosures of which are incorporated herein by reference.

To investigate novel compound having oxopiperidine skeleton showing potent inhibiting activity of HDAC activity and anticancer activity, the inventors of present invention have intensively carried out in vitro experiment concerning the inhibition effect on the HDAC enzyme. As a result of the investigation, the inventors finally completed the present invention by confirming that the novel compound of the present invention inhibited HDAC enzyme and it can be useful as an anti-cancer agent.

SUMMARY OF THE INVENTION

The present invention also provides a use of novel 2-oxo-heterocyclic compound and the pharmacologically acceptable salt thereof for the preparation of pharmaceutical composition to treat and prevent cancer diseases.

The present invention provides a pharmaceutical composition comprising a novel 2-oxo-heterocyclic compound and the pharmacologically acceptable salt thereof as an active ingredient in an effective amount to treat and prevent cancer diseases.

DISCLOSURE OF THE INVENTION

Thus, the present invention provides a novel use of a compound represented by the following general formula (I), and the pharmaceutically acceptable salt or the isomer thereof for the preparation of pharmaceutical composition to treat and prevent cancer diseases:

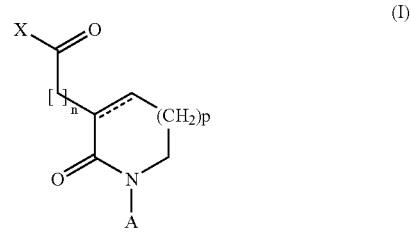

wherein

X is a hydroxyl group, —NHOH, —NHOCH$_2$Ph,

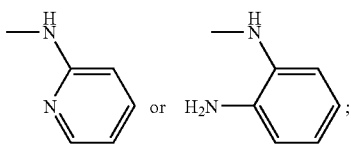

A is an hydrogen, A1 group or

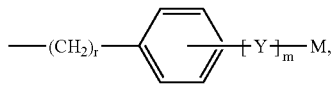
(A2)

A1 is a lower alkyl, lower alkenyl, lower alkynyl, lower allyl group having C1 to C5 carbon atoms, a heterocyclic group or aromatic aryl group, preferably, the group selected from thiophenyl group, naphtyl group, pyrrolyl group, furyl group and biphenyl group, wherein Y is a lower alkyl group, lower alkoxy group, nitro, halogen, amine, acetamide, carbonamide or sulfonamide group, M is a lower alkyl group or phenyl group substituted with R', of which R' is a hydrogen, lower alkyl or lower alkoxy group, m and r is independently an integer of 1 to 5 respectively in A2 residue;

p is an integer of 0, 1 or 2;
n is an integer of 1 to 5;
dotted line (-----) means single bond or double bond.

In preferred embodiment, the present invention also provides a use of the compounds represented by following general formula (II), the pharmaceutically acceptable salt or the isomer thereof for the preparation of pharmaceutical composition to treat and prevent cancer diseases:

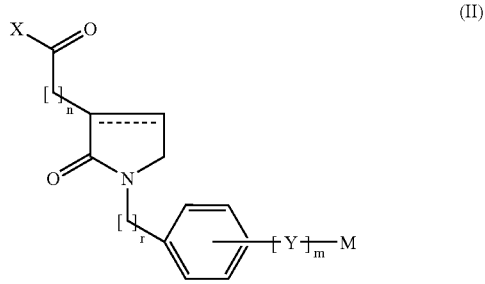
(II)

wherein
X is a hydroxyl group, —NHOH, —NHOCH$_2$Ph,

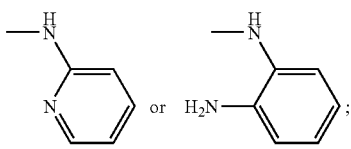

Y is a lower alkyl group, lower alkoxy group, nitro, halogen, amine, acetamide, carbonamide or sulfonamide group;
M is a lower alkyl group or phenyl group substituted with R', of which R' is a hydrogen, lower alkyl or lower alkoxy group;
m and r is independently an integer of 1 to 5 respectively;
n is an integer of 1 to 5;
dotted line ((-----)) means single bond or double bond.

The preferred compound of general formula (II) is one selected from the group consisting of;

3-[1-(2,4-Dimethoxybenzyl)-2-oxo-2,5-dihydro-1H-pyrrol-3-yl]-N-hydroxypropionamide,
3-(1-benzyl-2-oxo-2,5-dihydro-1H-pyrrol-3-yl)-N-hydroxypropionamide,
N-hydroxy-3-(2-oxo-1-phenethyl-2,5-dihydro-1H-pyrrol-3-yl)-propionamide,
N-hydroxy-3-[2-oxo-1-(3-phenyl-propyl)-2,5-dihydro-1H-pyrrol-3-yl]-propionamide,
N-hydroxy-3-[2-oxo-1-(4-phenyl-butyl)-2,5-dihydro-1H-pyrrol-3-yl]-propionamide,
N-hydroxy-3-[1-(2-methyl-benzyl)-2-oxo-2,5-dihydro-1H-pyrrol-3-yl]-propionamide,
N-hydroxy-3-[1-(3-methyl-benzyl)-2-oxo-2,5-dihydro-1H-pyrrol-3-yl]-propionamide,
N-hydroxy-3-[1-(4-methyl-benzyl)-2-oxo-2,5-dihydro-1H-pyrrol-3-yl]-propionamide,
N-hydroxy-3-[1-(2-methoxy-benzyl)-2-oxo-2,5-dihydro-1H-pyrrol-3-yl]-propionamide,
N-hydroxy-3-[1-(3-methoxy-benzyl)-2-oxo-2,5-dihydro-1H-pyrrol-3-yl]-propionamide,
N-hydroxy-3-[1-(4-methoxy-benzyl)-2-oxo-2,5-dihydro-1H-pyrrol-3-yl]-propionamide,
3-[1-(4-bromo-benzyl)-2-oxo-2,5-dihydro-1H-pyrrol-3-yl]-N-hydroxy-propionamide,
3-[1-(4-chloro-benzyl)-2-oxo-2,5-dihydro-1H-pyrrol-3-yl]-N-hydroxy-propionamide,
3-[1-(4-benzyloxy-benzyl)-2-oxo-2,5-dihydro-1H-pyrrol-3-yl]-N-hydroxy-propionamide,
N-hydroxy-3-[1-(4-nitro-benzyl)-2-oxo-2,5-dihydro-1H-pyrrol-3-yl]-propionamide,
3-[1-(2,4-dimethoxy-benzyl)-2-oxo-2,5-dihydro-1H-pyrrol-3-yl]-propionic acid,
3-(1-benzyl-2-oxo-2,5-dihydro-1H-pyrrol-3-yl)-propionic acid,
N-{4-[3-(2-hydroxycarbamoyl-ethyl)-2-oxo-2,5-dihydro-pyrrole-1-yl-methyl]-phenyl}-benzamide,
N-hydroxy-3-{2-oxo-1-[4-(toluene-4-sulfonylamino)-benzyl]-2,5-dihydro-1H-pyrrol-3-yl}-propionamide,
2-(1-benzyl-2-oxo-2,5-dihydro-1H-pyrrol-3-yl)-N-hydroxy-acetamide,
2-[1-(2,4-dimethoxy-benzyl)-2-oxo-2,5-dihydro-1H-pyrrol-3-yl]-N-hydroxy-acetamide,
N-hydroxy-2-(2-oxo-1-phenethyl-2,5-dihydro-1H-pyrrol-3-yl)-acetamide,
N-hydroxy-2-[2-oxo-1-(4-phenyl-butyl)-2,5-dihydro-1H-pyrrol-3-yl]-acetamide,
2-[1-(4-benzyloxy-benzyl)-2-oxo-2,5-dihydro-1H-pyrrol-3-yl]-N-hydroxy-acetamide,
2-(1-benzyl-2-oxo-pyrrolidin-3-yl)-N-hydroxy-acetamide,
2-[1-(2,4-dimethoxy-benzyl)-2-oxo-pyrrolidin-3-yl]-N-hydroxy-acetamide,
N-hydroxy-2-(2-oxo-1-phenethyl-pyrrolidin-3-yl)-acetamide,
3-{1-[2-(2-fluoro-phenyl)-ethyl]-2-oxo-2,5-dihydro-1H-pyrrol-3-yl}-N-hydroxy-propionamide,
3-{1-[2-(3-fluoro-phenyl)-ethyl]-2-oxo-2,5-dihydro-1H-pyrrol-3-yl}-N-hydroxy-propionamide,
3-{1-[2-(4-fluoro-phenyl)-ethyl]-2-oxo-2,5-dihydro-1H-pyrrol-3-yl}-N-hydroxy-propionamide,
N-hydroxy-3-{1-[2-(2-nitro-phenyl)-ethyl]-2-oxo-2,5-dihydro-1H-pyrrol-3-yl}-propionamide,
N-hydroxy-3-{1-[2-(3-nitro-phenyl)-ethyl]-2-oxo-2,5-dihydro-1H-pyrrol-3-yl}-propionamide, N-hydroxy-3-{1-[2-(4-nitro-phenyl)-ethyl]-2-oxo-2,5-dihydro-1H-pyrrol-3-yl}-propionamide,
3-{1-[2-(2-bromo-phenyl)-ethyl]-2-oxo-2,5-dihydro-1H-pyrrol-3-yl}-N-hydroxy-propionamide,
3-{1-[2-(4-bromo-phenyl)-ethyl]-2-oxo-2,5-dihydro-1H-pyrrol-3-yl}-N-hydroxy-propionamide,
N-hydroxy-3-{1-[2-(2-methoxy-phenyl)-ethyl]-2-oxo-2,5-dihydro-1H-pyrrol-3-yl}-propionamide,
N-hydroxy-3-{1-[2-(3-methoxy-phenyl)-ethyl]-2-oxo-2,5-dihydro-1H-pyrrol-3-yl}-propionamide,
N-hydroxy-3-{1-[2-(4-methoxy-phenyl)-ethyl]-2-oxo-2,5-dihydro-1H-pyrrol-3-yl}-propionamide,
N-hydroxy-3-[2-oxo-1-(2-p-tolyl-ethyl)-2,5-dihydro-1H-pyrrol-3-yl]-propionamide,
N-hydroxy-3-{1-[3-(4-methoxy-phenyl)-propyl]-2-oxo-2,5-dihydro-1H-pyrrol-3-yl}-propionamide,
N-hydroxy-3-[2-oxo-1-(3-o-tolyl-propyl)-2,5-dihydro-1H-pyrrol-3-yl]-propionamide,
N-hydroxy-3-[2-oxo-1-(3-m-tolyl-propyl)-2,5-dihydro-1H-pyrrol-3-yl]-propionamide,
N-hydroxy-3-{1-[3-(4-isopropyl-phenyl)-propyl]-2-oxo-2,5-dihydro-1H-pyrrol-3-yl}-propionamide,
3-{1-[3-(4-bromo-phenyl)-propyl]-2-oxo-2,5-dihydro-1H-pyrrol-3-yl}-N-hydroxy-propionamide,
3-{1-[3-(4-chloro-phenyl)-propyl]-2-oxo-2,5-dihydro-1H-pyrrol-3-yl}-N-hydroxy-propionamide,
N-hydroxy-3-{1-[3-(4-methoxy-phenyl)-propyl]-2-oxo-2,5-dihydro-1H-pyrrol-3-yl}-propionamide,
N-hydroxy-3-{1-[3-(2-methoxy-phenyl)-propyl]-2-oxo-2,5-dihydro-1H-pyrrol-3-yl}-propionamide,
N-hydroxy-3-[1-[3-(3-methoxy-phenyl)-propyl]-2-oxo-2,5-dihydro-1H-pyrrol-3-yl]-propionamide.

In preferred embodiment, the present invention also provides a use of the compounds represented by following general formula (III), the pharmaceutically acceptable salt or the isomer thereof for the preparation of pharmaceutical composition to treat and prevent cancer diseases:

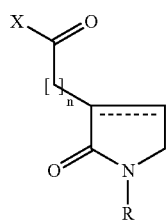

(III)

wherein
X is a hydroxyl group, —NHOH, —NHOCH$_2$Ph

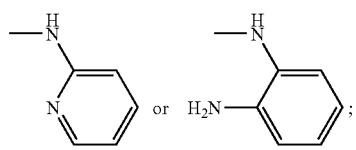

R is a lower alkyl, lower alkenyl, lower alkynyl, lower allyl group having C1 to C5 carbon atoms, a heterocyclic group or aromatic aryl group, preferably, the group selected from thiophenyl group, naphtyl group, pyrrolyl group, furyl group and biphenyl group;
n is an integer of 1 to 5;
dotted line ((-----)) means single bond or double bond.

The preferred compound of general formula (III) is one selected from the group consisting of;
N-hydroxy-3-(1-naphthalene-2-ylmethyl-2-oxo-2,5-dihydro-1H-pyrrol-3-yl)-propionamide,
N-hydroxy-3-(1-methyl-2-oxo-2,5-dihydro-1H-pyrrol-3-yl)-propionamide,
3-(1-allyl-2-oxo-2,5-dihydro-1H-pyrrol-3-yl)-N-hydroxy-propionamide,
N-hydroxy-3-[1-(2-naphthalene-1-yl-ethyl)-2-oxo-2,5-dihydro-1H-pyrrol-3-yl]-propionamide,
N-hydroxy-3-[1-(2-naphthalene-2-yl-ethyl)-2-oxo-2,5-dihydro-1H-pyrrol-3-yl]-propionamide,
N-hydroxy-3-[2-oxo-1-(2-thiophen-2-yl-ethyl)-2,5-dihydro-1H-pyrrol-3-yl]-propionamide,
3-[1-(3-biphenyl-4-yl-propyl)-2-oxo-2,5-dihydro-1H-pyrrol-3-yl]-N-hydroxy-propionamide,
N-hydroxy-3-[1-(3-naphthalene-2-yl-propyl)-2-oxo-2,5-dihydro-1H-pyrrol-3-yl]-propionamide.

In preferred embodiment, the present invention also provides a use of the compounds represented by following general formula (IV), the pharmaceutically acceptable salt or the isomer thereof for the preparation of pharmaceutical composition to treat and prevent cancer diseases:

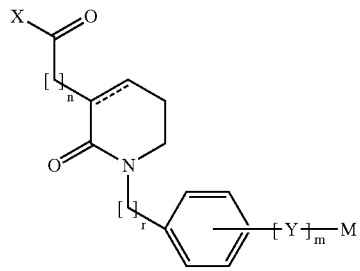

(IV)

wherein
X is a hydroxyl group, —NHOH, —NHOCH$_2$Ph,

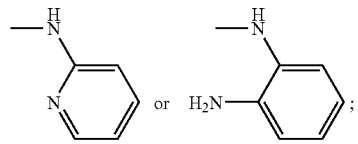

Y is a lower alkyl group, lower alkoxy group, nitro, halogen, amine, acetamide, carbonamide or sulfonamide group;
M is a lower alkyl group or phenyl group substituted with R', of which R' is a hydrogen, lower alkyl or lower alkoxy group;
m and r is independently an integer of 1 to 5 respectively;
n is an integer of 1 to 5;
dotted line ((-----)) means single bond or double bond.
The preferred compound of general formula (IV) is one selected from the group consisting of;
3-[1-(2,4-Dimethoxybenzyl)-2-oxo-1,2,5,6-tetrahydropyridin-3-yl]-N-hydroxypropionamide,
N-hydroxy-3-(1-benzyl-2-oxo-1,2,5,6-tetrahydro-pyridin-3-yl)-propionic acid,
N-hydroxy-3-[1-(4-nitro-benzyl)-2-oxo-1,2,5,6-tetrahydro-pyridin-3-yl)-propionamide,
3-(1-benzyl-2-oxo-1,2,5,6-tetrahydro-pyridin-3-yl)-N-hydroxy propionamide, N-hydroxy-3-[2-oxo-1-(4-phenyl-propyl)-1,2,5,6-tetrahydro-pyridin-3-yl]-propionamide,
N-hydroxy-3-[2-oxo-1-(4-phenyl-butyl)-1,2,5,6-tetrahydro-pyridin-3-yl]-propionamide,
N-hydroxy-3-(2-oxo-1-phenethyl-1,2,5,6-tetrahydro-pyridin-3-yl)-propionamide,
3-[1-(2,4-dimethoxybenzyl)-2-oxo-1,2,5,6-tetrahydro-pyridin-3-yl)-propionic acid,
3-(1-benzyl-2-oxo-1,2,5,6-tetrahydro-pyridin-3-yl)-propionic acid,
3-[1-(4-nitro-benzyl)-2-oxo-1,2,5,6-tetrahydro-pyridin-3-yl]-propionic acid,
3-[2-oxo-1-(4-phenyl-propyl)-1,2,5,6-tetrahydro-pyridin-3-yl)-propionic acid,
3-[2-oxo-1-(4-phenyl-butyl)-1,2,5,6-tetrahydro-pyridin-3-yl)-propionic acid,
3-(2-oxo-1-phenethyl-1,2,5,6-tetrahydro-pyridin-3-yl)-propionic acid,
3-(1-benzyl-2-oxo-1,2,5,6-tetrahydro-pyridin-3-yl)-N-pyridin-2-yl-propionamide,
N-(2-amino-phenyl)-3-(1-benzyl-2-oxo-1,2,5,6-tetrahydro-pyridin-3-yl)-propionamide,
N-(2-amino-phenyl)-3-[1-(2-methyl-benzyl)-2-oxo-1,2,5,6-tetrahydro-pyridin-3-yl)-propionamide,
N-(2-amino-phenyl)-3-[1-(2-methyl-benzyl)-2-oxo-1,2,5,6-tetrahydro-pyridin-3-yl)-propionamide,
N-benzyloxy-3-(2-oxo-1-phenethyl-1,2,5,6-tetrahydro-pyridin-3-yl)-propionamide,
3-[1-(4-acetylamino-benzyl)-2-oxo-1,2,5,6-tetrahydro-pyridin-3-yl)-N-hydroxy-propionamide,
N-4-[5-(2-hydroxycarbamoyl-ethyl)-6-oxo-3,6-dihydro-2-pyridin-1-yl-methyl]-phenyl-benzamide,
N-hydroxy-3-[1-(4-dimethylsulfonylamino-benzyl)-2-oxo-1,2,5,6-tetrahydro-pyridin-3-yl]-propionamide,
N-hydroxy-3-2-oxo-1-[4-(toluene-4-sulfonylamino)-benzyl-1,2,5,6-tetrahydro-pyridin-3-yl]-propionamide,
3-[1-(4-acetylamino-benzyl)-2-oxo-1,2,5,6-tetrahydro-pyridin-3-yl]-propionic acid,
3-[1-(4-benzoylamino-benzyl)-2-oxo-1,2,5,6-tetrahydro-pyridin-3-yl]-propionic acid,
3-2-oxo-1-[4-(toluene-4-sulfonylamino)-benzyl]-2-oxo-1,2,5,6-tetrahydro-pyridin-3-yl]-propionic acid,
N-hydroxy-3-(2-oxo-1-phenethyl-piperidine-3-yl)-propionamide,
2-[1-(2,4-dimethoxy-benzyl)-2-oxo-1,2,5,6-tetrahydro-pyridin-3-yl]-N-hydroxy-acetamide,
2-(1-benzyl-2-oxo-1,2,5,6-tetrahydro-pyridin-3-yl)-N-hydroxy-acetamide,
N-hydroxy-2-[1-(4-nitro-benzyl)-2-oxo-1,2,5,6-tetrahydro-pyridin-3-yl]-N-hydroxy-acetamide,
N-hydroxy-2-[2-oxo-1-(3-phenyl-propyl)-1,2,5,6-tetrahydro-pyridin-3-yl]-N-hydroxy-acetamide,
N-hydroxy-2-[2-oxo-1-(4-phenyl-butyl)-1,2,5,6-tetrahydro-pyridin-3-yl]-N-hydroxy-acetamide,
[1-(2,4-dimethoxy-benzyl)-2-oxo-1,2,5,6-tetrahydro-pyridin-3-yl]-acetic acid,
(1-benzyl-2-oxo-1,2,5,6-tetrahydro-pyridin-3-yl)-acetic acid,
(2-oxo-1-phenethyl-1,2,5,6-tetrahydro-pyridin-3-yl)-acetic acid,
[2-oxo-1-(3-phenyl-propyl)-1,2,5,6-tetrahydro-pyridin-3-yl)-acetic acid,
[2-oxo-1-(4-phenyl-butyl)-1,2,5,6-tetrahydro-pyridin-3-yl]-acetic acid,
2-[1-(2,4-dimethoxy-benzyl)-2-oxo-piperidine-3-yl]-N-hydroxy-acetamide,
(2-oxo-1-phenethyl-piperidine-3-yl)-acetic acid,
[2-oxo-1-(3-phenyl-propyl)-piperidine-3-yl]-acetic acid,
4-[1-(4-methoxy-benzyl)-2-oxo-1,2,5,6-tetrahydro-pyridin-3-yl]-N-hydroxy-butylamide,
4-(1-phenethyl-2-oxo-1,2,5,6-tetrahydro-pyridin-3-yl)-N-hydroxy-butylamide,
N-hydroxy-4-[2-oxo-1-(3-phenyl-propyl)-1,2,5,6-tetrahydro-pyridin-3-yl]-butylamide,
N-hydroxy-4-[2-oxo-1-(3-phenyl-butyl)-1,2,5,6-tetrahydro-pyridin-3-yl]-butylamide.

In preferred embodiment, the present invention also provides a use of the compounds represented by following general formula (V), the pharmaceutically acceptable salt or the isomer thereof for the preparation of pharmaceutical composition to treat and prevent cancer diseases:

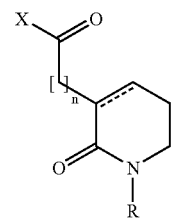

(V)

wherein
X is a hydroxyl group, —NHOH, —NHOCH$_2$Ph,

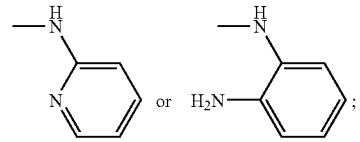

R is a lower alkyl, lower alkenyl, lower alkynyl, lower allyl group having C1 to C5 carbon atoms, a heterocyclic group or aromatic aryl group, preferably, the group selected from thiophenyl group, naphtyl group, pyrrolyl group, furyl group and biphenyl group;
n is an integer of 1 to 5;
dotted line ((-----)) means single bond or double bond.

The preferred compound of general formula (V) is one selected from the group consisting of;
3-(2-oxo-1,2,5,6-tetrahydro-pyridin-3-yl)-propionic acid,
N-Benzyloxy-3-(2-oxo-1,2,5,6-tetrahydro-pyridin-3-yl)-propionamide,
3-(1-Allyl-2-oxo-1,2,5,6-tetrahydro-pyridin-3-yl)-N-hydroxy-propionamide,
N-hydroxy-3-(1-methyl-2-oxo-1,2,5,6-tetrahydro-pyridin-3-yl)-propionamide,
N-hydroxy-3-(1-(naphthalene-2-yl-methyl)-2-oxo-1,2,5,6-tetrahydro-pyridin-3-yl)-propionamide,
N-hydroxy-3-[2-oxo-1-(2-thiophen-2-yl-ethyl)-1,2,5,6-tetrahydro-pyridin-3-yl]-propionamide.

In preferred embodiment, the present invention also provides the compounds represented by following general formula (VI), the pharmaceutically acceptable salt or the isomer thereof for the preparation of pharmaceutical composition to treat and prevent cancer diseases and the use thereof:

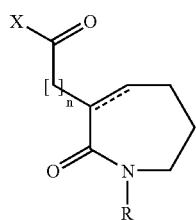

wherein
X is a hydroxyl group, —NHOH, —NHOCH₂Ph,

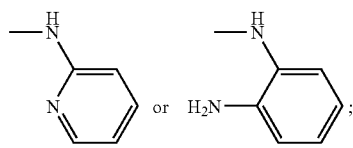

R is independently hydrogen atom, lower alkyl, lower alkenyl, lower alkynyl, lower allyl group having C1 to C4 carbon atoms substituted with a phenyl group which can be substituted with halogen atom or lower alkyl group;
n is an integer of 1 to 5;
dotted line ((-----)) means single bond or double bond.
The preferred compound of general formula (VI) is one selected from the group consisting of;
N-3-(1-benzyl-2-oxo-2,5,6,7-tetrahydro-1H-azepin-3-yl)-N-hydroxy-propionamide,
N-hydroxy-3-[2-oxo-1-(3-phenyl-ethyl)-2,5,6,7-tetrahydro-1H-azepin-3-yl]-propionamide,
N-hydroxy-3-[2-oxo-1-(3-phenyl-propyl)-2,5,6,7-tetrahydro-1H-azepin-3-yl]-propionamide,
N-hydroxy-3-[2-oxo-1-(3-phenyl-butyl)-2,5,6,7-tetrahydro-1H-azepin-3-yl]-propionamide.

It is another object of the present invention to provide the pharmaceutical composition comprising an efficient amount of the compound represented by general formula (I) to (VI) or the pharmaceutically acceptable salt thereof as an active ingredient in amount effective to prevent or treat cancer diseases together with pharmaceutically acceptable carriers or diluents.

The inventive compounds represented by general formula (I) to (VI) can be transformed into their pharmaceutically acceptable salt and solvates by the conventional method well known in the art. For the salts, acid-addition salt thereof formed by a pharmaceutically acceptable free acid thereof is useful and can be prepared by the conventional method. For example, after dissolving the compound in the excess amount of acid solution, the salts are precipitated by the water-miscible organic solvent such as methanol, ethanol, acetone or acetonitrile to prepare acid addition salt thereof and further the mixture of equivalent amount of compound and diluted acid with water or alcohol such as glycol monomethylether, can be heated and subsequently dried by evaporation or filtrated under reduced pressure to obtain dried salt form thereof. As a free acid of above-described method, organic acid or inorganic acid can be used. For example, organic acid such as methansulfonic acid, p-toluensulfonic acid, acetic acid, trifluoroacetic acid, citric acid, maleic acid, succinic acid, oxalic acid, benzoic acid, lactic acid, glycolic acid, gluconic acid, galacturonic acid, glutamic acid, glutaric acid, glucuronic acid, aspartic acid, ascorbic acid, carbonylic acid, vanillic acid, hydroiodic acid and the like, and inorganic acid such as hydrochloric acid, phosphoric acid, sulfuric acid, nitric acid, tartaric acid and the like can be used herein.

Further, the pharmaceutically acceptable metal salt form of inventive compounds may be prepared by using base. The alkali metal or alkali-earth metal salt thereof can be prepared by the conventional method, for example, after dissolving the compound in the excess amount of alkali metal hydroxide or alkali-earth metal hydroxide solution, the insoluble salts are filtered and remaining filtrate is subjected to evaporation and drying to obtain the metal salt thereof. As a metal salt of the present invention, sodium, potassium or calcium salt are pharmaceutically suitable and the corresponding silver salt can be prepared by reacting alkali metal salt or alkali-earth metal salt with suitable silver salt such as silver nitrate.

The pharmaceutically acceptable salt of the compound represented by general formula (I) to (VI) comprise all the acidic or basic salt which may be present at the compounds, if it does not indicated specifically herein. For example, the pharmaceutically acceptable salt of the present invention comprise the salt of hydroxyl group such as the sodium, calcium and potassium salt thereof; the salt of amino group such as the hydrogen bromide salt, sulfuric acid salt, hydrogen sulfuric acid salt, phosphate salt, hydrogen phosphate salt, dihydrophosphate salt, acetate salt, succinate salt, citrate salt, tartarate salt, lactate salt, mandelate salt, methanesulfonate (mesylate) salt and p-toluenesulfonate (tosylate) salt etc, which can be prepared by the conventional method well known in the art.

There may exist in the form of optically different diastereomers since the compounds represented by general formula (I) to (VI) have unsymmetrical centers, accordingly, the compounds of the present invention comprise all the optically active isomers, R or S stereoisomers and the mixtures thereof. Present invention also comprises all the uses of racemic mixture, more than one optically active isomer or the mixtures thereof as well as all the preparation or isolation method of the diastereomer well known in the art.

The compounds of the invention of formula (I) to (VI) may be chemically synthesized by the methods which will be explained by following reaction schemes hereinafter, which are merely exemplary and in no way limit the invention. The reaction schemes show the steps for preparing the representative compounds of the present invention, and the other compounds also may be produced by following the steps with appropriate modifications of reagents and starting materials, which are envisaged by those skilled in the art.

General Synthetic Procedures

Scheme 1

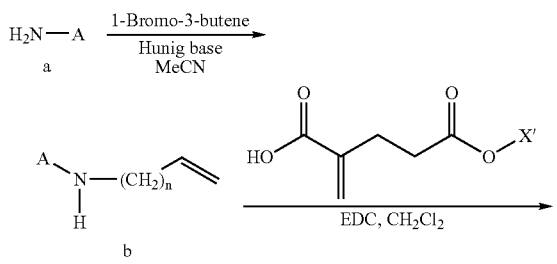

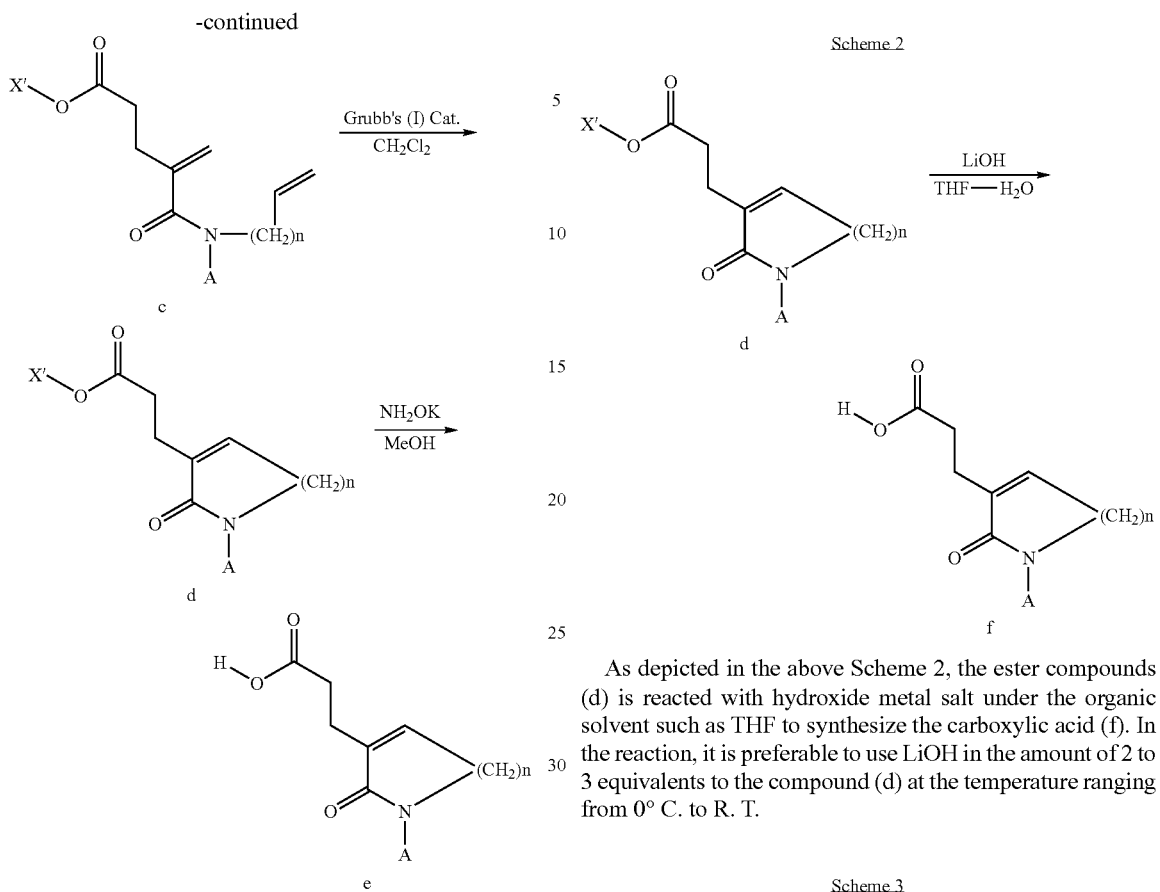

As depicted in above Scheme 1, the scheme explains the process for preparing hydroxamine compound (e) consisting of 4 steps;

At 1$^{st}$ step, compound (a) is reacted with 1-bromo-3-butene under organic solvent in the presence of Hunig base to synthesize compound (b). In the step, an organic solvent such as acetonitrile, dichloromethane etc are preferable and diethylisopropylamine can be used as a Hunig base in the amount of 2 to 3 equivalents to the compound (a). It is preferable the reaction is performed at the temperature ranging from 0° C. to R. T.

At 2$^{nd}$ step, the compound (b) obtained in step 1 is reacted with mono acid in the presence of 1-[3-(dimethylamino)propyl]-3-ethylcarbodiimide (EDC) under an organic solvent to synthesize the compound (c). In the step, an organic solvent such as methylenechloride, THF etc are preferable and a mono acid such as 2-methylene-pentandionic acid-5-methyl ester in the amount of 1 to 1.2 equivalents to the compound (b) is preferable. It is preferable the reaction is performed at the temperature ranging from 0° C. to R. T.

At 3$^{rd}$ step, the compound (c) obtained in step 2 is converted into the compound (d) in the presence of Grubb's (I) catalyst such as Ruthenium catalyst under organic solvent. In the step, it is preferable to use the catalyst in the amount of 0.02 to 0.1 equivalents to the compound (c) at the temperature ranging from 0° C. to R. T.

At 4$^{th}$ step, the compound (d) obtained in step 3 is reacted with amine salt to synthesize hydroxamide compound (e) in case that X is NHOH in general formula I compounds. In the step, it is preferable to use potassium hydroxamide (KONH$_2$) in the amount of 2 to 3 equivalents to the compound (d) at the temperature ranging from 0° C. to R. T.

As depicted in the above Scheme 2, the ester compounds (d) is reacted with hydroxide metal salt under the organic solvent such as THF to synthesize the carboxylic acid (f). In the reaction, it is preferable to use LiOH in the amount of 2 to 3 equivalents to the compound (d) at the temperature ranging from 0° C. to R. T.

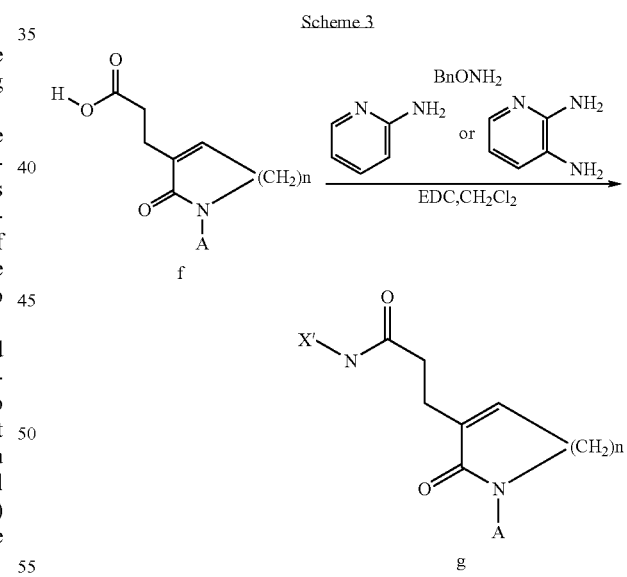

As depicted in the above Scheme 3, the carboxylic acid compound (f) obtained in Scheme 2 is reacted with benzyloxyamine (BnONH$_2$), pyridylamine or diaminobenzene in the presence of 1-[3-(dimethylamino)propyl]-3-ethylcarbodiimide (EDC) under organic solvent to synthesize the amide compounds of which X is benzyloxyamine (BnONH$_2$), pyridylamine or diaminobenzene group. In the reaction, it is preferable to use benzyloxyamine (BnONH$_2$), pyridylamine or diaminobenzene in the amount of 1 to 1.5 equivalents to the compound (f) at the temperature ranging from 0° C. to R. T.

Scheme 4

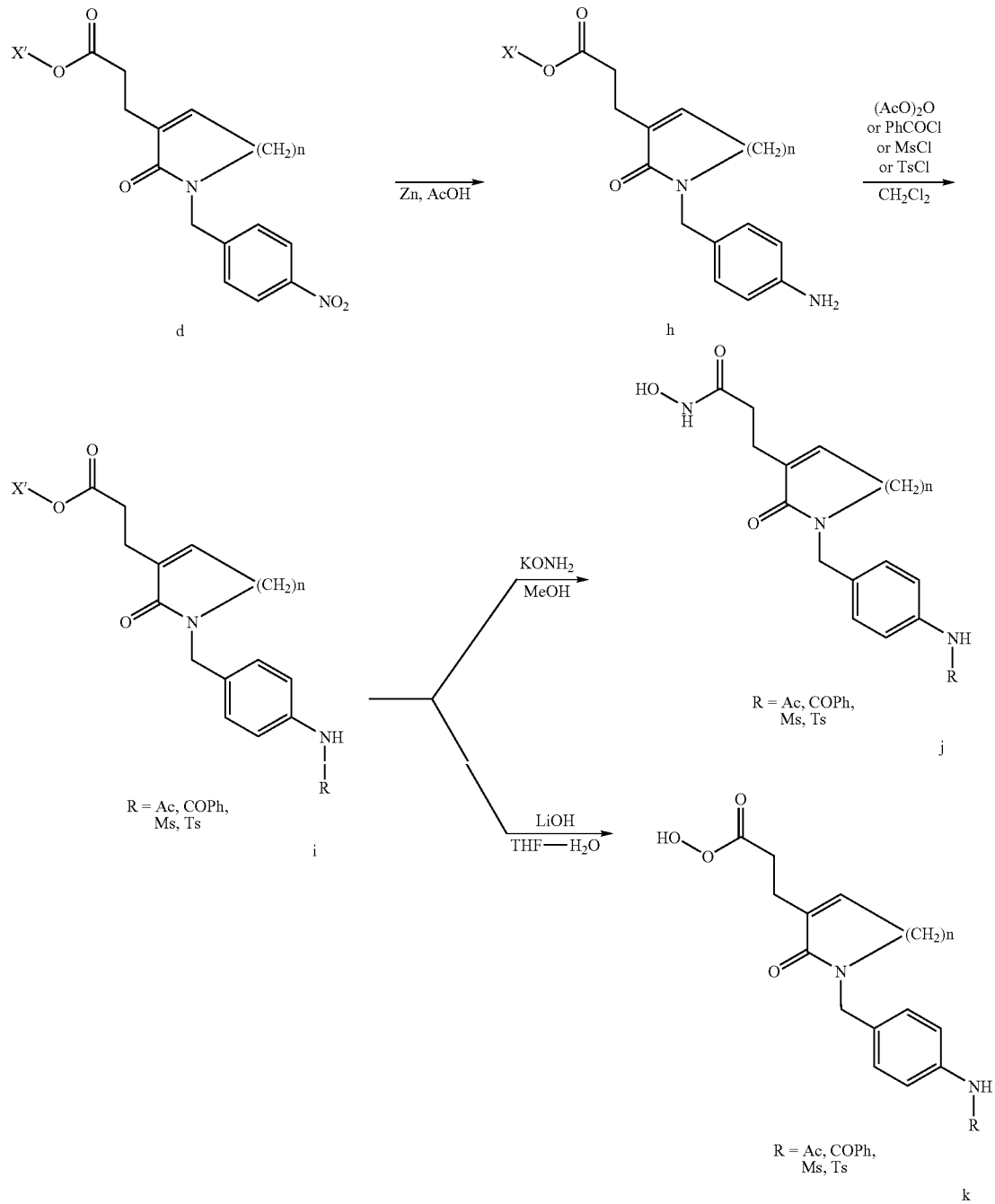

As shown in the above Scheme 4, the amide compound (j) and carboxylic acid compound (k) are prepared by following procedure from the ester compounds (d):

At 1$^{st}$ step, the compound (d) prepared from Scheme 2 is reacted with zinc under organic solvent to synthesize the compound (h). In the step, it is preferable to use the zinc in the amount of 2 to 5 equivalents of the compound (h).

At 2$^{nd}$ step, the compound (h) obtained in step 1 is reacted with (AcO)$_2$O, PhCOCl, MsCl or TsCL to synthesize the compound (i). In the reaction, it is preferable to use (AcO)$_2$O, PhCOCl, MsCl or TsCL in the amount of 1 to 3 equivalents to the compound (h).

At 3$^{rd}$ step, the compound (i) obtained in step 2 is reacted with amine salt under the organic solvent such as methanol to produce the hydroxamide compound (j), i.e., the general formula I compound wherein X is NHOH where the amine salt is preferably used in the amount of 2 to 3 equivalents to the compound (i), or with hydroxide metal salt such as LiOH under the organic solvent such as THF to produce the carboxylic acid compound (k), i.e., the general formula I compound wherein X is OH where the metal salt is preferably used in the amount of 2 to 3 equivalents to the compound (i).

Scheme 5

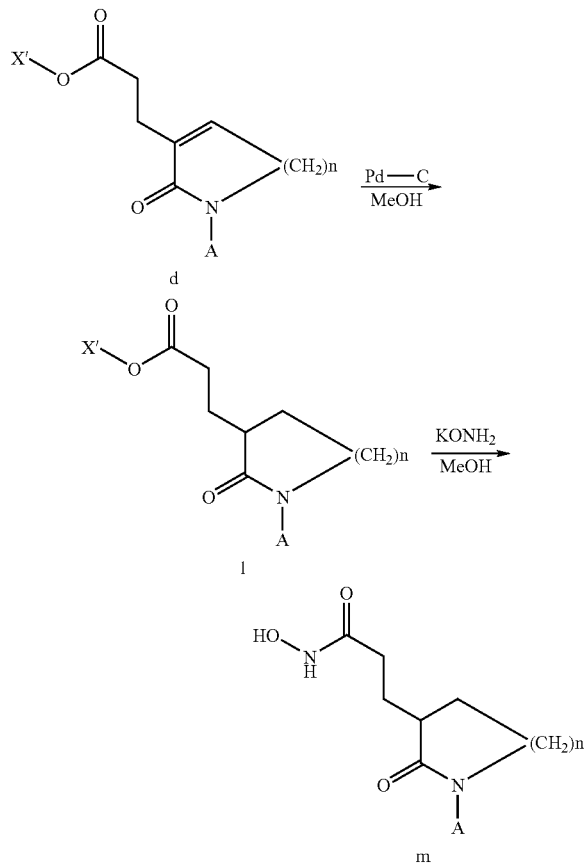

As shown in Scheme 5, the 1,2,5,6-dihydropyridine compound (d) is reduced to the piperidine compound (l) by reacting with palladium-carbon (Pd/C) under alcohol solvent in the amount of 0.1 to 0.2 equivalents of compound (d) and further the piperidine compound (l) is reacted with $KONH_2$ under MeOH to synthesize the compound (m). In the reaction, it is preferable to use the amine salt in the amount of 2 to 3 equivalents to the compound (m) at the temperature ranging from 0° C. to R. T.

Scheme 6

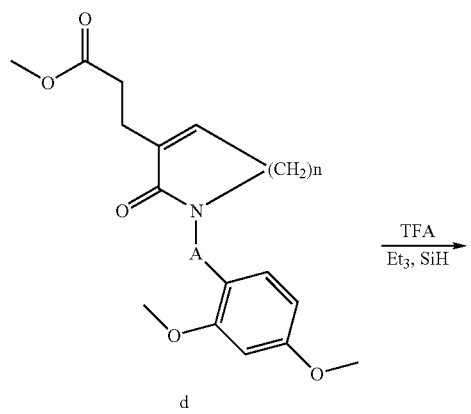

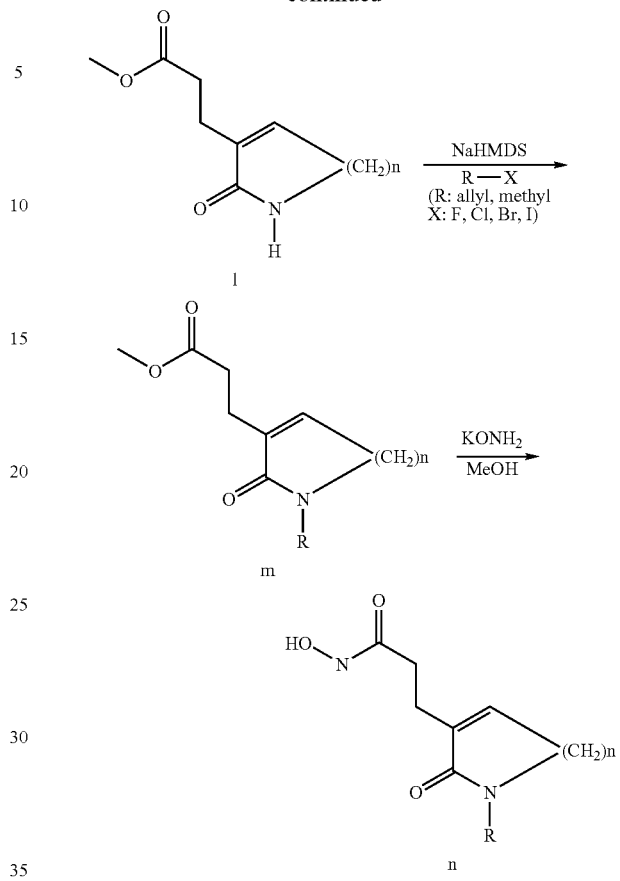

As shown in Scheme 6, the benzyl compound (d) is reacted with triethysilane (TES) in the amount of 1 to 1.5 equivalent of the compound (d) under TFA solution to produce the compound (l). The compound (l) is further reacted with hexamethyldisilylazidesodium (NaHMDS) under THF solvent and subsequently reacted with R—X (R: ally, methyl etc, X: halogen atom) to produce the compound (m). In the reaction, it is preferable to use the NaHMDS in the amount of 1 to 1.5 equivalents to the compound (l).

Scheme 7

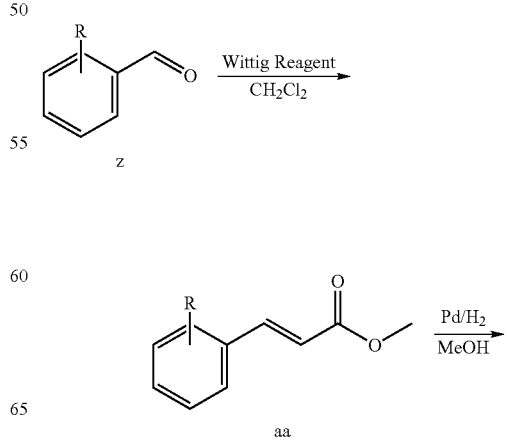

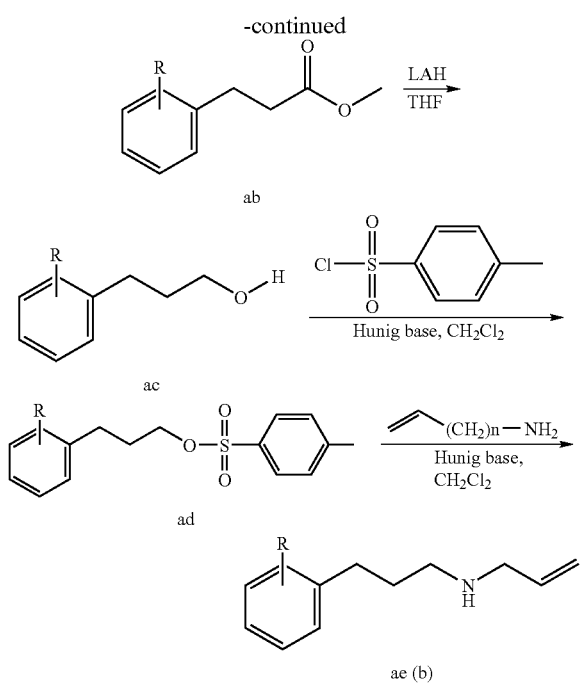

As shown in Scheme 7, the compound (b) as a starting material is prepared by following procedure: At $1^{st}$ step, the compound (z) which can be procure by conventional market or chemical company is reacted with Wittig reagent under the organic solvent such as dichloromethane to synthesize to the compound (aa). In the step, it is preferable to use the Wittig reagent in the amount of 1.5 to 2 equivalents of the compound (z) at the temperature ranging from 60 to 70° C.

At $2^{nd}$ step, the compound (aa) obtained in step 1 is reacted with Pd/C in the amount of 0.1 to 0.2 equivalents of the compound (aa) under ethyl alcohol solvent to synthesize the compound (ab).

At $3^{rd}$ step, the compound (ab) obtained in step 2 is reacted with lithium aluminum hydride (LAH) under the organic solvent such as THF to produce the compound (ac) at 0° C.

At $4^{th}$ step, the compound (ac) substiteis reacted with p-toluenesulfonylchloride, diisopropylethylamine or 4-(dimethylamino) pyridine in the amount of 0.1 to 0.2 equivalents of the compound (aa) under ethyl alcohol solvent to synthesize the compound (ab).

At $5^{th}$ step, both of allyl amine and Hunig base, i.e., diisopropylethylamine are added to the compound (ad) dissolved in acetonitrile, mixed and stirred for six hours at 80° C. to produce the compound (ae), one of the compound (b).

The present invention also provides a pharmaceutical composition comprising an efficient amount of the compound represented by general formula (I) to (VI) or the pharmaceutically acceptable salt thereof as an active ingredient in amount effective to treat or prevent cancer diseases together with pharmaceutically acceptable carriers or diluents.

The compound of formula (I) to (VI) according to the present invention can be provided as a pharmaceutical composition containing pharmaceutically acceptable carriers, adjuvants or diluents. For example, the compounds of the present invention can be dissolved in oils, propylene glycol or other solvents which are commonly used to produce an injection. Suitable examples of the carriers include physiological saline, polyethylene glycol, ethanol, vegetable oils, isopropyl myristate, etc., but are not limited to them. For topical administration, the compounds of the present invention can be formulated in the form of ointments and creams.

The pharmaceutical compositions comprising the compound of the present invention can be treat and prevent the cancer disease, for example, lung cancer, bone cancer, pancreatic cancer, skin cancer, cancer of the head and neck, cutaneous or intraocular melanoma, uterine cancer, ovarian cancer, rectal cancer or cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (eg., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphonas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

The compound of the present invention has potent anti-cancer activity, and the pharmaceutical composition of the present invention thus may be employed to treat or prevent the cancer disease.

The present invention also provides a method of preventing or treating the cancer disease which comprises administering compound selected from the group consisting of compounds of formula (I) to (VI) or pharmaceutical acceptable salts thereof in need of such prevention or treatment a therapeutically effective amount of the salt or a pharmaceutically acceptable hydrate thereof as an anti-cancer agent.

Hereinafter, the following formulation methods and excipients are merely exemplary and in no way limit the invention.

The compounds of the present invention in pharmaceutical dosage forms may be used in the form of their pharmaceutically acceptable salts, and also may be used alone or in appropriate association, as well as in combination with other pharmaceutically active compounds.

The compounds of the present invention may be formulated into preparations for injections by dissolving, suspending, or emulsifying them in aqueous solvents such as normal saline, 5% Dextrose, or non-aqueous solvent such as vegetable oil, synthetic aliphatic acid glycerides, esters of higher aliphatic acids or propylene glycol. The formulation may include conventional additives such as solubilizers, isotonic agents, suspending agents, emulsifying agents, stabilizers and preservatives.

The desirable dose of the inventive compounds varies depending on the condition and the weight of the subject, severity, drug form, route and period of administration, and may be chosen by those skilled in the art. However, in order to obtain desirable effects, it is generally recommended to administer at the amount ranging 0.0001-100 mg/kg, preferably 0.001-100 mg/kg by weight/day of the inventive compounds of the present invention. The dose may be administered in single or divided into several times per day. In terms of composition, the compounds should be present between 0.0001 to 10% by weight, preferably 0.0001 to 1% by weight based on the total weight of the composition.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intrathecal, epidural or intracerebroventricular injection.

The present invention is more specifically explained by the following examples. However, it should be understood that the present invention is not limited to these examples in any manner.

BEST MODE FOR CARRYING OUT THE INVENTION

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

EXAMPLES

The following Reference Example, Examples and Experimental Examples are intended to further illustrate the present invention without limiting its scope.

Example 1

Preparation of 3-[1-(2,4-Dimethoxybenzyl)-2-oxo-2, 5-dihydro-1H-pyrrol-3-yl]-N-hydroxypropionamide (1e)

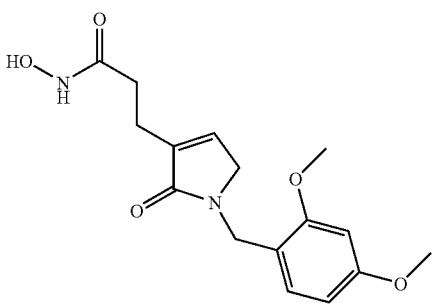

Step 1. Preparation of allyl-(2,4-dimethoxybenzyl)amine (1b)

0.32 ml of allylbromide (3.66 mM) and 0.7 ml of diisopropyl ethylamine (3.99 mM) were added to the reaction solution containing 500 mg of 2,4-dimethoxybenzylamine (3.33 mM) dissolved in methylene chloride with stirring and the solution was left alone at room temperature. After the reaction mixture was neutralized with 10% NaOH solution, the mixture was extracted with chloroform, washed with saturated NaCl solution, dried over $MgSO_4$, filtered, and concentrated in vacuo. The resulting compound was purified with Silica gel column chromatography with a solvent mixture mixed with methanol and chloroform (1:9) as an eluant to give 276 mg of allyl-(2, 4-dimethoxybenzyl)amine (1b) (yield: 40%).

$^1$H-NMR (300 MHz, $CDCl_3$) δ 7.12 (d, J=8.1 Hz, 1H), 6.44-6.39 (m, 2H), 5.99-5.86 (m, 1H), 5.21-5.09 (m, 2H), 3.79 (d, J=6.0 Hz, 6H), 3.74 (s, 2H), 3.23 (d, J=6.0 Hz, 2H)

Step 2. Preparation of 4-[allyl-(2,4-dimethoxy-benzyl)-carbamoyl]-pent-4-enoic acid methyl ester (1c)

253 mg of 2-methylene-pentane dionate-5-methyl ester (1.6 mM), 331 mg of [3-(dimethylamino)propyl]-3-ethylcarbodiimide (1.73 mM) and 48 mg of 4-(dimethylamino)pyridine (0.39 mM) were added to 0.5 M of reaction solution dissolving the compound (1b) prepared by above step 1 in methylene chloride and the mixture was stirred for 10 hrs at room temperature. After the resulting mixture was washed with 5% HCl solution (10 ml), the mixture was extracted with ethylacetate, washed with saturated NaCl. And then the extracts were washed with saturated 10 ml of $NaHCO_3$ solution and NaCl solution to separate into an organic layer and water layer. The organic layer was dried over anhydrous $MgSO_4$, filtered and concentrated in vacuo. The resultant was purified by Silica gel column chromatography with a solvent mixture mixed with EtOAc and hexanes (1:2) as an eluant to give 324 mg of 4-[allyl-(2,4-dimethoxy-benzyl)-carbamoyl]-pent-4-enoic acid methyl ester (1c) (yield: 70%).

$^1$H-NMR (300 MHz, $CDCl_3$) δ 7.14 (s, 1H), 6.44 (d, 2H), 5.72 (s, 1H), 5.12 (s, 4H), 4.56-4.81 (m 2H), 3.91-3.83 (m, 2H), 3.78 (d, J=5.3 Hz, 6H), 3.65 (d, J=1.4 Hz, 3H), 2.63 (t, J=5.7 Hz, 2H), 2.54 (t, J=5.4 Hz, 2H)

Step 3. Preparation of 311-(2,4-dimethoxybenzyl)-2-oxo-2,5-dihydro-1H-pyrrol-3-yl]-propionic acid methyl ester (1d)

324 mg of the compound (1c) (0.933 mM) prepared by the above Step 2 was added to the catalyst solution containing 74 mg of ruthenium (0.09 mM) dissolved in 93 ml of $CH_2Cl_2$. Then the mixture was stirred for 24 hrs at room temperature, filtered and concentrated in vacuo. The resultant was purified by Silica gel column chromatography with a solvent mixture mixed with EtOAc and hexanes (1:1) as an eluant to give 268 mg of 3-[1-(2,4-dimethoxybenzyl)-2-oxo-2,5-dihydro-1H-pyrole-3-yl]-propionic acid methyl ester (1d) (yield: 90%).

$^1$H-NMR (300 MHz, $CDCl_3$) δ 7.11 (d, J=9.0 Hz, 1H), 6.61 (br t, 1H), 6.43 (s, 1H), 6.40 (d, J=2.7 Hz, 1H), 4.56 (s, 2H), 3.78 (d, J=5.4 Hz, 9H), 3.65 (s, 2H), 2.61 (s, 4H)

Step 4. Preparation of 3-[1-(2,4-dimethoxy-benzyl)-2-oxo-2,5-dihydro-1H-pyrrol-3-yl]-N-hydroxy-propionamide (1e)

100 mg of compound (d) prepared by the above Step 3 was dissolved in methanol solution (0.313 mM) and then 1.7 M methanolic suspension solution containing $NH_2OK$ (0.27 ml, 0.47 mM) was added thereto at 0° C. and the resulting mixture was stirred for 4 hrs at room temperature. The resulting mixture was neutralized with 0.02 ml of acetic acid, diluted with methanol/chloroform solution, filtered and concentrated in vacuo. The resulting compound was purified by Silica gel column chromatography with a solvent mixture mixed with methanol and chloroform (1:9) as an eluant to give 50 mg of 3-[1-(2,4-dimethoxy-benzyl)-2-oxo-2,5-dihydro-1H-pyrrol-3-yl]-N-hydroxy-propionamide (1e) (yield: 50%).

$^1$H-NMR (300 MHz, $CDCl_3$) δ 7.04 (d, J=8.1 Hz, 1H), 6.83 (s, 1H), 6.53-6.44 (m, 2H), 4.54 (s, 2H), 3.81 (t, J=2.0 Hz, 6H), 2.56 (t, J=7.2 Hz, 2H), 2.34 (t, J=7.4 Hz, 2H), 1.9 (s, 3H)

Example 2

Preparation of 3-(1-benzyl-2-oxo-2,5-dihydro-1H-pyrrol-3-yl)-N-hydroxy-propionamide (2e)

3-(1-benzyl-2-oxo-2,5-dihydro-1H-pyrrol-3-yl)-N-hydroxy-propionamide (2e) was prepared by the similar procedure described in above Example 1 (See Table 1).

Example 3

Preparation of N-hydroxy-3-(2-oxo-1-phenethyl-2,5-dihydro-1H-pyrrol-3-yl)-propionamide (3e)

N-hydroxy-3-(2-oxo-1-phenethyl-2,5-dihydro-1H-pyrrol-3-yl)-propionamide (3 e) was prepared by the similar procedure described in above Example 1 (See Table 1).

Example 4

Preparation of N-hydroxy-3-[2-oxo-1-(3-phenyl-propyl)-2,5-dihydro-1H-pyrrol-3-yl]-propionamide (4e)

N-hydroxy-3-[2-oxo-1-(3-phenyl-propyl)-2,5-dihydro-1H-pyrrol-3-yl]-propionamide (4e) was prepared by the similar procedure described in above Example 1 (See Table 1).

Example 5

Preparation of N-hydroxy-3-[2-oxo-1-(4-phenyl-butyl)-2,5-dihydro-1H-pyrrol-3-yl]-propionamide (5e)

N-hydroxy-3-[2-oxo-1-(4-phenyl-butyl)-2,5-dihydro-1H-pyrrol-3-yl]-propionamide (5e) was prepared by the similar procedure described in above Example 1 (See Table 1).

Example 6

Preparation of N-hydroxy-3-[1-(2-methyl-benzyl)-2-oxo-2,5-dihydro-1H-pyrrol-3-yl]-propionamide (6e)

N-hydroxy-3-[1-(2-methyl-benzyl)-2-oxo-2,5-dihydro-1H-pyrrol-3-yl]-propionamide (6e) was prepared by the similar procedure described in above Example 1 (See Table 1).

Example 7

Preparation of N-hydroxy-3-[1-(3-methyl-benzyl)-2-oxo-2,5-dihydro-1H-pyrrol-3-yl]-propionamide (7e)

N-hydroxy-3-[1-(3-methyl-benzyl)-2-oxo-2,5-dihydro-1H-pyrrol-3-yl]-propionamide (7e) was prepared by the similar procedure described in above Example 1 (See Table 1).

Example 8

Preparation of N-hydroxy-3-[1-(4-methyl-benzyl)-2-oxo-2,5-dihydro-1H-pyrrol-3-yl]-propionamide (8e)

N-hydroxy-3-[1-(4-methyl-benzyl)-2-oxo-2,5-dihydro-1H-pyrrol-3-yl]-propionamide (8e) was prepared by the similar procedure described in above Example 1 (See Table 1).

Example 9

Preparation of N-hydroxy-3-[1-(2-methoxy-benzyl)-2-oxo-2,5-dihydro-1H-pyrrol-3-yl]-propionamide (9e)

N-hydroxy-3-[1-(2-methoxy-benzyl)-2-oxo-2,5-dihydro-1H-pyrrol-3-yl]-propionamide (9e) was prepared by the similar procedure described in above Example 1 (See Table 1).

Example 10

Preparation of N-hydroxy-3-[1-(3-methoxy-benzyl)-2-oxo-2,5-dihydro-1H-pyrrol-3-yl]-propionamide (10e)

N-hydroxy-3-[1-(3-methoxy-benzyl)-2-oxo-2,5-dihydro-1H-pyrrol-3-yl]-propionamide (10e) was prepared by the similar procedure described in above Example 1 (See Table 1).

Example 11

Preparation of N-hydroxy-3-[1-(4-methoxy-benzyl)-2-oxo-2,5-dihydro-1H-pyrrol-3-yl]-propionamide (11e)

N-hydroxy-3-[1-(4-methoxy-benzyl)-2-oxo-2,5-dihydro-1H-pyrrol-3-yl]-propionamide (11e) was prepared by the similar procedure described in above Example 1 (See Table 1).

Example 12

Preparation of 3-[1-(4-bromo-benzyl)-2-oxo-2,5-dihydro-1H-pyrrol-3-yl]-N-hydroxy-propionamide (12e)

3-[1-(4-bromo-benzyl)-2-oxo-2,5-dihydro-1H-pyrrol-3-yl]-N-hydroxy-propionamide (12e) was prepared by the similar procedure described in above Example 1 (See Table 1).

Example 13

Preparation of 3-[1-(4-chloro-benzyl)-2-oxo-2,5-dihydro-1H-pyrrol-3-yl]-N-hydroxy-propionamide (13e)

3-[1-(4-chloro-benzyl)-2-oxo-2,5-dihydro-1H-pyrrol-3-yl]-N-hydroxy-propionamide (13e) was prepared by the similar procedure described in above Example 1 (See Table 1).

Example 14

Preparation of 3-[1-(4-benzyloxy-benzyl)-2-oxo-2,5-dihydro-1H-pyrrol-3-yl]-N-hydroxy-propionamide (14e)

3-[1-(4-benzyloxy-benzyl)-2-oxo-2,5-dihydro-1H-pyrrol-3-yl]-N-hydroxy-propionamide (14e) was prepared by the similar procedure described in above Example 1 (See Table 1).

Example 15

Preparation of N-hydroxy-3-[1-(4-nitro-benzyl)-2-oxo-2,5-dihydro-1H-pyrrol-3-yl]-propionamide (15e)

N-hydroxy-3-[1-(4-nitro-benzyl)-2-oxo-2,5-dihydro-1H-pyrrol-3-yl]-propionamide (15e) was prepared by the similar procedure described in above Example 1 (See Table 1).

TABLE 1a

| Example | Chemical structure | NMR spectrum |
|---|---|---|
| 2 | 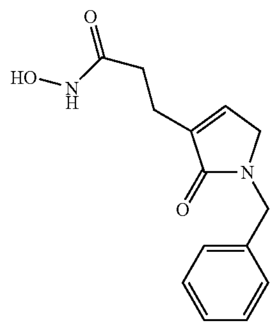 | 7.30–7.14 (m, 5H), 6.71 (d, J= 18.3 Hz, 1H), 4.59 (d, J= 7.8 Hz, 2H), 3.73 (s, 2H), 2.63 (s 4H). |
| 3 | 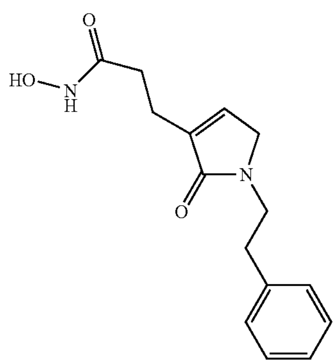 | 7.25–7.09 (m, 5H), 6.64 (s, 1H), 3.62 (t, J= 6.1 Hz, 4H), 2:81 (t, J= 7.3 Hz, 2H), 2.52 (s, 2H), 2.30 (d, J= 6.6 Hz, 2H) |
| 4 | 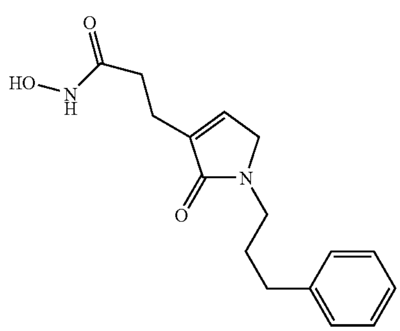 | 7.21 (d, J= 7.5 Hz, 2H), 7.12(d, J= 6.6 Hz, 3H), 6.72 (s, 1H), 3.75 (s, 2H), 3.41 (s, 2H), 2.57 (d, J= 6.3 Hz, 6H), 2.44 (s, 1H), 182 (s, 5H) |
| 5 | 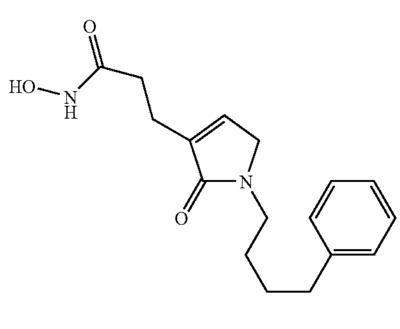 | 7.28–7.12 (m, 5H), 6.73 (s, 1H), 3.78 (d, J= 9.0 Hz, 2H), 3.43 (s, 2H), 2.61 (s, 5H), 1.58 (s, 5H) |

TABLE 1a-continued

| Example | Chemical structure | NMR spectrum |
|---|---|---|
| 6 | 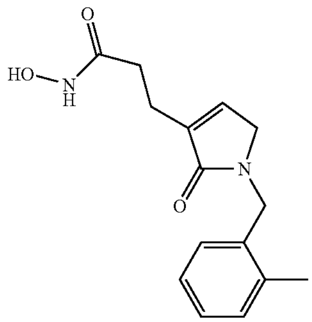 | 7.12 (s, 5H), 6.67 (s, 1H), 4.58 (d, J= 8.4 Hz, 2H), 3.64 (s, 2H), 2,61 (s, 4H), 2.34–2.22 (m, 3H) |
| 7 | 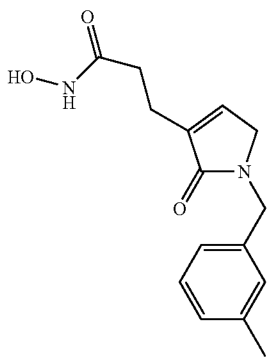 | 7.15 (d, J= 6.9 Hz, 1H), 7.02–6.95 (m, 3H), 6.74 (s, 1H), 4.52, (d, J= 8.4 Hz, 2H), 3.70 (s, 2H), 2.60 (s, 3H), 2.27 (d, J= 4.8 Hz; 4H) |
| 8 | 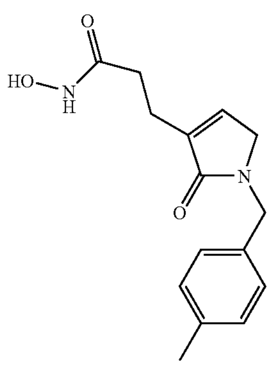 | 7.09–7.03 (m, 4H), 6.70 (d, J= 18.3 Hz, 1H), 4.54 (d, J= 7.2 Hz, 2H), 3.70 (s, 2H), 2.61 (s, 3H), 2.45 (s, 1H), 2.28 (d, J= 13.5 Hz, 3H) |

TABLE 1b

| Example | Chemical structure | NMR spectrum or LC-MS data |
|---|---|---|
| 9 | 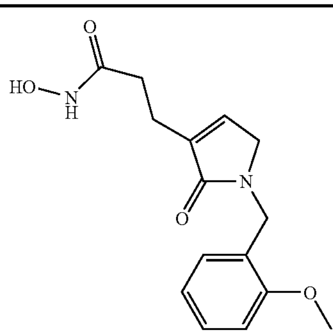 | 7.23–718 (m, 1H), 7.08 (d, J= 3.5 Hz, 1H), 6.84 (dd, J= 5.8 Hz, 2H), 6.72 (s, 1H), 4.59 (s, 2H), 3.78 (s, 3H), 3.75 (s, 2H), 2.60 (s, 2H), 2.44 (s, 2H) |

TABLE 1b-continued

| Example | Chemical structure | NMR spectrum or LC-MS data |
|---|---|---|
| 10 | 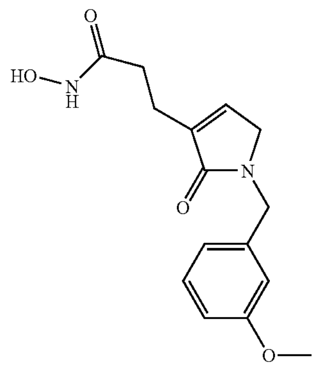 | 7.16 (t, J= 4.8 Hz, 1H), 6.73 (t, J= 5.4 Hz, 3H), 6.68 (s, 1H), 4.53 (d, J= 10.5 Hz, 2H), 3.72 (t, J= 5.2 Hz, 5H), 2.59 (s, 2H), 2.43 (s, 2H) |
| 11 | 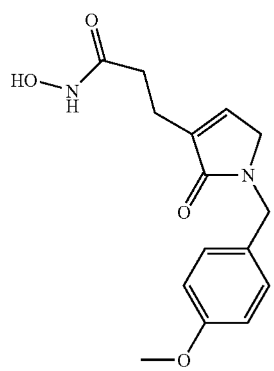 | 7.06–7.014 (m, 4H), 6.71 (s, 1H), 4.49 (s, 2H), 3.66 (s, 2H), 2.59 (s, 2H), 2.43 (s, 2H), 2.25 (s, 3H) |
| 12 | 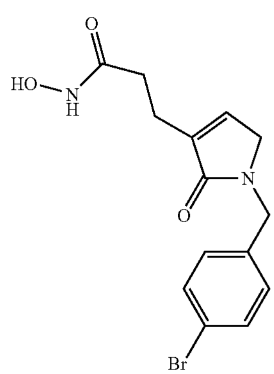 | 7.40 (d, J= 7.8 Hz, 2H), 7.05 (d, J= 8.4 Hz, 2H), 6.78 (s, 1H), 4.53 (s, 2H), 4.39 (s, 2H), 3.76 (s, 2H), 2.57 (t, J= 5.7 Hz, 2H), 2.31 (t, J= 7.2 Hz, 2H) |
| 13 | 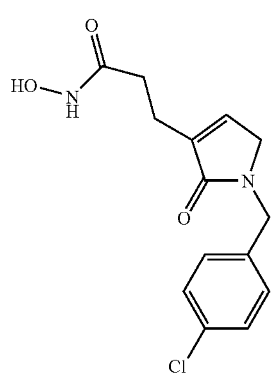 | 7.28–7.07 (m, 2H), 6.95 (t, J= 8.2 Hz, 2H), 6.74 (s, 1H), 4.52 (s, 2H), 3.60 (s, 2H), 2.54 (s, 2H), 2.31 (d, J= 7.2 Hz, 2H) |

TABLE 1b-continued

| Example | Chemical structure | NMR spectrum or LC-MS data |
|---|---|---|
| 14 | 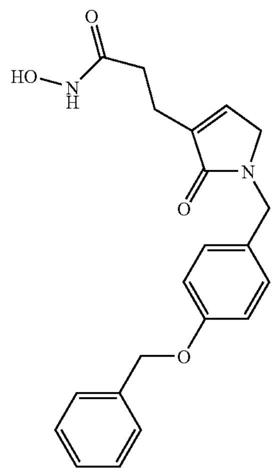 | 7.41–7.30 (m, 5H), 7.14 (d, J= 8.4 Hz, 2H), 6.91 (d, J= 8.4 Hz, 2H), 6.67 (s, 1H), 5.02 (s, 2H), 4.55 (s, 2H), 3.72 (s, 2H), 2.65 (2, 4H) |
| 15 | 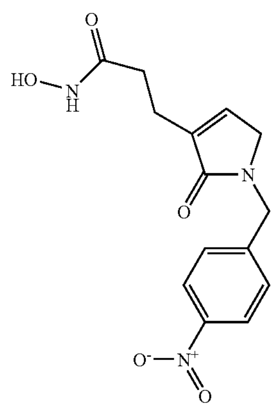 | RT: 3.82–4.54 (Mass: 306.1) |

Example 16

Preparation of 3-[1-(2,4-dimethoxy-benzyl)-2-oxo-2,5-dihydro-1H-pyrrol-3-yl]-propionic acid (16f)

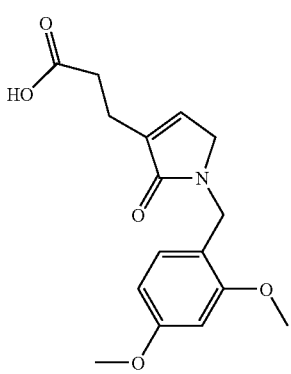

10.8 mg of LiOHH₂O solution (0.25 mM) was added to 0.86 ml of THF solution containing 55 mg of 3-[1-(2,4-dimethoxy benzyl)-2-oxo-2,5-dihydro-1H-pyrrol-3-yl]-propionic acid methyl ester (0.17 mM) in a dropwise manner at 0° C. The reaction mixture was stirred for 2 hrs at 0° C. adjust pH 1 with 5% HCl was added to the mixture to pH 1. Then the mixture was extracted three times with 10 ml of ethyl acetate, the organic layer was washed with 15 ml of saturated NaCl solution, dried over anhydrous MgSO₄, filtered and concentrated in vacuo. The resulting compound was purified with Silica gel column chromatography with a solvent mixture mixed with methanol and chloroform (1:9) as an eluant to give 41 mg of 3-[1-(2,4-dimethoxy-benzyl)-2-oxo-2,5-dihydro-1H-pyrrol-3-yl]-propionic acid (160 (yield: 80%).

$^1$H-NMR (300 MHz, CDCl₃) δ 7.11 (d, J=9.0 Hz, 1H), 6.65 (br t, 1H), 6.41 (ab, J=6.5 Hz, 1.1 Hz, 2H), 4.57 (s, 2H), 3.81-3.76 (m, 8H), 2.63 (s, 4H)

Example 17

Preparation of 3-(1-benzyl-2-oxo-2,5-dihydro-1H-pyrrol-3-yl)-propionic acid (17f)

3-(1-benzyl-2-oxo-2,5-dihydro-1H-pyrrol-3-yl)-propionic acid (170 was prepared by the similar procedure described in above Example 16 (See Table 2).

TABLE 2

| Example | Chemical structure | NMR spectrum data |
|---|---|---|
| 17 | (structure) | 7.33–7.19 (m, 5H), 6.69 (br t, 1H), 4.62 (s, 2H), 3.74 (s, 2H), 2.66 (s, 4H). |

Example 18

Preparation of N-{4-[3-(2-hydroxycarbamoyl-ethyl)-2-oxo-2,5-dihydro-pyrrole-1-yl-methyl]-phenyl}-benzamide (18j)

Step 1. Preparation of 3-[1-(4-amino-benzyl)-2-oxo-2,5-dihydro-1H-pyrrol-3-yl]-propionic acid methyl ester (h)

90 mg of 3-[1-(4-nitro-benzyl)-2-oxo-2,5-dihydro-1H-pyrrol-3-yl]-propionic acid methyl ester (0.3 mM) was dissolved in methanol solution at room temperature. And then 290 mg of Zn (4.44 mM) and 0.02 ml of acetic acid (0.3 mM) were added thereto and the mixture was stirred for 48 hrs at room temperature. The resulting compound was purified by Silica gel column chromatography with ethylacetate as an eluant to give 20 mg of 3-[1-(4-amino-benzyl)-2-oxo-2,5-dihydro-1H-pyrrol-3-yl]-propionic acid methyl ester (h) (yield: 25%).

$^1$H-NMR (300 MHz, CDCl$_3$) δ 7.01 (d, J=8.4 Hz, 2H), 6.62 (d, J=1.8 Hz, 2H), 6.60 (br t, 1H) 4.48 (s, 2H), 3.68 (d, J=1.2 Hz, 3H), 3.65 (s, 4H), 2.66-2.58 (m, 4H)

Step 2. Preparation of 3-[1-(4-benzoylamino-benzyl)-2-oxo-2,5-dihydro-1H-pyrrol-3-yl]-propionic acid methyl ester (i)

10 mg of 3-[1-(4-amino-benzyl)-2-oxo-2,5-dihydro-1H-pyrrol-3-yl]-propionic acid methyl ester (h) prepared by above Step 1 was dissolved in methylene chloride solution (0.04 mM) at room temperature. And then 8.5 μl of benzoyl chloride (0.07 mM) and 19.1 μl of diisopropylamine (0.11 mM) were added thereto and the mixture was stirred for 2 hrs at 0° C. The reaction was stopped by adding methanol and the mixture was extracted three times with 10 ml of ethyl acetate. The organic layer was washed with saturated NaCl solution, dried over anhydrous MgSO$_4$, filtered and concentrated in vacuo. The resulting compound was purified with Silica gel column chromatography with a solvent mixture mixed with ethyl acetate and hexane (1:2) as an eluant to give 12 mg of 3-[1-(4-benzoylamino-benzyl)-2-oxo-2,5-dihydro-1H-pyrrol-3-yl]-propionic acid methyl ester (i) (yield: 87%).

$^1$H-NMR (300 MHz, CDCl$_3$) δ 7.88-7.83 (m, 3H), 7.62-7.47 (m, 6H), 6.68 (br t, 1H), 4.62 (S, 2H), 3.75 (d, 2H), 3.68 (s, 3H), 2.67-2.64 (m, 4H)

Step 3. Preparation of N-{4-[3-(2-hydroxycarbamoyl-ethyl)-2-oxo-2,5-dihydro-pyrrole-1-yl-methyl]-phenyl}-benzamide (j)

7 mg of compound (i) prepared by the above Step 2 was dissolved in methanol solution (0.02 mM) and then 1.7 M methanolic suspension solution containing NH$_2$OK (0.4 ml, 0.68 mM) was added thereto at 0° C. and the resulting mixture was stirred for 8 hrs at room temperature. The resulting mixture was neutralized with 0.01 ml of acetic acid, diluted with 10% methanol/chloroform solution, filtered and concentrated in vacuo. The resulting compound was purified by Silica gel column chromatography with a solvent mixture mixed with methanol and chloroform (1:9) as an eluant to give 3.2 mg of N-{4-[3-(2-hydroxycarbamoyl-ethyl)-2-oxo-2,5-dihydro-pyrrole-1-yl-methyl]-phenyl}-benzamide (j) (yield: 46%).

$^1$H-NMR (300 MHz, CDCl$_3$) δ 7.86 (d, J=6.6 Hz, 2H), 7.62 (d, J=8.7 Hz, 2H), 7.53-7.39 (m, 4H), 7.17 (d, J=8.4 Hz, 2H), 6.77 (br t, 1H), 4.57 (s, 2H), 3.77 (s, 2H), 2.58 (t, J=7.3. Hz, 2H), 2.31 (t, J=7.2 Hz, 2H)

Example 19

Preparation of N-hydroxy-3-{2-oxo-1-[4-(toluene-4-sulfonylamino)-benzyl]-2,5-dihydro-1H-pyrrol-3-yl}-propionamide (19j)

N-hydroxy-3-{2-oxo-1-[4-(toluene-4-sulfonylamino)-benzyl]-2,5-dihydro-1H-pyrrol-3-yl}-propionamide (19j) was prepared by the similar procedure described in above Example 18 (See Table 3).

TABLE 3

| Example | Chemical structure | NMR spectrum data |
|---|---|---|
| 19 | (structure) | 7.61 (t, J= 7.0 Hz, 3H), 7.05-6.89 (m, 6H), 4.54 (s, 3H), 3.74 (s, 3H), 3.39 (s, 3H), 2.37 (s, 3H), RT: 3.87–4.34 (Mass: 430.0) |

Example 20

Preparation of 2-(1-benzyl-2-oxo-2,5-dihydro-1H-pyrrol-3-yl)-N-hydroxy-acetamide (20q)

Step 1. Preparation of 3-(allyl-benzyl-carbamoyl)-but-3-enoic acid methyl ester (o)

587 mg of 2-methylene-succinate 4-methyl ester (4.07 mM), 781 mg of 143-(dimethylamino)propyl]-3-ethylcarbodiimide (4.07 mM) and 75 mg of 4-(dimethylamino)pyridine (0.61 mM) were added to the reaction solution containing 300 mg of allylbenzylamine (2.04 mM) dissolved in methylene chloride solution (0.5M) with stirring for 10 hrs at room temperature. After the resulting mixture was washed with 5% HCl solution (10 ml), the mixture was diluted with ethyl acetate, washed with 10 ml of solution mixture mixed with saturated $NaHCO_3$ solution and saturated NaCl solution to separate into an organic layer and water layer. The organic layer was dried over anhydrous $MgSO_4$, filtered and concentrated in vacuo. The resultant was purified by Silica gel column chromatography with a solvent mixture mixed with EtOAc and hexanes (1:1) as an eluant to give 272 mg of 3-(allyl-benzyl-carbamoyl)-but-3-enoic acid methyl ester (o) (yield: 49%).

$^1$H-NMR (300 MHz, $CDCl_3$) δ 7.30-7.22 (m, 5H), 5.84-5.71 (m, 1H), 5.37-5.15 (m, 4H), 4.75-4.65 (m, 2H), 4.02 (s, 2H), 3.63 (s, 3H), 3.48 (s, 2H)

Step 2. Preparation of (1-benzyl-2-oxo-2,5-dihydro-1H-pyrrol-3-yl)-acetic acid methyl ester (p)

234 mg of 3-(allyl-benzyl-carbamoyl)-but-3-enoic acid methyl ester (o) (0.1 mM) prepared by the above Step 1 was added to the catalyst solution containing 36 mg of Grubb's (I) catalyst (0.04 mM) such as ruthenium dissolved in $CH_2Cl_2$ under Ar atmosphere. Then the mixture was stirred for 24 hrs at room temperature, filtered and concentrated in vacuo. The resultant was purified by Silica gel column chromatography with a solvent mixture mixed with EtOAc and hexanes (1:2) as an eluant to give 180 mg of (1-benzyl-2-oxo-2,5-dihydro-1H-pyrrol-3-yl)-acetic acid methyl ester (p) (yield: 85%).

$^1$H-NMR (300 MHz, $CDCl_3$) δ 7.33-7.18 (m, 5H), 6.94 (t, J=1.5 Hz, 1H), 4.61 (s, 2H), 3.79 (d, J=0.7 Hz, 2H), 3.70 (s, 3H), 3.37 (d, J=1.5 Hz, 2H)

Step 3. Preparation of 2-(1-benzyl-2-oxo-2,5-dihydro-1H-pyrrol-3-yl)-N-hydroxy-acetamide (q)

24 mg of (1-benzyl-2-oxo-2,5-dihydro-1H-pyrrol-3-yl)-acetic acid methyl ester (p) prepared by the above Step 2 was dissolved in methanol solution (0.1 mM) and then 1.7 M methanolic suspension solution containing $NH_2OK$ (0.4 ml, 0.68 mM) was added thereto at 0° C. and the resulting mixture was stirred for 4 hrs at room temperature. The resulting mixture was neutralized with 0.02 ml of acetic acid, diluted with 10% methanol/chloroform solution, filtered and concentrated in vacuo. The resulting compound was purified by Silica gel column chromatography with a solvent mixture mixed with methanol and chloroform (1:9) as an eluant to give 12 mg of 2-(1-benzyl-2-oxo-2,5-dihydro-1H-pyrrol-3-yl)-N-hydroxy-acetamide (q) (yield: 48%).

$^1$H-NMR (300 MHz, $CDCl_3$) δ 7.35-7.21 (m, 5H), 7.05 (br t, 1H), 4.63 (s, 2H), 3.90 (s, 2H), 3.30 (t, J=1.5 Hz, 1H), 3.13 (s, 2H)

Example 21

Preparation of 241-(2,4-dimethoxy-benzyl)-2-oxo-2,5-dihydro-1H-pyrrol-3-yl]-N-hydroxy-acetamide (21q)

2-[1-(2,4-dimethoxy-benzyl)-2-oxo-2,5-dihydro-1H-pyrrol-3-yl]-N-hydroxy-acetamide (21 q) was prepared by the similar procedure described in above Example 20 (See Table 4).

Example 22

Preparation of N-hydroxy-2-(2-oxo-1-phenethyl-2,5-dihydro-1H-pyrrol-3-yl)-acetamide (22q)

N-hydroxy-2-(2-oxo-1-phenethyl-2,5-dihydro-1H-pyrrol-3-yl)-acetamide (22q) was prepared by the similar procedure described in above Example 20 (See Table 4).

Example 23

Preparation of N-hydroxy-2-[2-oxo-1-(4-phenyl-butyl)-2,5-dihydro-1H-pyrrol-3-yl]-acetamide (23q)

N-hydroxy-2-[2-oxo-1-(4-phenyl-butyl)-2,5-dihydro-1H-pyrrol-3-yl]-acetamide (23q) was prepared by the similar procedure described in above Example 20 (See Table 4).

Example 24

Preparation of 2-[1-(4-benzyloxy-benzyl)-2-oxo-2,5-dihydro-1H-pyrrol-3-yl]-N-hydroxy-acetamide (24q)

2-[1-(4-benzyloxy-benzyl)-2-oxo-2,5-dihydro-1H-pyrrol-3-yl]-N-hydroxy-acetamide (24q) was prepared by the similar procedure described in above Example 20 (See Table 4).

TABLE 4

| Example | Chemical structure | NMR spectrum data |
| --- | --- | --- |
| 21 | (structure shown) | 7.12 (d, J= 8.4 Hz, 2H), 6.90(d, J= 20.7 Hz, 1H), 6.43 (d, J= 6.0 Hz), 4.57 (d, J= 2.7 Hz; 2H), 3.86 (d, J= 15.9 Hz, 2H), 3.79 (d, J= 3.0 Hz, 6H) |

TABLE 4-continued

| Example | Chemical structure | NMR spectrum data |
|---|---|---|
| 22 | 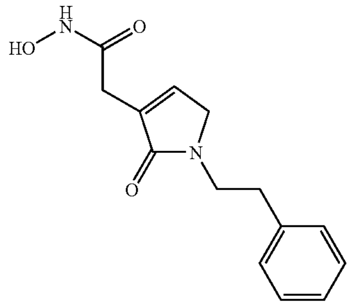 | 7.29–7.14 (m, 5H), 6.90 (br t, 1H), 3.75–3.65 (m, 4H), 3.23 (s, 1H), 2.92–2.84 (m, 2H) |
| 23 | 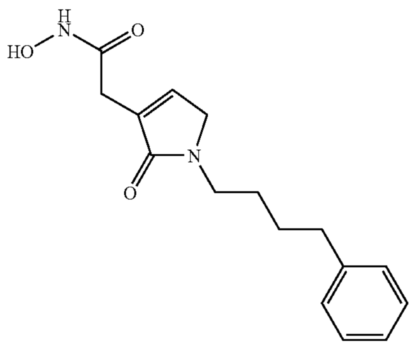 | 7.21 (t, J= 7.4 Hz, 2H), 7.11 (d, J= 7.8 Hz, 3H) 6.76 (br t, 1H), 5.22 (s, 1H), 3.30 2.04 (s, 3H), 1.82 (s, 3H), 1.57 (s, 4H) |
| 24 | 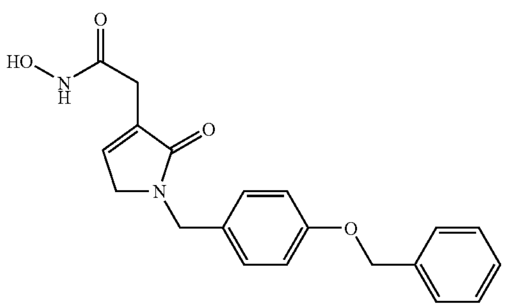 | 7.39–7.31 (m, 5H), 7.13 (d, J= 8.4 Hz, 2H), 6.92 (d, J= 8.7 Hz, 3H), 5.03 (s, 2H), 4.56 (s, 2H), 3.82 (4 J= 13.8 Hz, 2H), 3.53 (s, 1H), 3.31 (s, 1H) |

Example 25

Preparation of 2-(1-benzyl-2-oxo-pyrrolidin-3-yl)-N-hydroxy-acetamide (25s)

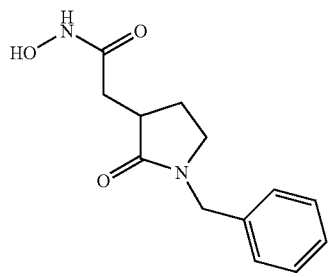

Step 1. Preparation of (2-oxo-1-phenethyl-pyrrolidin-3-yl)-acetic acid methyl ester (25r)

30 mg of (1-benzyl-2-oxo-2,5-dihydro-1H-pyrrol-3-yl)-acetic acid methyl ester was dissolved in methanol solution (0.12 mM) under nitrogen atmosphere. Then 2.6 mg of Pd—C (0.02 mM) was added thereto, and hydrogenated under a hydrogen balloon for 1 to 2 hrs at room temperature. The reaction mixture was filtered and concentrated in vacuo. The resulting compound was purified with Silica gel column chromatography with a solvent mixture mixed with EtOAc and hexane (1:1) as an eluant to give (2-oxo-1-phenethyl-pyrrolidin-3-yl)-acetic acid methyl ester (25r) (yield: 95%).

$^1$H-NMR (300 MHz, CDCl$_3$) δ 7.34-7.19 (m, 5H), 4.44 (ab, J=19.8 Hz, 7.4 Hz, 2H), 3.67 (s, 3H), 3.21-3.16 (m, 2H), 2.96 (m, 2H), 2.43 (dd, J=8.7 Hz, 7.9 Hz, 1H), 2.34-2.23 (m, 1H), 1.76-1.65 (m, 1H)

Step 2. Preparation of 2-(1-benzyl-2-oxo-pyrrolidin-3-yl)-N-hydroxy-acetamide (25s)

12 mg of (2-oxo-1-phenethyl-pyrrolidin-3-yl)-acetic acid methyl ester (25r) prepared by the above Step 1 was dissolved in methanol solution (0.04 mM) and then 1.7 M methanolic suspension solution containing NH$_2$OK (0.07 ml, 0.12 mM) was added thereto at 0° C. and the resulting mixture was stirred for 4 hrs at room temperature. The resulting mixture was neutralized with 0.02 ml of acetic acid, diluted with 10% methanol/chloroform solution, filtered and concentrated in vacuo. The resulting compound was purified by Silica gel column chromatography with a solvent mixture mixed with methanol and chloroform (1:9) as an eluant to give 1.6 mg of 2-(1-benzyl-2-oxo-pyrrolidin-3-yl)-N-hydroxy-acetamide (25s) (yield: 8%).

$^1$H-NMR (300 MHz, CDCl$_3$) δ 7.34-7.19 (m, 5H), 4.46 (d, J=8.1 Hz, 2H), 3.35-3.20 (m, 2H), 3.01-2.71 (m, 2H), 2.66-2.44 (m, 2H), 2.35-2.22 (m, 2H), 1.81-1.58 (m, 2H)

Example 26

Preparation of 2-[1-(2,4-dimethoxy-benzyl)-2-oxo-pyrrolidin-3-yl]-N-hydroxy-acetamide (26s)

2-[1-(2,4-dimethoxy-benzyl)-2-oxo-pyrrolidin-3-yl]-N-hydroxy-acetamide (26s) was prepared by the similar procedure described in above Example 25 (See Table 5).

Example 27

Preparation of N-hydroxy-2-(2-oxo-1-phenethyl-pyrrolidin-3-yl)-acetamide (27s)

N-hydroxy-2-(2-oxo-1-phenethyl-pyrrolidin-3-yl)-acetamide (27s) was prepared by the similar procedure described in above Example 25 (See Table 5).

Example 28

Preparation of 3-{1-[2-(2-fluoro-phenyl)-ethyl]-2-oxo-2,5-dihydro-M-pyrrol-3-yl}-N-hydroxy-propionamide (28y)

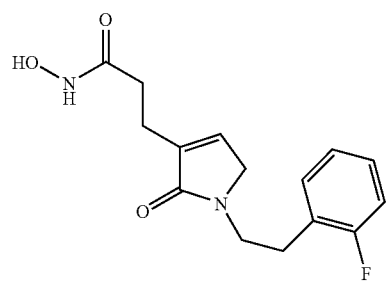

Step 1. Preparation of toluen-4-sulfonate-2-(2-fluoro-phenyl)-ethyl ester (u)

1.02 g of p-toluensulfonyl chloride (5.35 mM), 1.24 ml of diisopropyl ethylamine (7.13 mM) and 86 mg of 4-(dimethylamino)pyridine (0.71 mM) were added to the reaction solution (3.57 mM) containing 500 mg of 2-(2-fluoro-phenyl)-ethanol (3.57 mM) dissolved in methylene chloride solution

TABLE 5

| Example | Chemical structure | NMR spectrum data |
|---|---|---|
| 26 | 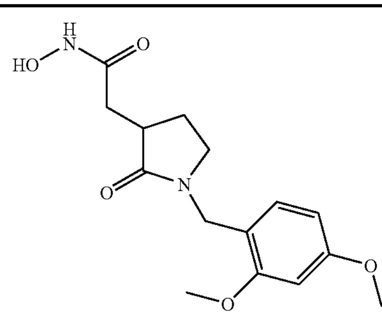 | 7.10 (t, J= 9.3 Hz, 1H), 6.44 (t, J= 2.6 Hz, 2H), 4.43 (dd, J= 14.3 Hz, 14.8 Hz, 2H), 3.78 (s, 6H), 3.31–3.21 (m, 2H), 2.88–2.68 (m, 1H), 2.56–2.49 (m, 1H), 2.26–2.22 (m, 1H), 1.71–1.60 (m, 1H) |
| 27 | | 7.30–7.15 (m, 5H), 3.50 (t, J= 7.1 Hz, 2H), 3.25–3.11 (m, 2H), 2.86–2.66 (m, 3H), 2.57–2.44 (m, 1H), 2.32–2.21 (m, 2H), 1.77–1.62 (m, 1H) | with stirring for 6 hrs at 0° C. under Ar atmosphere, and then the reaction mixture was stirred for 12 hrs at room temperature. The resulting mixture was neutralized with ammonium chloride, extracted with ethyl acetate and washed with saturated NaCl solution to separate into an organic layer and water layer. The organic layer was dried over anhydrous MgSO$_4$, filtered and concentrated in vacuo. The resultant was purified by Silica gel column chromatography with a solvent mixture mixed with methanol and chloroform (1:7) as an eluant to give 740 mg of toluen-4-sulfonate-2-(2-fluoro-phenyl)-ethyl ester (u) (yield: 70%).

Step 2. Preparation of allyl-[2-(2-fluoro-phenyl)-ethyl]-amine (v)

0.89 ml of allylamine (11.89 mM) and 0.31 ml of diisopropyl ethylamine (1.78 mM) were added to the reaction solution (1.19 mM) containing 350 mg of toluen-4-sulfonate-2-(2-fluoro-phenyl)-ethyl ester (u) prepared by above Step 1 dissolved in acetonitrile solution with stirring for 6 hrs at 80° C. After the reaction mixture was neutralized with 10% NaOH solution, the mixture was extracted with chloroform, washed with saturated NaCl solution, dried over MgSO$_4$, filtered, and concentrated in vacuo. The resultant was purified by Silica gel column chromatography with a solvent mixture mixed with methanol and chloroform (1:9) as an eluant to give 141 mg of allyl-[2-(2-fluoro-phenyl)-ethyl]-amine (v) (yield: 66%).

Step 3. Preparation of 4-{allyl-[2-(3-fluoro-phenyl)-ethyl]-carbamoyl}-pent-4-enoic acid methyl ester (w)

106 mg of 2-methylene-pentane dionate-5-methyl ester (0.67 mM), 139 mg of 143-(dimethylamino)propyl]-3-ethyl-carbodiimide (0.73 mM) and 20 mg of 4-(dimethylamino) pyridine (0.17 mM) were added to reaction solution (0.56 mM) dissolving 100 mg of allyl-[2-(2-fluoro-phenyl)-ethyl]-amine (v) prepared by above step 2 in methylene chloride and the mixture was stirred for 10 hrs at room temperature. After the resulting mixture was washed with 5% HCl solution (10 ml), the mixture was extracted with ethylacetate, washed with saturated NaCl. And then the extracts were washed with 10 ml of saturated NaHCO$_3$ solution and NaCl solution to separate into an organic layer and water layer. The organic layer was dried over anhydrous MgSO$_4$, filtered and concentrated in vacuo. The resultant was purified by Silica gel column chromatography with a solvent mixture mixed with EtOAc and hexanes (1:2) as an eluant to give 128 mg of 4-{allyl-[2-(3-fluoro-phenyl)-ethyl]-carbamoyl}-pent-4-enoic acid methyl ester (w) (yield: 72%).

$^1$H-NMR (300 MHz, CDCl$_3$) δ 7.19-7.09 (m, 1H), 7.04-6.94 (m, 3H), 5.84-5.57 (m, 1H), 5.13 (t, J=10.7 Hz, 4H), 5.06-4.94 (m, 2H), 3.79 (s, 2H), 3.62 (s, 4H), 3.53 (d, J=5.4 Hz, 3H), 2.89 (d, J=6.0 Hz, 3H)

Step 4. Preparation of 3-{1-[2-(2-fluoro-phenyl)-ethyl]-2-oxo-2,5-dihydro-1H-pyrrol-3-yl}-propionic acid methyl ester (x)

100 mg of 4-{allyl-[2-(3-fluoro-phenyl)-ethyl]-carbamoyl}-pent-4-enoic acid methyl ester (w) (0.31 mM) prepared by the above Step 3 was added to the catalyst solution containing 27 mg of ruthenium catalyst (0.03 mM) dissolved in 31.3 ml of CH$_2$Cl$_2$ under Ar atmosphere. Then the mixture was stirred for 24 hrs at room temperature, filtered and concentrated in vacuo. The resultant was purified by Silica gel column chromatography with a solvent mixture mixed with EtOAc and hexanes (1:1) as an eluant to give 69 mg of 3-{1-[2-(2-fluoro-phenyl)-ethyl]-2-oxo-2,5-dihydro-1H-pyrrol-3-yl}-propionic acid methyl ester (x) (yield: 75%).

$^1$H-NMR (300 MHz, CDCl$_3$) δ 7.16-7.12 (m, 2H), 7.03-6.93 (m, 2H), 6.59 (br t, 1H), 3.67-3.65 (m, 4H), 3.62 (s, 3H), 2.89 (t, J=7.3 Hz, 2H), 2.56 (s, 4H)

Step 5. Preparation of 3-{1-[2-(2-fluoro-phenyl)-ethyl]-2-oxo-2,5-dihydro-1H-pyrrol-3-yl}-N-hydroxy-propionamide (28y)

38 mg of 3-{1-[2-(2-fluoro-phenyl)-ethyl]-2-oxo-2,5-dihydro-1H-pyrrol-3-yl}-propionic acid methyl ester (x) prepared by the above Step 4 was dissolved in methanol solution (0.13 mM) and then 1.7 M methanolic suspension solution containing NH$_2$OK (0.38 ml, 0.65 mM) was added thereto at 0° C. and the resulting mixture was stirred for 8 hrs at room temperature. The resulting mixture was neutralized with 0.02 ml of acetic acid, diluted with 10% methanol/chloroform solution, filtered and concentrated in vacuo. The resulting compound was purified by Silica gel column chromatography with a solvent mixture mixed with methanol and chloroform (1:9) as an eluant to give 25 mg of 3-{1-[2-(2-fluoro-phenyl)-ethyl]-2-oxo-2,5-dihydro-1H-pyrrol-3-yl}-N-hydroxy-propionamide (28y) (yield: 65%).

$^1$H-NMR (300 MHz, CDCl$_3$) δ 7.19-7.08 (m, 2H), 7.02-6.92 (m, 2H), 6.69 (br t, 1H), 3.69 (s, 2H), 3.63 (t, J=7.0 Hz, 2H), 2.87 (t, J=7.0 Hz, 2H), 2.51 (t, J=7.0 Hz, 2H), 2.25 (t, 7.3 Hz, 2H)

Example 29

Preparation of 3-{1-[2-(3-fluoro-phenyl)-ethyl]-2-oxo-2,5-dihydro-1H-pyrrol-3-yl}-N-hydroxy-propionamide (29y)

3-{1-[2-(3-fluoro-phenyl)-ethyl]-2-oxo-2,5-dihydro-1H-pyrrol-3-yl}-N-hydroxy-propionamide (29y) was prepared by the similar procedure described in above Example 28 (See Table 6).

Example 30

Preparation of 3-{1-[2-(4-fluoro-phenyl)-ethyl]-2-oxo-2,5-dihydro-1H-pyrrol-3-yl}-N-hydroxy-propionamide (30y)

3-{1-[2-(4-fluoro-phenyl)-ethyl]-2-oxo-2,5-dihydro-1H-pyrrol-3-yl}-N-hydroxy-propionamide (30y) was prepared by the similar procedure described in above Example 28 (See Table 6).

Example 31

Preparation of N-hydroxy-3-{1-[2-(2-nitro-phenyl)-ethyl]-2-oxo-2,5-dihydro-1H-pyrrol-3-yl}-propionamide (31y)

N-hydroxy-3-{1-[2-(2-nitro-phenyl)-ethyl]-2-oxo-2,5-dihydro-1H-pyrrol-3-yl}-propionamide (31y) was prepared by the similar procedure described in above Example 28 (See Table 6).

Example 32

Preparation of N-hydroxy-3-{1-[2-(3-nitro-phenyl)-ethyl]-2-oxo-2,5-dihydro-1H-pyrrol-3-yl}-propionamide (32y)

N-hydroxy-3-{1-[2-(3-nitro-phenyl)-ethyl]-2-oxo-2,5-dihydro-1H-pyrrol-3-yl}-propionamide (32y) was prepared by the similar procedure described in above Example 28 (See Table 6).

Example 33

Preparation of N-hydroxy-3-{1-[2-(4-nitro-phenyl)-ethyl]-2-oxo-2,5-dihydro-1H-pyrrol-3-yl}-propionamide (33y)

N-hydroxy-3-{1-[2-(4-nitro-phenyl)-ethyl]-2-oxo-2,5-dihydro-1H-pyrrol-3-yl}-propionamide (33y) was prepared by the similar procedure described in above Example 28 (See Table 6).

Example 34

Preparation of 3-{1-[2-(2-bromo-phenyl)-ethyl]-2-oxo-2,5-dihydro-1H-pyrrol-3-yl}-N-hydroxy-propionamide (34y)

3-{1-[2-(2-bromo-phenyl)-ethyl]-2-oxo-2,5-dihydro-1H-pyrrol-3-yl}-N-hydroxy-propionamide (34y) was prepared by the similar procedure described in above Example 28 (See Table 6).

Example 35

Preparation of 3-{1-[2-(4-bromo-phenyl)-ethyl]-2-oxo-2,5-dihydro-1H-pyrrol-3-yl}-N-hydroxy-propionamide (35y)

3-{1-[2-(4-bromo-phenyl)-ethyl]-2-oxo-2,5-dihydro-1H-pyrrol-3-yl}-N-hydroxy-propionamide (35y) was prepared by the similar procedure described in above Example 28 (See Table 6).

Example 36

Preparation of N-hydroxy-3-{1-[2-(2-methoxy-phenyl)-ethyl]-2-oxo-2,5-dihydro-1H-pyrrol-3-yl}-propionamide (36y)

N-hydroxy-3-{1-[2-(2-methoxy-phenyl)-ethyl]-2-oxo-2,5-dihydro-1H-pyrrol-3-yl}-propionamide (36y) was prepared by the similar procedure described in above Example 28 (See Table 6).

Example 37

Preparation of N-hydroxy-3-{1-[2-(3-methoxy-phenyl)-ethyl]-2-oxo-2,5-dihydro-1H-pyrrol-3-yl}-propionamide (37y)

N-hydroxy-3-{1-[2-(3-methoxy-phenyl)-ethyl]-2-oxo-2,5-dihydro-1H-pyrrol-3-yl}-propionamide (37y) was prepared by the similar procedure described in above Example 28 (See Table 6).

Example 38

Preparation of N-hydroxy-3-{1-[2-(4-methoxy-phenyl)-ethyl]-2-oxo-2,5-dihydro-1H-pyrrol-3-yl}-propionamide (38y)

N-hydroxy-3-{1-[2-(4-methoxy-phenyl)-ethyl]-2-oxo-2,5-dihydro-1H-pyrrol-3-yl}-propionamide (38y) was prepared by the similar procedure described in above Example 28 (See Table 6).

Example 39

Preparation of N-hydroxy-3-[2-oxo-1-(2-p-tolyl-ethyl)-2,5-dihydro-1H-pyrrol-3-yl]-propionamide (39y)

N-hydroxy-3-[2-oxo-1-(2-p-tolyl-ethyl)-2,5-dihydro-1H-pyrrol-3-yl]-propionamide (39y) was prepared by the similar procedure described in above Example 28 (See Table 6).

TABLE 6

| Example | Chemical structure | NMR spectrum data |
|---|---|---|
| 29 | 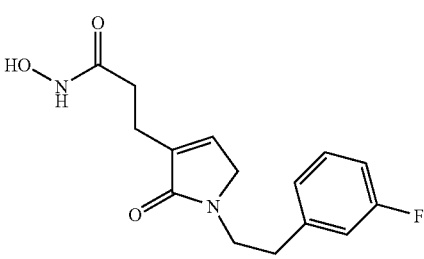 | 7.25–7.18 (m, 1H), 6.90 (ab, J= 18.3 Hz, 4.3 Hz, 3H), 6.71 (br t, 1H), 3.65 (t, J= 6.9 Hz, 4H), 2.85 (t, J= 6.9 Hz, 2H), 2.61 (s, 2H), 2.45 (s, 2H) |

TABLE 6-continued
| Example | Chemical structure | NMR spectrum data |
|---|---|---|
| 30 | 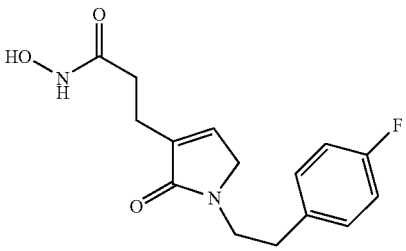 | 7.11–6.94 (m, 4H), 6.70 (br t, 1H), 3.65 (s, 4H), 2.82 (s, 3H), 2.68–2.60 (m, 3H) |
| 31 | 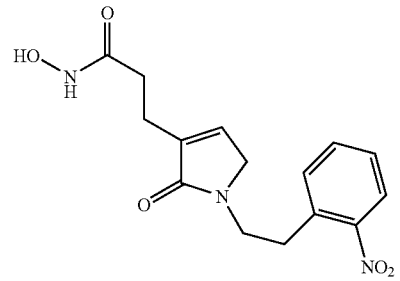 | 7.93 (d, J= 7.8 Hz, 1H), 7.56 (t, J= 6.7 Hz, 1H), 7.44–7.36 (m, 2H), 6.81 (br t, 1H), 3.85 (s, 2H), 3.76 (t, J= 7.3 Hz, 2H), 3.15 (t, J= 7.1 Hz, 2H), 2.54 (t, J= 7.1 Hz, 2H), 2.30 (t, J= 7.4 Hz, 2H) |
| 32 | 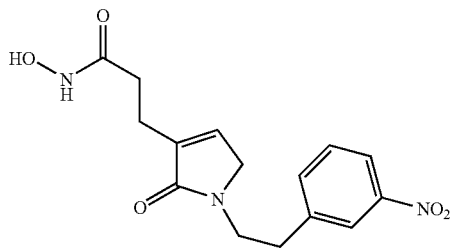 | 8.00 (d, J=7.2 Hz, 2H), 7.49–7.38 (m, 2H), 6.70 (br t, 1H), 3.72 (s, 2H), 3.64 (t, J= 7.2 Hz, 2H), 2.93 (t, J= 7.4 Hz, 2H), 2.48 (t, J= 7.3 Hz, 2H), 2.22 (t, J= 7.7 Hz, 2H) |
| 33 | 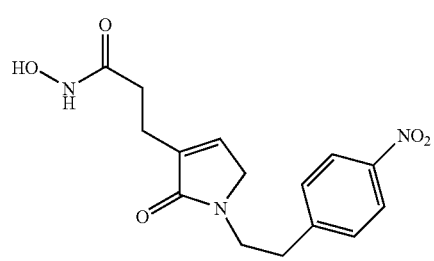 | 8.09 (d, J= 8.4 Hz, 2H), 7.36 (d, J= 9.6 Hz, 2H), 6.74 (br t, 1H), 3.76 (d, J= 1.2 Hz, 1H), 3.69 (t, J= 7.1 Hz, 1H), 3.29 (d, J= 7.8 Hz, 1H), 3.26 (dd, J= 1.8 Hz, 1.5 Hz, 1H), 2.97 (t, J= 7.3 Hz, 2H), 2.49 (t, J= 6.9 Hz, 2H), 2.25 (t, J= 7.6 Hz, 2H) |
| 34 | 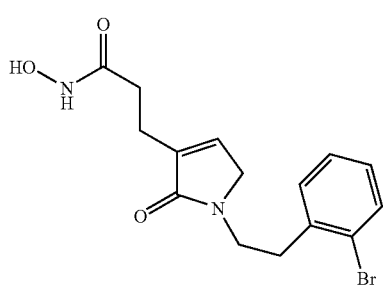 | 7.48 (d, J= 8.1 Hz, 2H), 7.21–7.13 (m, 2H), 7.07–7.02 (m, 1H), 6.71 (br t, 1H), 3.70–3.62 (m, 4H), 2.98 (t, J= 7.3 Hz, 2H), 2.52 (t, J= 7.3 Hz, 2H), 2.27 (t, J= 7.6 Hz, 2H) |

TABLE 6-continued

| Example | Chemical structure | NMR spectrum data |
| --- | --- | --- |
| 35 | 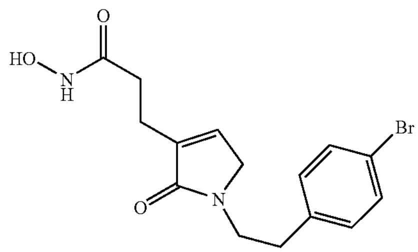 | 7.40 (d, J= 8.4 Hz, 2H), 7.10 (d, J= 8.1 Hz, 2H), 6.79 (br t, 1H), 3.78 (d, J= 1.2 Hz, 2H), 3.66 (t, J= 7.3 Hz, 2H), 2.85 (t, J= 7.1 Hz, 2H), 2.54 (t, J= 7.1 Hz, 2H), 2.30 (t, J= 7.4 Hz, 2H) |
| 36 | 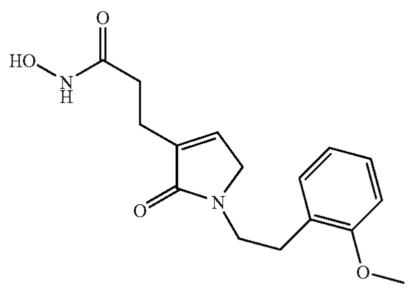 | 7.19–7.13 (m, 1H), 7.03–7.01 (m, 1H), 6.81(t, J= 7.4 Hz, 2H), 6.70 (br t, 1H), 3.78(s, 3H), 3.69 (s, 2H), 3.63 (t, J= 7.0 Hz, 2H), 2.85 (t, J= 7.1 Hz, 2H), 2.52 (t, J= 7.7 Hz, 2H), 2.27 (t, J= 7.6 Hz, 2H) |
| 37 | 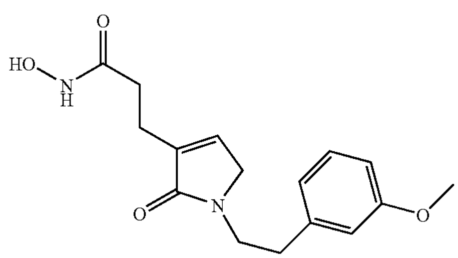 | 7.14(t, J= 7.6 Hz, 1H), 6.72–6.67 (m, 4H), 3.72 (s, 3H), 3.65 (s, 2H), 3.60 (br t, 2H), 2.80 (t, J= 7.1 Hz, 2H), 2.51 (t, J= 7.3 Hz, 2H), 2.25 (t, J= 7.3 Hz, 2H) |
| 38 | 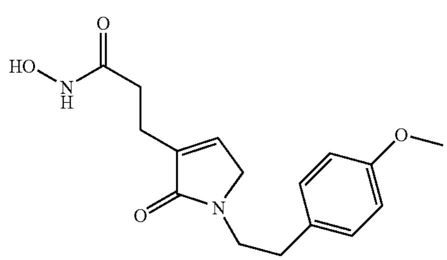 | 7.02 (d, J= 8.7 Hz, 2H), 6.76 (d, J= 8.4 Hz, 2H), 6.66 (br t, 1H), 3.72 (s, 3H), 3.62–3.56 (m, 4H), 2.76 (t, J= 7.3 Hz, 2H), 2.51 (t, J= 7.3 Hz, 2H), 2.25 (t, J= 7.6 Hz, 2H) |
| 39 | 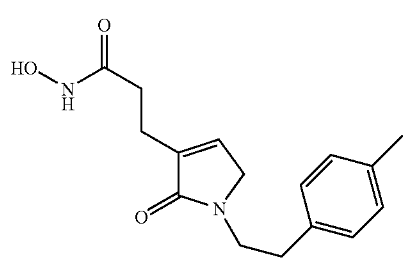 | 7.05 (s, 4H), 6.74 (br t, 1H), 3.72 (d, J= 1.2 Hz, 2H), 3.64 (t, J= 7.3 Hz, 2H), 3.31–3.29 (m, 2H), 2.82 (t, J= 7.3 Hz, 2H), 2H), 2.54 (t, J= 7.1 Hz, 2H), 2.31 (d, J= 7.8 Hz, 2H), 2.27 (s, 3H). |

Example 40

Preparation of N-hydroxy-3-{1-[3-(4-methoxy-phenyl)-propyl]-2-oxo-2,5-dihydro-1H-pyrrol-3-yl}-propionamide (40ah)

Step 1. Preparation of 3-p-tolyl-acrylic acid methyl ester (40aa)

1 g of p-tolualdehyde (8.3 mM) and 4.16 g of triphenyl phosphanyliden-acetic acid methyl ester (12.45 mM) were dissolved in methylene chloride, the reaction solution was stirred at 90° C. for overnight. After the resluting mixture was concentrated under reduced pressure, a solvent mixture mixed with EtOAc and hexane (1:7) was added thereto with stirring for 1 hr. And then white solid was removed on filter, the residue was filtered and concentrated in vacuo to give 1.39 g of 3-p-tolyl-acrylic acid methyl ester (40aa) (yield: 95%).

Step 2. Preparation of 3-p-tolyl-propionic acid methyl ester (40ab)

1.39 g of 3-p-tolyl-acrylic acid methyl ester (40aa) prepared by above Step 1 was dissolved in methanol solution (7.9 mM) under nitrogen atmosphere. Then Pd—C was added thereto, hydrogenated under a hydrogen balloon for 1 to 2 hrs at room temperature. The reaction mixture was filtered and concentrated in vacuo. The resulting compound was purified with Silica gel column chromatography with a solvent mixture mixed with EtOAc and hexane (1:10) as an eluant to give 1.24 g of 3-p-tolyl-propionic acid methyl ester (40ab) (yield: 95%).

Step 3. Preparation of 3-p-tolyl-propane-1-ol (40ac)

1.24 g of 3-p-tolyl-propionic acid methyl ester (40ab) prepared by above Step 2 was dissolved in 100 ml of tetrahydrofuran under Ar atmosphere. Then 27 ml of lithium aluminium-hydride was added thereto with stirring for 2 hrs at 0° C. After 3 ml of distilled water, 3 ml of NaOH (1N) and 9 ml of distilled water were added to the reaction mixture sequentially, the mixture was stirred for 30 min and filtered using cellite in glass filter and concentrated in vacuo. The resultant was purified by Silica gel column chromatography with a solvent mixture mixed with methanol and chloroform (1:2) as an eluant to give 971 mg of 3-p-tolyl-propane-1-ol (40ac) (yield: 93%).

Step 4. Preparation of toluene-4-sulfonate-3-p-tolyl-propyl ester (40ad)

2.46 g of tosyl chloride (13 mM), 3.4 ml of diisopropylamine (19.4 mM) and 158 mg of 4-(dimethylamino)pyridine (1.29 mM) were added to reaction solution (6.46 mM) dissolving 971 mg of 3-p-tolyl-propane-1-ol (40ac) prepared by above step 3 in methylene chloride at 0° C. under Ar atmosphere with stirring for 6 hrs, and the reaction mixture was stirred for 12 hrs at room temperature. After the reaction mixture was neutralized with ammonium chloride, the mixture was extracted with ethyl acetate, washed with saturated NaCl solution, dried over MgSO$_4$, filtered, and concentrated in vacuo. The resultant was purified by Silica gel column chromatography with a solvent mixture mixed with methanol and chloroform (1:7) as an eluant to give 1.3 g of toluene-4-sulfonate-3-p-tolyl-propyl ester (40ad) (yield: 70%).

Step 5. Preparation of allyl-(3-p-tolyl-propyl)-amine (40ae)

1.6 ml of allylamine (21.4 mM) and 0.97 ml of diisopropyl ethylamine (5.5 mM) were added to the reaction solution (4.27 mM) containing 1.3 g of allyl-(3-p-tolyl-propyl)-amine (40ae) prepared by above Step 4 dissolved in acetonitrile solution with stirring for 6 hrs at 100° C. After the reaction mixture was neutralized with 10% NaOH solution, the mixture was extracted with chloroform, washed with saturated NaCl solution, dried over MgSO$_4$, filtered, and concentrated in vacuo. The resultant was purified by Silica gel column chromatography with a solvent mixture mixed with methanol and chloroform (1:9) as an eluant to give 687 mg of allyl-(3-p-tolyl-propyl)-amine (40ae) (yield: 85%).

Step 6. Preparation of 4-[allyl-(3-p-tolyl-propyl)-carbamoyl]-pent-4-enoic acid methyl ester (40af)

683 mg of 2-methylene-pentane dionate-5-methyl ester (4.3 mM), 902 mg of 143-(dimethylamino)propyl]-3-ethyl-carbodiimide (4.7 mM) and 133 mg of 4-(dimethylamino) pyridine (1.09 mM) were added to reaction solution (3.62 mM) dissolving 687 mg allyl-(3-p-tolyl-propyl)-amine (40ae) prepared by above step 5 in 0.5M of methylene chloride solution under Ar atmosphere and the mixture was stirred for 10 hrs at room temperature. After the resulting mixture was washed with 5% HCl solution (10 ml), the mixture was extracted with ethylacetate, washed with saturated NaCl. And then the extracts were washed with saturated 10 ml of NaHCO$_3$ solution and NaCl solution to separate into an organic layer and water layer. The organic layer was dried over anhydrous MgSO$_4$, filtered and concentrated in vacuo. The resultant was purified by Silica gel column chromatography with a solvent mixture mixed with EtOAc and hexanes (1:2) as an eluant to give 797 mg of 4-[allyl-(3-p-tolyl-propyl)-carbamoyl]-pent-4-enoic acid methyl ester (40af) (yield: 73%).

$^1$H-NMR (300 MHz, CDCl$_3$) δ 7.05 (s, 4H), 5.70 (s, 1H), 5.16-5.07 (m, 4H), 3.94 (s, 2H), 3.64 (t, J=3.3 Hz, 3H), 3.36 (s, 2H), 2.67-2.51 (m, 6H), 2.28 (s, 3H), 1.83 (t, J=7.7 Hz, 2H)

Step 7. Preparation of 3-[2-oxo-1-(3-p-tolyl-propyl)-2,5-dihydro-1H-pyrrol-3-yl]-propionic acid methyl ester (40ag)

797 mg of 4-[allyl-(3-p-tolyl-propyl)-carbamoyl]-pent-4-enoic acid methyl ester (40af) (2.6 mM) prepared by the above Step 6 was added to the catalyst solution containing 180 mg of ruthenium catalyst (0.1 mM) dissolved in 200 ml of CH$_2$Cl$_2$ under Ar atmosphere. Then the mixture was stirred for 24 hrs at room temperature, filtered and concentrated in vacuo. The resultant was purified by Silica gel column chromatography with a solvent mixture mixed with EtOAc and hexanes (1:1) as an eluant to give 391 mg of 3-[2-oxo-1-(3-p-tolyl-propyl)-2,5-dihydro-1H-pyrrol-3-yl]-propionic acid methyl ester (40ag) (yield: 50%).

$^1$H-NMR (300 MHz, CDCl$_3$) δ 6.96 (s, 4H), 6.56 (s, 1H), 3.67 (s, 2H), 3.55 (s, 3H), 3.37 (t, J=7.2 Hz, 2H), 2.48 (t, J=8.2 Hz, 6H), 2.19 (s, 3H), 1.76 (t, J=7.6 Hz, 2H)

Step 8. Preparation of N-hydroxy-3-[2-oxo-1-(3-p-tolyl-propyl)-2,5-dihydro-1H-pyrrol-3-yl]-propionamide (40ah)

100 mg of 3-[2-oxo-1-(3-p-tolyl-propyl)-2,5-dihydro-1H-pyrrol-3-yl]-propionic acid methyl ester (40ag) prepared by the above Step 7 was dissolved in methanol solution (0.33 mM) and then 1.7 M methanolic suspension solution containing NH$_2$OK (0.82 ml, 5.0 mM) was added thereto at 0° C. and the resulting mixture was stirred for 8 hrs at room temperature. The resulting mixture was neutralized with 0.02 ml of acetic acid, diluted with 10% methanol/chloroform solution, filtered and concentrated in vacuo. The resulting compound was purified by Silica gel column chromatography with a solvent mixture mixed with methanol and chloroform (1:9) as an eluant to give 50 mg of N-hydroxy-3-[2-oxo-1-(3-p-tolyl-propyl)-2,5-dihydro-1H-pyrrol-3-yl]-propionamide (40ah) (yield: 50%).
$^1$H-NMR (300 MHz, CDCl$_3$) δ 7.21 (s, 4H), 6.95 (s, 1H), 3.96 (s, 2H), 3.60 (s, 2H), 2.72 (s, 5H), 2.45 (s, 3H), 1.99 (s, 2H)

Example 41

Preparation of N-hydroxy-3-[2-oxo-1-(3-o-tolyl-propyl)-2,5-dihydro-1H-pyrrol-3-yl]-propionamide (41ah)

N-hydroxy-3-[2-oxo-1-(3-o-tolyl-propyl)-2,5-dihydro-1H-pyrrol-3-yl]-propionamide (41 ah) was prepared by the similar procedure described in above Example 40 (See Table 7).

Example 42

Preparation of N-hydroxy-3-[2-oxo-1-(3-m-tolyl-propyl)-2,5-dihydro-1H-pyrrol-3-yl]-propionamide (42ah)

N-hydroxy-3-[2-oxo-1-(3-m-tolyl-propyl)-2,5-dihydro-1H-pyrrol-3-yl]-propionamide (42ah) was prepared by the similar procedure described in above Example 40 (See Table 7).

Example 43

Preparation of N-hydroxy-3-{1-[3-(4-isopropyl-phenyl)-propyl]-2-oxo-2,5-dihydro-1H-pyrrol-3-yl]-propionamide (43ah)

N-hydroxy-3-{1-[3-(4-isopropyl-phenyl)-propyl]-2-oxo-2,5-dihydro-1H-pyrrol-3-yl]-propionamide (43ah) was prepared by the similar procedure described in above Example 40 (See Table 7).

Example 44

Preparation of 3-[1-[3-(4-bromo-phenyl)-propyl]-2-oxo-2,5-dihydro-1H-pyrrol-3-yl]-N-hydroxy-propionamide (44ah)

3-{1-[3-(4-bromo-phenyl)-propyl]-2-oxo-2,5-dihydro-1H-pyrrol-3-yl]-N-hydroxy-propionamide (44ah) was prepared by the similar procedure described in above Example 40 (See Table 7).

Example 45

Preparation of 3-[1-[3-(4-chloro-phenyl)-propyl]-2-oxo-2,5-dihydro-4H-pyrrol-3-yl]-N-hydroxy-propionamide (45ah)

3-{1-[3-(4-chloro-phenyl)-propyl]-2-oxo-2,5-dihydro-1H-pyrrol-3-yl]-N-hydroxy-propionamide (45ah) was prepared by the similar procedure described in above Example 40 (See Table 7).

Example 46

Preparation of N-hydroxy-3-{1-[3-(4-methoxy-phenyl)-propyl]-2-oxo-2,5-dihydro-1H-pyrrol-3-yl]-propionamide (46ah)

N-hydroxy-3-{1-[3-(4-methoxy-phenyl)-propyl]-2-oxo-2,5-dihydro-1H-pyrrol-3-yl]-propionamide (46ah) was prepared by the similar procedure described in above Example 40 (See Table 7).

Example 47

Preparation of N-hydroxy-3-{1-[3-(2-methoxy-phenyl)-propyl]-2-oxo-2,5-dihydro-1H-pyrrol-3-yl]-propionamide (47ah)

N-hydroxy-3-{1-[3-(2-methoxy-phenyl)-propyl]-2-oxo-2,5-dihydro-1H-pyrrol-3-yl]-propionamide (47ah) was prepared by the similar procedure described in above Example 40 (See Table 7).

Example 48

Preparation of N-hydroxy-3-{1-[3-(3-methoxy-phenyl)-propyl]-2-oxo-2,5-dihydro-1H-pyrrol-3-yl]-propionamide (48ah)

N-hydroxy-3-{1-[3-(3-methoxy-phenyl)-propyl]-2-oxo-2,5-dihydro-1H-pyrrol-3-yl]-propionamide (48ah) was prepared by the similar procedure described in above Example 40 (See Table 7).

TABLE 7

| Example | Chemical structure | NMR spectrum data |
|---|---|---|
| 41 | 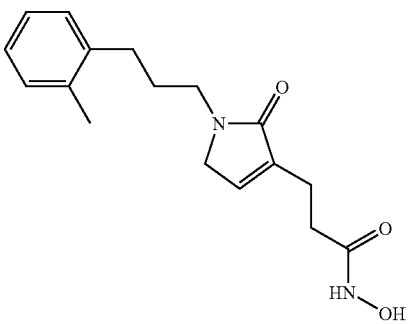 | 7.08 (d, J= 4.2 Hz, 4H), 6.69 (s, 1H), 3.80 (s, 2H), 3.48 (d, J= 6.6 Hz, 2H), 2.57 (d, J= 9.0 Hz, 6H), 2.25 (d, J= 6.3 Hz, 4H), 1.79 (s, 2H) |

TABLE 7-continued

| Example | Chemical structure | NMR spectrum data |
|---|---|---|
| 42 | 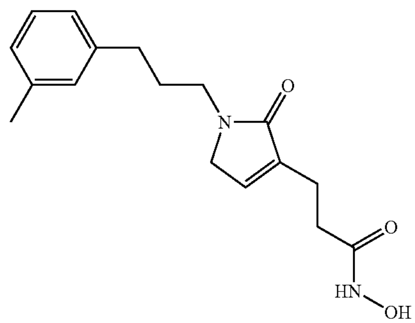 | 7.02–6.97 (m, 1H), 6.81 (d, J= 8.4 Hz, 3H), 6.64 (s, 1H), 4.07 (s, 2H), 3.71 (s, 2H), 3.32 (t, J= 7.4 Hz, 2H), 2.43 (t, J= 7.7 Hz, 5H), 2.17 (t, J= 6.5 Hz, 4H), 1.78–1.68 (m, 2H) |
| 43 | 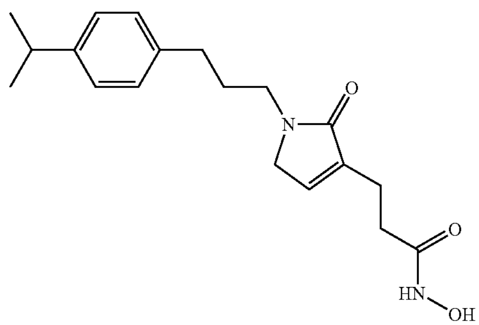 | 10.23 (s, 1H), 7.09 (dd, J= 6.0 Hz, 4H), 6.73 (s, 1H), 3.79 (s, 2H), 3.45 (t, J= 5.1 Hz, 2H), 2.87–2.80 (m, 1H), 2.61 (s, 1H), 2.56 (t, J= 5.9 Hz, 2H), 2.46 (s, 2H), 1.88–1.81 (m, 2H), 1.26–1.19 (m, 6H) |
| 44 | 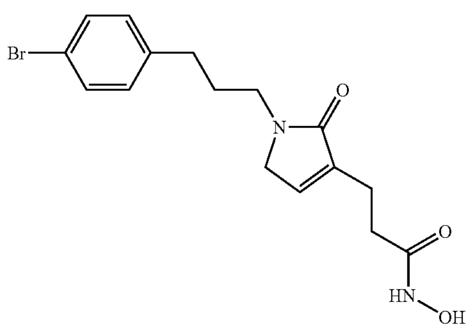 | 7.23 (t, J= 5.5 Hz, 1H), 7.14 (t, J= 5.5 Hz, 3H), 6.73 (s, 1H), 3.77 (s, 1H), 3.43 (t, J= 5.0 Hz, 2H), 2.58 (t, J= 5.7 Hz, 4H), 2.45 (s, 2H), 188–1.81 (m, 2H) |
| 45 | 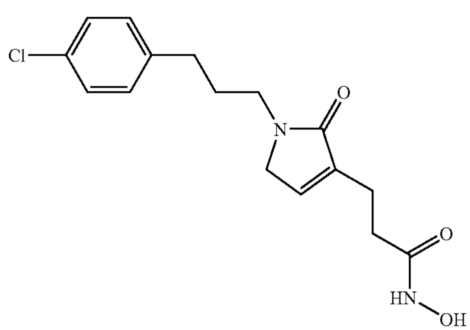 | 7.23–7.04 (m, 4H), 6.73 (s, 1H), 3.77 (s, 2H), 3.43 (t, J= 5.7 Hz, 2H), 2.56 (t, J= 12.9 Hz, 3H), 2.42 (s, 2H), 1.83 (t, J= 6.7 Hz, 2H) |

TABLE 7-continued

| Example | Chemical structure | NMR spectrum data |
|---|---|---|
| 46 | 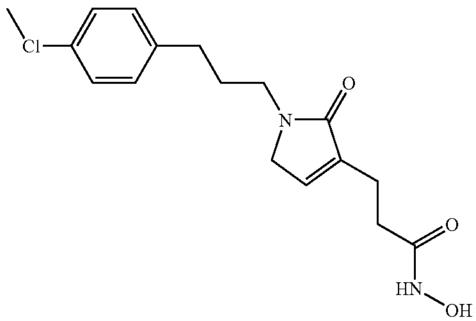 | 7.03 (d, J= 8.7 Hz, 2H), 6.79–6.75 (m, 2H), 6.72 (s, 1H), 3.72 (d, J= 9.9 Hz, 5H), 3.40 (t, J= 7.3 Hz, 2H), 2.58–2.42 (m, 6H), 1.78 (t, J= 7.4 Hz, 2H) |
| 47 | 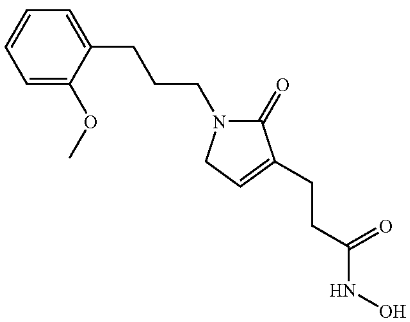 | 7.16–7.06 (m, 2H), 6.84–6.67 (m, 3H), 3.79 (t, J= 5.5 Hz, 2H), 3.75 (t, J= 3.4 Hz, 3H), 3.50–3.41 (m, 2H), 2.55 (t, J= 7.7 Hz, 3H), 2.43 (s, 1H), 1.87 (s, 2H), 1.84–1.77 (m, 2H) |
| 48 | 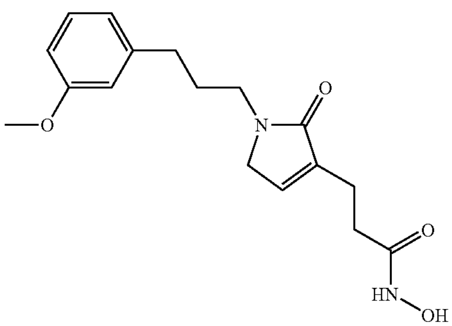 | 7.19–7.10 (m, 1H), 6.71 (d, J= 10.8 Hz, 4H), 3.75 (S, 5H), 3.49–3.40 (m, 2H), 2.55 (t, J= 7.7 Hz, 4H), 2.43 (s, 2H), 1.88–1.84 (m, 2H) |

Example 49

Preparation of N-hydroxy-3-(1-naphthalene-2-ylmethyl)-2-oxo-2,5-dihydro-1H-pyrrol-3-yl)-propionamide (1e')

N-hydroxy-3-(1-naphthalene-2-ylmethyl-2-oxo-2,5-dihydro-1H-pyrrol-3-yl)-propionamide (1e') was prepared by the similar procedure described in above Example 1 (See Table 8).

TABLE 8

| Example | Chemical structure | NMR spectrum or LC-MS data |
|---|---|---|
| 49 | 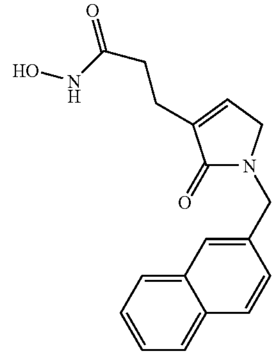 | RT: 3.93–5.93 (Mass: 311.2) |

Example 50

Preparation of N-hydroxy-3-(1-methyl-2-oxo-2,5-dihydro-1H-pyrrol-3-yl)-propionamide (2h')

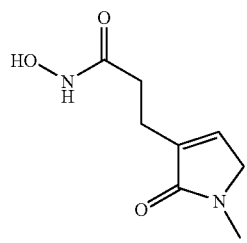

Step 1. Preparation of 3-(2-oxo-2,5-dihydro-1H-pyrrol-3-yl)-propionic acid methyl ester (2f)

0.1 ml of triethylsilane (0.63 mM) was added to the reaction solution containing 200 mg of 3-[1-(2,4-dimethoxybenzyl)-2-oxo-2,5-dihydro-1H-pyrrol-3-yl]-propionic acid methyl ester (0.63 mM) dissolved in 0.7 ml of trifluoroacetic acid solution at 0° C. After the reaction mixture was heated for 1 hr, the mixture was filtered and concentrated in vacuo to remove solvent. Then the resulting mixture was dissolved in 20 ml of chloroform solution to separate into an organic layer and water layer. The organic layer was washed with 5 ml of saturated NaHCO$_3$ solution and 5 ml of saturated NaCl solution, dried over anhydrous MgSO$_4$, filtered and concentrated in vacuo. The resultant was purified by Silica gel column chromatography with a solvent mixture mixed with EtOAc and hexanes (19:1) as an eluant to give 50 mg of 3-(2-oxo-2,5-dihydro-1H-pyrrol-3-yl)-propionic acid methyl ester (20 (yield: 47%).

$^1$H-NMR (300 MHz, CDCl$_3$) δ 6.76 (br t, 1H), 3.89 (d, J=1.3 Hz, 2H), 3.63 (t, J=1.9 Hz, 3H), 2.58 (s, 4H)

Step 2. Preparation of 3-(1-methyl-2-oxo-2,5-dihydro-1H-pyrrol-3-yl)-propionic acid methyl ester (2g)

0.33 ml of NaHMDS solution (1.0 M in THF, 0.33 mM) was added to 0.6 ml of THF solution containing 50 mg of 3-(2-oxo-2,5-dihydro-1H-pyrrol-3-yl)-propionic acid methyl ester (20 (0.295 mM) prepared by the Step 1 in a dropwise manner at −79° C. and stirred for 30 mins. After 0.3 ml of dimethyl sulfate 0.359 mM) was added thereto, the reaction mixture was stirred for 4 hrs at 0° C. Then the resulting mixture was dissolved in 2 ml of saturated NH$_4$Cl solution and extracted with 7 ml of ethyl acetate to separate into an organic layer and water layer. The organic layer was washed with 2 ml of saturated NaHCO$_3$ solution and 2 ml of saturated NaCl solution, dried over anhydrous MgSO$_4$, filtered and concentrated in vacuo. The resultant was purified by Silica gel column chromatography with EtOAc as an eluant to give 18 mg of 3-(1-methyl-2-oxo-2,5-dihydro-1H-pyrrol-3-yl)-propionic acid methyl ester (2g) (yield: 33%).

$^1$H-NMR (300 MHz, CDCl$_3$) δ 6.65 (br t, 1H), 3.81 (s, 1H), 3.64 (s, 3H), 3.01 (s, 3H), 2.60 (t, 4H).

Step 3. Preparation of N-hydroxy-3-(1-methyl-2-oxo-2,5-dihydro-1H-pyrrol-3-yl)-propionamide (2h)

18 mg of 3-(1-methyl-2-oxo-2,5-dihydro-1H-pyrrol-3-yl)-propionic acid methyl ester (2g) prepared by the above Step 2 was dissolved in methanol solution (0.1 mM) and then 1.7 M methanolic suspension solution containing NH$_2$OK (0.09 ml, 0.15 mM) was added thereto at 0° C. and the resulting mixture was stirred for 1 hr at room temperature. The resulting mixture was neutralized with 0.03 ml of acetic acid, diluted with 10% methanol/chloroform solution, filtered and concentrated in vacuo. The resulting compound was purified by Silica gel column chromatography with a solvent mixture mixed with EtOAc and methanol (5:2) as an eluant to give 11 mg of N-hydroxy-3-(1-methyl-2-oxo-2,5-dihydro-1H-pyrrol-3-yl)-propionamide (2h) (yield: 59%).

$^1$H-NMR (300 MHz, CDCl$_3$) δ 6.76 (br t, 1H), 3.84 (s, 2H), 3.00 (s, 3H), 2.59 (t, J=7.2 Hz, 2H), 2.42 (t, J=7.2 Hz, 2H)

Example 51

Preparation of 3-(1-allyl-2-oxo-2,5-dihydro-1H-pyrrol-3-yl)-N-hydroxy-propionamide (3h')

3-(1-allyl-2-oxo-2,5-dihydro-1H-pyrrol-3-yl)-N-hydroxy-propionamide (3h') was prepared by the similar procedure described in above Example 50 (See Table 9).

TABLE 9

| Example | Chemical structure | NMR spectrum data |
|---|---|---|
| 51 | 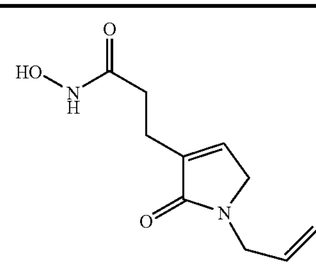 | 6.89 (br t, 1H), 5.98-5.67 (m, 2H), 5.10–5.08 (m, 1H), 3.36 (t, J= 1.8 Hz, 2H), 2.61 (s, 2H), 2.06 (s, 2H), 1.87 (s, 2H) |

Example 52

Preparation of N-hydroxy-3-[1-(2-naphthalene-1-yl-ethyl)-2-oxo-2,5-dihydro-1H-pyrrol-3-yl]-propionamide (4n')

N-hydroxy-3-[1-(2-naphthalene-1-yl-ethyl)-2-oxo-2,5-dihydro-1H-pyrrol-3-yl]-propionamide (4n') was prepared by the similar procedure described in above Example 28 (See Table 10).

Example 53

Preparation of N-hydroxy-3-[1-(2-naphthalene-2-yl-ethyl)-2-oxo-2,5-dihydro-1H-pyrrol-3-yl]-propionamide (5n')

N-hydroxy-3-[1-(2-naphthalene-2-yl-ethyl)-2-oxo-2,5-dihydro-1H-pyrrol-3-yl]-propionamide (5n') was prepared by the similar procedure described in above Example 28 (See Table 10).

Example 54

Preparation of N-hydroxy-3-[2-oxo-1-(2-thiophen-2-yl-ethyl)-2,5-dihydro-4H-pyrrol-3-yl]-propionamide (6n')

N-hydroxy-3-[2-oxo-1-(2-thiophen-2-yl-ethyl)-2,5-dihydro-1H-pyrrol-3-yl]-propionamide (6n') was prepared by the similar procedure described in above Example 28 (See Table 10).

Example 55

Preparation of 3-[1-(3-biphenyl-4-yl-propyl)-2-oxo-2,5-dihydro-1H-pyrrol-3-yl]-N-hydroxy-propionamide (7w')

3-[1-(3-biphenyl-4-yl-propyl)-2-oxo-2,5-dihydro-1H-pyrrol-3-yl]-N-hydroxy-propionamide (7w') was prepared by the similar procedure described in above Example 40 (See Table 11).

Example 56

Preparation of N-hydroxy-3-[1-(3-naphthalene-2-yl-propyl)-2-oxo-2,5-dihydro-1H-pyrrol-3-yl]-propionamide (8w')

N-hydroxy-3-[1-(3-naphthalene-2-yl-propyl)-2-oxo-2,5-dihydro-1H-pyrrol-3-yl]-propionamide (8w') was prepared by the similar procedure described in above Example 40 (See Table 11).

TABLE 10

| Example | Chemical structure | NMR spectrum data |
|---|---|---|
| 52 | 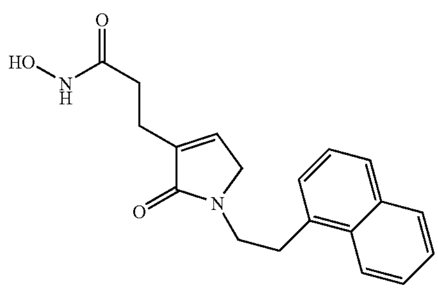 | 8.01(d, J= 8.1 Hz, 1H), 7.77(d, J= 8.7 Hz, 1H), 7.66 (d, J= 8.1 Hz, 1H), 7.48–7.20 (m, 3.30–3.25(m, 2H), 2.51 (t, J= 7.3 Hz, 2H), 2.25 (t, J= 7.3 Hz, 2H) |
| 53 | 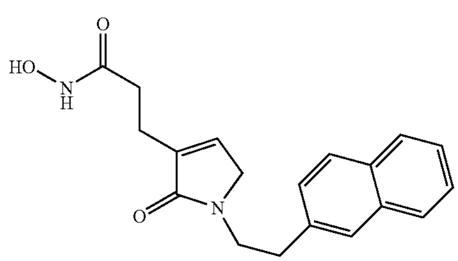 | 7.73–7.66 (m, 3H), 7.53 (s, 1H), 7.40–7.32 (m, 2H), 7.22 (s, 1H), 6.61 (br t, 1H), 3.69 (t, J= 7.3 Hz, 2H), 3.60 (s, 2H), 2.97 (t, J= 7.0 Hz, 2H), 2.49 (t, J= 7.2 Hz, 2H), 2.24 (t, J= 7.3 Hz, 2H) |
| 54 | 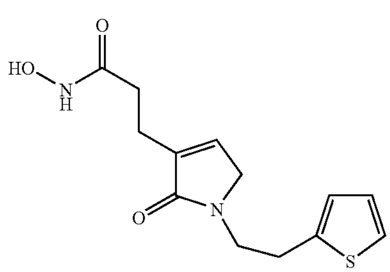 | 7.08 (br t, 1H), 6.85 (t, J= 4.0 Hz, 1H), 6.74 (s, 1H), 6.68 (br t, 1H), 3.65 (s, 4H), 3.37–3.29 (m, 1H), 3.05 (t, J= 6.1 Hz, 2H), 2.51 (d, J= 4.8 Hz, 2H), 2.28 (s, 1H) |

TABLE 11

| Example | Chemical structure | NMR spectrum data |
|---|---|---|
| 55 | 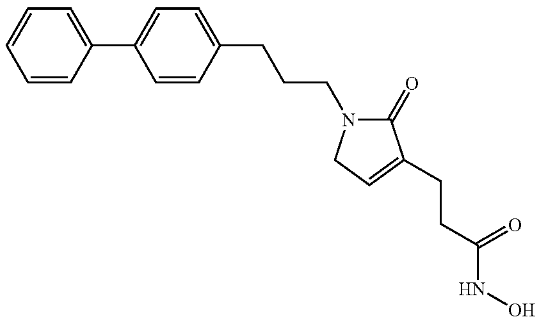 | 7.51 (dd, J= 8.0 Hz, 4H), 7.37 (t, J= 7.4 Hz, 2H), 7.26 (q, J= 7.2 Hz, 3H), 6.81 (s, 1H), 4.79 (s, 2H), 3.89 (s, 2H), 3.48 (t, J= 7.1 Hz, 2H), 2.64 (t, J= 7.7 Hz, 2H), 2.56 (t, J= 5.1 Hz, 2H), 2.32 (t, J= 6.9 Hz, 1H) |
| 56 | 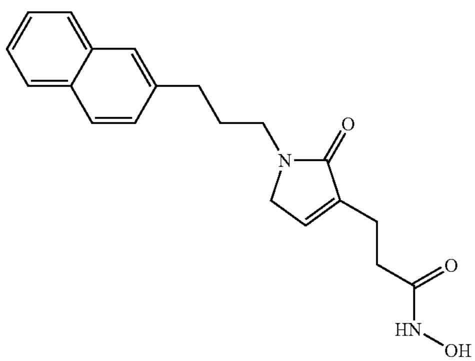 | 10.54 (s, 1H), 7.71 (dd, J= 7.9 Hz, 3H), 7.54 (s, 1H), 7.41–7.33 (m, 2H), 7.24(d, J= 7.8 Hz, 1H), 6.64 (s, 1H), 3.67 (s, 2H), 3.40 (s, 2H), 2.69 (t, J= 6.7 Hz, 2H), 2.57 (s, 2H), 2.41 (s, 2H), 1.86 (s, 2H) |

Example 57

Preparation of 3-[1-(2,4-Dimethoxybenzyl)-2-oxo-1, 2,5,6-tetrahydropyridin-3-yl]N-hydroxypropionamide (e1)

Step 1. Preparation of But-3-enyl-(2,4-dimethoxybenzyl)amine (b)

0.5 ml of 1-Bromo-3-butene (4.926 mM) and 0.94 ml of diisopropyl ethylamine (5.396 mM) were added to the reaction solution containing 0.74 ml of 2,4-dimethoxybenzylamine (a) (4.926 mM) dissolved in methylene chloride with stirring and the solution was left alone at room temperature for overnight. The reaction mixture was washed with saturated NaCl solution, dried over MgSO$_4$, filtered and concentrated in vacuo. The resulting compound was purified with Silica gel column chromatography with EtOAc solvent as an eluant to give 436 mg of the pure title compound (b) (yield: 40%).

$^1$H-NMR (300 MHz, CDCl$_3$) δ 7.10 (d, J=8.1 Hz, 1H), 6.41 (m, 2H), 5.75 (m, 1H), 5.01 (m, 2H), 3.78 (s, 3H), 3.77 (s, 3H), 3.70 (s, 2H), 2.63 (t, J=7.5 Hz, 2H), 2.24 (m, 2H)

Step 2. Preparation of 4-[But-3-enyl-(2,4-dimethoxybenzyl)-carbamoyl]-pent-4-enoic acid methyl ester (c)

714 mg of 2-methylene-pentane dionate-5-methyl ester (4.519 mM), 953 mg of EDC (4.971 mM) and 110 mg of DMAP (0.9 mM) were added to 0.5 M of reaction solution dissolving the compound (b) prepared by above step 1 in methylene chloride and the mixture was stirred for 5 hrs at room temperature. The resulting mixture was diluted with ethyl acetate and washed with 5% HCl solution (10 ml) and 10 ml of sat. NaHCO$_3$ solution to separate into an organic layer and water layer. The organic layer was dried over anhydrous MgSO$_4$, filtered and concentrated in vacuo. The resultant was purified by Silica gel column chromatography with a solvent mixture mixed with EtOAc and hexanes (1:2) as an eluant to give 1.39 g of 4-[but-3-enyl-(2,4-dimethoxybenzyl)-carbamoyl]-pent-4-enoic acid methyl ester (c) (yield: 40%).

Step 3. Preparation of 3-[1-(2,4-dimethoxybenzyl)-2-oxo-1,2,5,6-tetrahydro-pyridin-3-yl]-propionic acid methyl ester (d)

130 mg of the compound (c) (0.360 mM) prepared by the above Step 2 was added to the catalyst solution containing 20 mg of ruthenium (0.024 mM) dissolved in CH$_2$Cl$_2$. Then the mixture was stirred for 24 hrs at room temperature, filtered and concentrated in vacuo. The resultant was purified by Silica gel column chromatography with methanol/chloroform (1:10) solvent mixture as an eluant to give 108 mg of the title compound (d) (yield: 90%).

$^1$H-NMR (300 MHz, CDCl$_3$) δ 7.17 (d, J=8.9 Hz, 1H), 6.41 (m, 2H), 6.26 (t, J=4.3 Hz, 1H), 4.53 (s, 2H), 3.77 (s, 3H), 3.76 (s, 3H), 3.62 (s, 3H), 3.28 (t, J=7.1 Hz, 2H), 2.61-2.47 (m, 4H), 2.22 (m, 2H)

$^{13}$C-NMR (75 MHz, CDCl$_3$) δ 173.6, 164.8, 160.2, 158.5, 134.2, 133.9, 130.4, 118.0, 104.1, 98.3, 55.2, 51.3, 45.0, 44.3, 33.3, 26.6, 23.9

Step 4. Preparation of 3-[1-(2,4-dimethoxybenzyl)-2-oxo-1,2,5,6-tetrahydro-pyridin-3-yl]-N-hydroxy-propionamide (e1)

46 mg of compound (d) prepared by the above Step 3 was dissolved in methanol solution (0.138 mM) and then 1.7 M methanolic suspension solution containing NH$_2$OK (0.122 ml, 0.207 mM) was added thereto at 0° C. and the resulting mixture was stirred for 3 hrs at room temperature. The resulting mixture was neutralized with 0.02 ml of acetic acid, diluted with 10 ml of ethyl acetate solution, filtered and concentrated in vacuo. The resulting compound was purified by column chromatography on Silica gel with methanol/chloroform (1:10) solvent mixture as an eluant to give 32 mg of the title compound (e1) (yield: 73%).

$^1$H-NMR (300 MHz, CDCl$_3$) δ 7.122 (d, J=9.0 Hz, 1H), 6.415-6.331 (m, 3H), 4.505 (s, 2H), 3.750 (s, 3H), 3.744 (s, 3H), 3.271 (t, J=6.9 Hz, 2H), 2.552 (m, 2H), 2.381 (m, 2H), 2.220 (m, 2H)

$^{13}$C-NMR (75 MHz, CDCl$_3$) δ 170.1, 165.4, 160.2, 158.5, 135.8, 133.5, 130.4, 117.5, 104.2, 98.3, 55.3, 44.9, 44.6, 32.8, 27.1, 23.8

Example 58

Preparation of N-hydroxy-3-(1-benzyl-2-oxo-1,2,5,6-tetrahydro-pyridin-3-yl)-propionic acid (e2)

N-hydroxy-3-(1-benzyl-2-oxo-1,2,5,6-tetrahydro-pyridin-3-yl)-propionic acid (e2) was prepared by the similar procedure described in above Example 57 (See Table 12).

Example 59

Preparation of N-hydroxy-3-[1-(4-nitro-benzyl)-2-oxo-1,2,5,6-tetrahydro-pyridin-3-yl)-propionamide (e3)

N-hydroxy-3-[1-(4-nitro-benzyl)-2-oxo-1,2,5,6-tetrahydro-pyridin-3-yl)-propionamide (e3) was prepared by the similar procedure described in above Example 57 (See Table 12).

Example 60

Preparation of 3-(1-benzyl-2-oxo-1,2,5,6-tetrahydro-pyridin-3-yl)-N-hydroxy propionamide (e4)

3-(1-benzyl-2-oxo-1,2,5,6-tetrahydro-pyridin-3-yl)-N-hydroxy propionamide (e4) was prepared by the similar procedure described in above Example 57 (See Table 12).

Example 61

Preparation of N-hydroxy-3-[2-oxo-1-(4-phenyl-butyl)-1,2,5,6-tetrahydro-pyridin-3-yl]-propionamide (e5)

N-hydroxy-3-[2-oxo-1-(4-phenyl-butyl)-1,2,5,6-tetrahydro-pyridin-3-yl]-propionamide (e5) was prepared by the similar procedure described in above Example 57 (See Table 12).

Example 62

Preparation of N-hydroxy-3-(2-oxo-1-phenethyl-1,2,5,6-tetrahydro-pyridin-3-yl)-propionamide (e6)

N-hydroxy-3-(2-oxo-1-phenethyl-1,2,5,6-tetrahydro-pyridin-3-yl)-propionamide (e6) was prepared by the similar procedure described in above Example 57 (See Table 12).

TABLE 12

| Example | Chemical structure | NMR spectrum data |
|---|---|---|
| 58 | 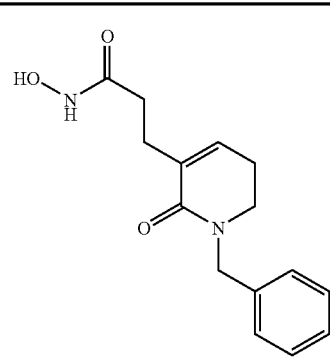 | 7.28(m, 5H), 6.44(t, J=4.3 Hz, 1H), 4.61(s, 2H), 3.33(m, 2H), 2.57(t, J=7.5 Hz, 2H), 2.28(m, 4H) |

TABLE 12-continued
| Example | Chemical structure | NMR spectrum data |
| --- | --- | --- |
| 59 | 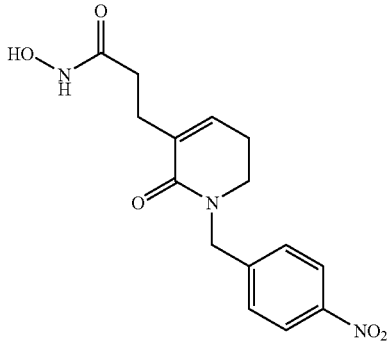 | 8.14(d, J=8.4 Hz, 2H), 7.40(t, J=7.2 Hz 2H), 6.42(br t 1H), 4.67(s, 2H(, 3.32(t, J=6.3 Hz, 2H), 2.67–2.32(m, 6H) |
| 60 | 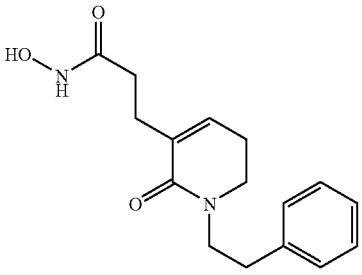 | 7.29–7.18(m, 5H) 6.40(br t 1H), 3.62(t, J=7.2 Hz 2H), 3.19(t, J=7.1 Hz 2H), 2.85(t, J=7.1 Hz 2H), 2.54–2.44(m 2H), 2.18–2.15(m 4H) |
| 61 | 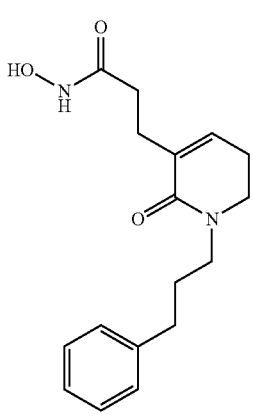 | 7.24–7.11(m, 5H), 6.31(br t, 1H), 3.35(br t, 2H), 3.23(br t, 2H), 2.55(d, J=6.6 Hz, 4H), 2.33(s, 2H), 2.18(s, 2H), 1.80(br t, 2H) |
| 62 | 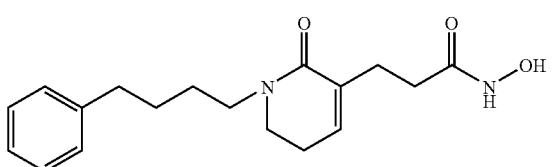 | 7.28–7.13(m, 5H), 6.36(t, J=3.9, 1H), 3.39(t, J=6.75, 2H), 3.29(t, J=7.05, 2H), 2.62(t, J=7.05, 2H), 2.54(t, J=6.75, 2H) 2.40(t, J=6.75, 2H), 2.27(ab, J=6.0, 5.4, 2H), 1.58(t, J=2.7, 4H) |

Example 63

Preparation of 3-[1-(2,4-dimethoxybenzyl)-2-oxo-1,2,5,6-tetrahydro-pyridin-3-yl)-propionic acid (f1)

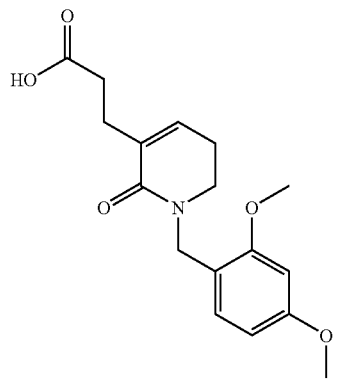

11 mg of LiOH.H$_2$O solution (0.262 mM) was added to 0.75 ml of THF solution containing 58 mg of 3-[1-(2,4-dimethoxy benzyl)-2-oxo-1,2,5,6-tetrahydro pyridine-3-yl]-propionic acid methyl ester (d) (0.174 mM) in a dropwise manner at 0° C. After the reaction mixture was stirred for 2 hrs at 0° C. and for 1 hr at room temperature, 5% HCl was added to the mixture to pH 2. Then the mixture was extracted three times with 10 ml of ethyl acetate, the organic layer was washed with saturated NaCl solution, dried over anhydrous MgSO$_4$, filtered and concentrated in vacuo. The resulting compound was purified with Silica gel column chromatography with methanol/chloroform (1:10) solvent mixture as an eluant to give 44 mg of the title compound (f1) (yield: 80%).

$^1$H-NMR (300 MHz, CDCl$_3$) δ 7.16 (d, J=8.9 Hz, 1H), 6.42 (m, 2H), 6.29 (t, J=4.3 Hz, 1H), 4.54 (s, 2H), 3.76 (s, 3H), 3.76 (s, 3H), 3.29 (t, J=7.2 Hz, 2H), 2.56 (m, 4H), 2.22 (m, 2H)

$^{13}$C-NMR (75 MHz, CDCl$_3$) δ 177.7, 165.1, 160.1, 158.5, 134.6, 133.9, 130.5, 117.7, 104.1, 98.3, 55.2, 44.9, 44.5, 33.5, 26.3, 23.8

Example 64

Preparation of 3-(1-benzyl-2-oxo-1,2,5,6-tetrahydro-pyridin-3-yl)-propionic acid (f2)

3-(1-benzyl-2-oxo-1,2,5,6-tetrahydro-pyridin-3-yl)-propionic acid (f2) was prepared by the similar procedure described in above Example 63 (See Table 13).

Example 65

Preparation of 3-[1-(4-nitro-benzyl)-2-oxo-1,2,5,6-tetrahydro-pyridin-3-yl)-propionic acid (f3)

3-[1-(4-nitro-benzyl)-2-oxo-1,2,5,6-tetrahydro-pyridin-3-yl)-propionic acid (f3) was prepared by the similar procedure described in above Example 63 (See Table 13).

Example 66

Preparation of 3-[2-oxo-1-(3-phenyl-propyl)-1,2,5,6-tetrahydro-pyridin-3-yl)-propionic acid (f4)

3-[2-oxo-1-(3-phenyl-propyl)-1,2,5,6-tetrahydro-pyridin-3-yl)-propionic acid (f4) was prepared by the similar procedure described in above Example 63 (See Table 13).

Example 67

Preparation of 3-[2-oxo-1-(4-phenyl-butyl)-1,2,5,6-tetrahydro-pyridin-3-yl)-propionic acid (f5)

3-[2-oxo-1-(4-phenyl-butyl)-1,2,5,6-tetrahydro-pyridin-3-yl)-propionic acid (f5) was prepared by the similar procedure described in above Example 63 (See Table 13).

Example 68

Preparation of 3-(2-oxo-1-phenethyl-1,2,5,6-tetrahydro-pyridin-3-yl)-propionic acid (f6)

3-(2-oxo-1-phenethyl-1,2,5,6-tetrahydro-pyridin-3-yl)-propionic acid (f6) was prepared by the similar procedure described in above Example 63 (See Table 13).

TABLE 13

| Example | Chemical structure | NMR spectrum data |
| --- | --- | --- |
| 64 | 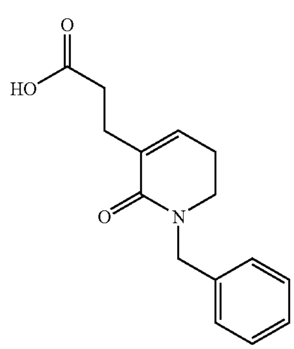 | 7.25(m, 5H), 6.34(t, J=4.2 Hz, 1H), 4.60(s, 2H), 3.26(t, J=7.1 Hz, 2H), 2.59(m, 4H), 2.25(m, 2H) |

TABLE 13-continued
| Example | Chemical structure | NMR spectrum data |
|---|---|---|
| 65 | 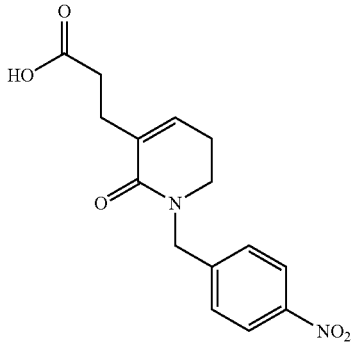 | 8.16(d J=8.7 Hz 2H), 7.42(d, J=8.6 Hz, 2H), 6.39(t, J=4.3Hz, 1H) 4.69(s, 2H) 3.32(t, J=7.2 Hz, 2H) 2.64–2.53(m, 4H), 2.33(dd J=6.9 Hz, 5.7 Hz, 2H) |
| 66 | 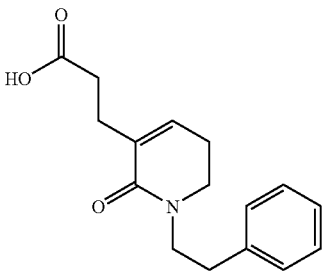 | 9.92(br s 1H), 7.28–7.15(m, 5H), 6.28(t J=4.4, 1H), 3.60(t, J=7.4, 2H) 3.16(t, J=7.2, 2H), 2.84(t, J=7.4, 2H) 2.58–2.48 (m, 4H) 2.15(AB, J=11.4, 6.8, 2H) |
| 67 | 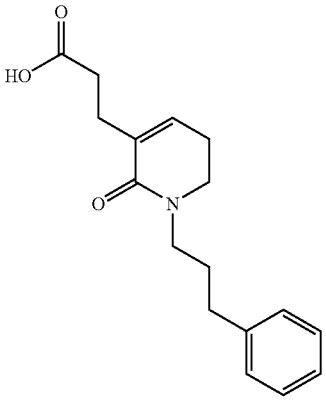 | 7.28–7.10(m, 5H), 6.28(br t, 1H), 5.75–5.60(m, 1H), 5.01(d, J=16.5 Hz, 2H), 3.41–3.26(m, 3H) 2.63–2.26(m, 7H) 1.84(t, J=6.8 Hz, 2H) |
| 68 | 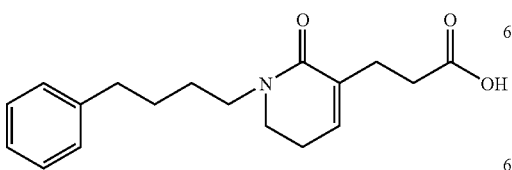 | 7.256–7.138(m, 5H), 6.33(br t, 1H), 3.42(t, J=6.9, 2H), 3.32(t, J=7.35, 2H), 2.63(t, J=7.05, 2H), 2.547(d, J=2.4, 4H), 2.30(d, J=4.5, 2H), 1.61(q, J=1.5, 4H) |

Example 69

Preparation of 3-(1-benzyl-2-oxo-1,2,5,6-tetrahydro-pyridin-3-yl)-N-pyridin-2-yl-propionamide (g1)

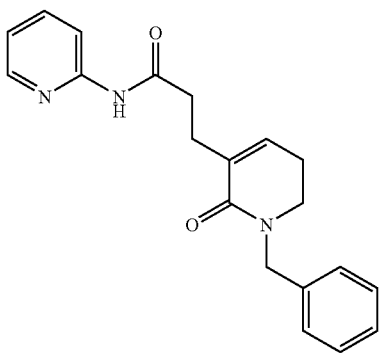

Pyridyl amine was added to organic solvent dissolving 30 mg of 3-(1-benzyl-2-oxo-1,2,5,6-tetrahydro-pyridin-3-yl)-propionic acid (0.12 mM) in EDC. The resulting compound was purified by Silica gel column chromatography with methanol/chloroform (1:20) solvent mixture as an eluant to give 16 mg of the title compound (g1) (yield: 39%).

Example 70

Preparation of N-(2-amino-phenyl)-3-(1-benzyl-2-oxo-1,2,5,6-tetrahydro-pyridin-3-yl)-propionamide (g2)

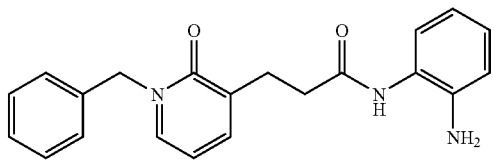

40 mg of 1,2-phenylenediamine (0.37 M), 77 mg of EDC (0.4 M) and 1 mg of DMAP (3 M %) were added to reaction solution dissolving 3-(1-benzyl-2-oxo-1,2,5,6-tetrahydro-pyridin-3-yl)-propionic acid prepared by above Example 8 in 1 ml of methylene chloride under Argon atmosphere. After the mixture was stirred for 13 hrs at room temperature, the resulting mixture was diluted with ethyl acetate and washed with 10% NaOH solution (10 ml). Then the residue was extracted with 50 ml of chloroform, dried over anhydrous MgSO$_4$, filtered and concentrated in vacuo. The resultant was purified by Silica gel column chromatography with a solvent mixture mixed with methanol and chloroform (1:20) as an eluant to give 96 mg of N-(2-amino-phenyl)-3-(1-benzyl-2-oxo-1,2,5,6-tetrahydro-pyridin-3-yl)-propionamide (g2) (yield: 91%).

$^1$H-NMR (300 MHz, CDCl$_3$) δ 8.29 (s, 1H), 7.29-7.19 (m, 5H), 7.13 (d, 1H, J=7.8 Hz), 6.99-6.94 (m, 1H), 6.68 (t, 2H, J=7.9 Hz), 6.37 (t, 1H, J=8.4 Hz), 4.57 (t, 2H, J=7.4 Hz), 3.88 (s, 2H), 3.29-3.21 (m, 2H), 2.68 (t, 2H, J=6.5 Hz), 2.59 (t, 2H, 6.5 Hz), 2.26-2.217 (m, 2H)

Example 71

Preparation of N-(2-amino-phenyl)-3-[1-(2-methyl-benzyl)-2-oxo-1,2,5,6-tetrahydro-pyridin-3-yl)-propionamide (g3)

N-(2-amino-phenyl)-3-[1-(2-methyl-benzyl)-2-oxo-1,2,5,6-tetrahydro-pyridin-3-yl)-propionamide (g3) was prepared by the similar procedure described in above Example 69 and 70 (See Table 14).

Example 72

Preparation of N-(2-amino-phenyl)-3-[1-(2-methyl-benzyl)-2-oxo-1,2,5,6-tetrahydro-pyridin-3-yl)-propionamide (g4)

N-(2-amino-phenyl)-3-[1-(2-methyl-benzyl)-2-oxo-1,2,5,6-tetrahydro-pyridin-3-yl)-propionamide (g4) was prepared by the similar procedure described in above Example 69 and 70 (See Table 14).

TABLE 14

| Example | Chemical structure | NMR spectrum data |
|---|---|---|
| 71 | 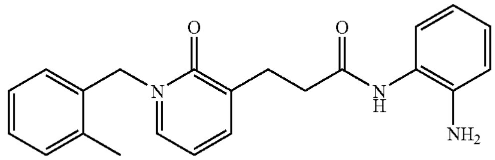 | 8.23(s, 1H), 7.12(dd, 5H, J=6.6 Hz), 6.979(t, 1H, J=7.5 Hz), 6.697(t, 2H, J=8.9 Hz), 6.408(t, 1H, J=7.4 Hz), 4.602(s, 2H), 3.874(s, 2H), 3.239(t, 2H, J=7.1 Hz), 2.702(t, 2H, J=6.8 Hz), 2.604(t, 2H, J=6.3 Hz), 2.260(t, 5H, J=6.3 Hz) |
| 72 | 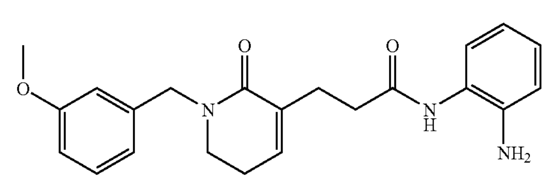 | 8.305(s, 1H), 7.189–7.091(m, 2H), 6.969–6.914(m, 2H), 6.794–6.741(m, 3H), 6.691–6.631(m, 2H), 6.355(t, 1H, J=4.1 Hz), 4.539(s, 2H) 3.965(s, 2H), 3.707(s, 3H), 3.253(t, 2H, J=7.0 Hz), 2.661–2.539(m, 4H), 2.22(dd, 2H, J=7.1 Hz) |

Example 73

Preparation of N-benzyloxy-3-(2-oxo-1-phenethyl-1,2,5,6-tetrahydro-pyridin-3-yl)-propionamide (g5)

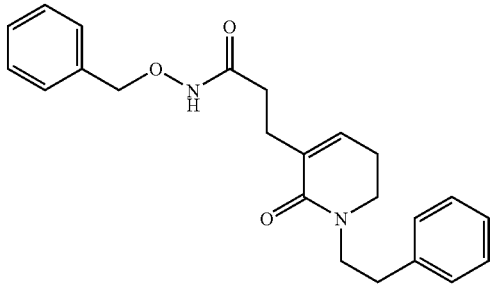

Benzyloxyamine was added to organic solvent dissolving 30 mg of 3-(1-benzyl-2-oxo-1,2,5,6-tetrahydro-pyridin-3-yl)-propionic acid (0.15 mM) prepared by above Example 12 in EDC. The resulting compound was purified by Silica gel column chromatography with ethylacetate/chloroform (1:1) solvent mixture as an eluant to give 41 mg of N-benzyloxy-3-(2-oxo-1-phenethyl-1,2,5,6-tetrahydro-pyridin-3-yl)-propionamide (g5) (yield: 75%).

$^1$H-NMR (300 MHz, CDCl$_3$) δ 7.41-7.15 (m, 1H), 6.34 (br t, 1H), 4.88 (s, 2H), 3.58 (t, J=7.4 Hz, 2H), 3.16 (t, J=7.2 Hz, 2H), 2.82 (t, J=7.2 Hz, 2H), 2.53 (t, J=6.8 Hz, 2H), 2.26 (br s, 1H), 2.19 (dd, J=11.4, 7.1 Hz, 2H)

Example 18

Preparation of 3-[1-(4-acetylamino-benzyl)-2-oxo-1,2,5,6-tetrahydro-pyridin-3-yl)-N-hydroxy-propionamide (j1)

Step 1. Preparation of 3-[1-(4-amino-benzyl)-2-oxo-1,2,5,6-tetrahydro-pyridin-3-yl]-propionic acid methyl ester (h)

50 mg of 3-[1-(2,4-dimethoxybenzyl)-2-oxo-1,2,5,6-tetrahydro-pyridin-3-yl]-propionic acid methyl ester (d) (0.16 mM) prepared by the Step 3 of above Example 1 was dissolved in methanol solution at room temperature. Then 154 mg of Zn (2.36 mM) and 0.01 ml of acetic acid (0.16 mM) were added thereto and the mixture was stirred for 20 hrs at 80° C. The resulting compound was purified by Silica gel column chromatography with a solvent mixture mixed with ethylacetate and hexane (1:1) as an eluant to give 43 mg of 3-[1-(4-amino-benzyl)-2-oxo-1,2,5,6-tetrahydro-pyridin-3-yl]-propionic acid methyl ester (h) (yield: 92%).

$^1$H-NMR (300 MHz, CDCl$_3$) δ 8.22 (d, 1H, J=8.5 Hz), 8.11 (d, 1H, J=8.4 Hz), 7.37 (t, 2H, J=8.3 Hz), 6.33 (t, 1H, J=4.3 Hz), 4.66 (d, 2H, J=7.5 Hz), 3.63 (s, 3H), 3.29 (t, 2H, J=6.6 Hz), 2.63 (t, 2H, J=6.9 Hz), 2.54 (t, 2H, J=6.6 Hz), 2.28 (t, 2H, J=4.2 Hz)

Step 2. Preparation of 3-[1-(4-acetylamino-benzyl)-2-oxo-1,2,5,6-tetrahydro-pyridin-3-yl)-propionic acid methyl ester (i)

17.5 mg of 3-[1-(4-amino-benzyl)-2-oxo-1,2,5,6-tetrahydro-pyridin-3-yl]-propionic acid methyl ester (h) prepared by above Step 1 was dissolved in methylene chloride solution (0.06 mM). And then 6 μl of (AcO)$_2$O (0.07 mM), 0.01 ml of triethylamine (0.08 mM) and 1.0 mg of DMAP (0.008 mM) were added thereto and the mixture was stirred for 3 hrs at 0° C. The reaction was stopped by adding methanol and the mixture was extracted three times with 10 ml of ethyl acetate. The organic layer was washed with saturated NaCl solution, dried over anhydrous MgSO$_4$, filtered and concentrated in vacuo. The resulting compound was purified with Silica gel column chromatography with ethylacetate as an eluant to give 46 mg of 3-[1-(4-acetylamino-benzyl)-2-oxo-1,2,5,6-tetrahydro-pyridin-3-yl)-propionic acid methyl ester (i) (yield: 44%).

$^1$H-NMR (300 MHz, CDCl$_3$) δ 8.34 (s, 1H), 7.40 (d, 2H, J=8.4 Hz), 7.10 (d, 2H, J=8.4 Hz), 6.29 (t, 1H, J=4.2 Hz), 4.50 (s, 2H), 3.61 (s, 3H), 3.22 (t, 2H, J=7.1 Hz), 2.59 (t, 2H, J=7.1 Hz), 2.51 (d, 2H, J=6.6 Hz), 2.22 (dd, 2H, J=6.9 Hz), 2.09 (s, 3H)

Step 3. Preparation of 3-[1-(4-acetylamino-benzyl)-2-oxo-1,2,5,6-tetrahydro-pyridin-3-yl)-N-hydroxy-propionamide (j1)

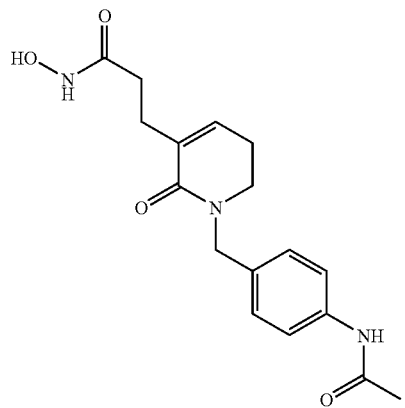

3-[1-(4-acetylamino-benzyl)-2-oxo-1,2,5,6-tetrahydro-pyridin-3-yl)-propionic acid methyl ester (i) prepared by above Step 2 dissolved in organic solvent such as methanol was reacted with amine salt to give 3-[1-(4-acetylamino-benzyl)-2-oxo-1,2,5,6-tetrahydro-pyridin-3-yl)-N-hydroxy-propionamide (j1).

$^1$H-NMR (300 MHz, CDCl$_3$) δ 7.50 (d J=8.0 Hz 2H), 7.23 (d J=8.0 Hz 2H), 6.44 (br t 1H), 4.57 (S 2H), 3.33 (t, J=6.5 Hz, 6H) 2.57 (br t, 2H) 2.30-2.26 (m, 4H) 2.10 (s, 2H)

Example 75

Preparation of N-4-[5-(2-hydroxycarbamoyl-ethyl)-6-oxo-3,6-dihydro-2-pyridin-1-yl-methyl]-phenyl-benzamide (j2)

N-4-[5-(2-hydroxycarbamoyl-ethyl)-6-oxo-3,6-dihydro-2-pyridin-1-yl-methyl]-phenyl-benzamide (j2) was prepared by the similar procedure described in above Example 74 (See Table 15).

Example 76

Preparation of N-hydroxy-3-[1-(4-dimethylsulfonylamino-benzyl)-2-oxo-1,2,5,6-tetrahydro-pyridin-3-yl]-propionamide (j3)

N-hydroxy-3-[1-(4-dimethylsulfonylamino-benzyl)-2-oxo-1,2,5,6-tetrahydro-pyridin-3-yl]-propionamide (j3) was prepared by the similar procedure described in above Example 74 (See Table 15).

Example 77

Preparation of N-hydroxy-3-2-oxo-1-[4-(toluene-4-sulfonylamino)-benzyl-1,2,5,6-tetrahydro-pyridin-3-yl]-propionamide (j4)

N-hydroxy-3-2-oxo-1-[4-(toluene-4-sulfonylamino)-benzyl-1,2,5,6-tetrahydro-pyridin-3-yl]-propionamide (j4) was prepared by the similar procedure described in above Example 74 (See Table 15).

TABLE 15

| Example | Chemical structure | NMR spectrum data |
| --- | --- | --- |
| 75 | 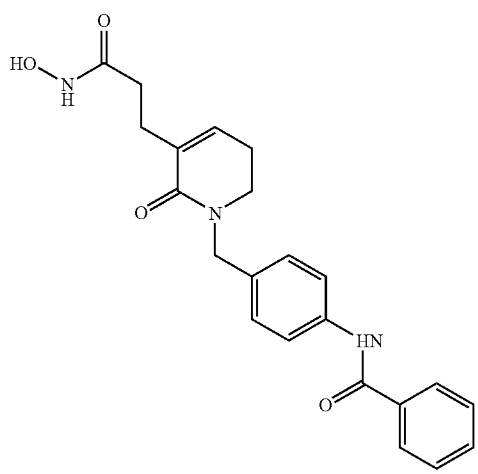 | 7.90 (t, J=7.05 Hz 2H), 7.67 (d, J=8.10 Hz, 2H) 7.59–7.47(m, 3H) 7.30 (d, J=8.10 Hz 2H), 6.45 (br t, 1H) 4.61 (s, 2H) 3.36 (t, J=7.2, 2H) 3.30 (q, J–1.5 Hz, 4H) 2.58 (br t, 2H) |
| 76 | 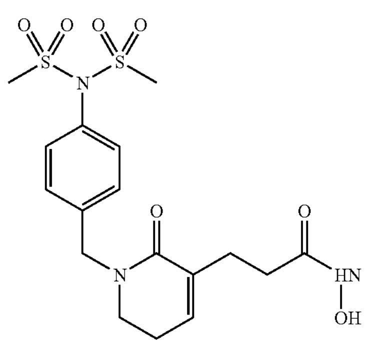 | 7.24 (q, J=8.6 Hz, 4H) 6.45 (br t, 1H) 4.58 (s, 2 H) 3.38–3.29 (m, 7H) 2.93 (s, 3H) 2.57 (t, 2H, J=7.1) 2.34–2.24(m, 4H) |
| 77 | 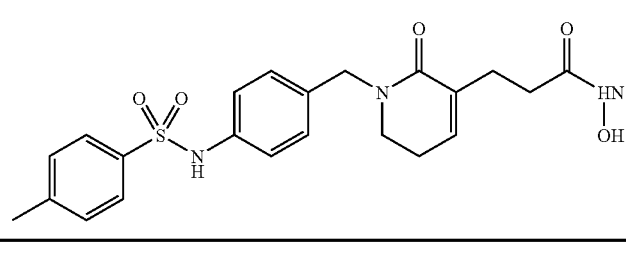 | 7.78 (d, J=8.0 Hz, 2H), 7.31 (d, J=7.5 Hz, 2H) 7.27–7.21 (m, 4H) 6.97 (t, J=7.2 Hz, 1H) 4.61 (d, J=3.5 Hz, 1H) 3.47(s, 4H) 3.36–3.30 (m, 1H) 2.71–2.64(m, 1H) 2.51–2.44 (m, 3H), 2.32 (d, J=4.5 Hz, 1H) |

Example 78

Preparation of 3-[1-(4-acetylamino-benzyl)-2-oxo-1,2,5,6-tetrahydro-pyridin-3-yl]-propionic acid (k)

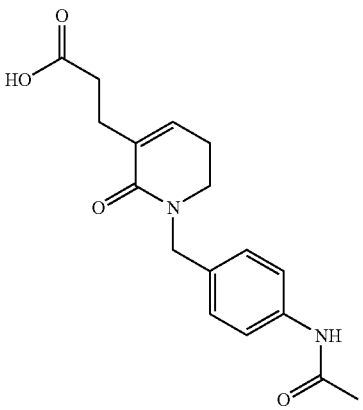

3-[1-(4-acetylamino-benzyl)-2-oxo-1,2,5,6-tetrahydro-pyridin-3-yl]-propionic acid methyl ester (i) prepared by above Step 2 of Example 18 dissolved in organic solvent such as tetrahydrofurane was reacted with LiOH to give 3-[1-(4-acetylamino-benzyl)-2-oxo-1,2,5,6-tetrahydro-pyridin-3-yl]-propionic acid (k).

$^1$H-NMR (300 MHz, CDCl$_3$) δ 7.50 (d J=8.0 Hz 2H), 7.23 (d J=8.6 Hz 2H), 6.45 (t J=4.5 Hz 1H), 4.58 (S 2H), 3.32 (t, J=7.5 Hz, 3H) 2.57 (t, J=7.5 Hz, 2H) 2.46 (t, J=7.5 Hz, 2H)

Example 79

Preparation of 3-[1-(4-benzoylamino-benzyl)-2-oxo-1,2,5,6-tetrahydro-pyridin-3-yl]-propionic acid (k2)

3-[1-(4-benzoylamino-benzyl)-2-oxo-1,2,5,6-tetrahydro-pyridin-3-yl]-propionic acid (k2) was prepared by the similar procedure described in above Example 78 (See Table 16).

Example 80

Preparation of 3-2-oxo-1-[4-(toluene-4-sulfonylamino)-benzyl]-2-oxo-1,2,5,6-tetrahydro-pyridin-3-yl]-propionic acid (k3)

3-2-oxo-1-[4-(toluene-4-sulfonylamino)-benzyl]-2-oxo-1,2,5,6-tetrahydro-pyridin-3-yl]-propionic acid (k3) was prepared by the similar procedure described in above Example 78 (See Table 16).

TABLE 16

| Example | Chemical structure | NMR spectrum data |
|---|---|---|
| 79 | 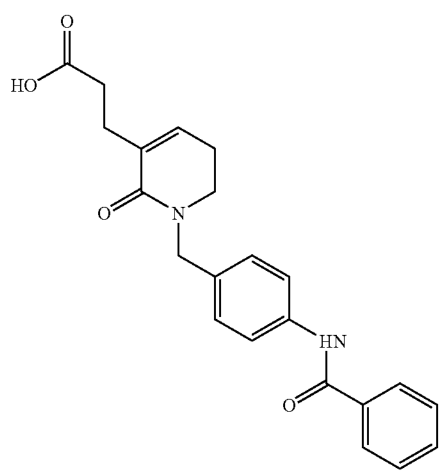 | 7.83 (d, J=6.9 Hz, 2H), 7.59(d, J=8.4 Hz, 2H), 7.49–7.37 (m, 4H), 7.19 (d, J=8.4 Hz, 2H), 6.33 (q, J=4.5 Hz, 1H) 3.26 (t, J=7.2 HZ, 3H) 2.54–2.40 (m, 4H) 2.24 (ab, J=11.6 Hz, 3.5 Hz, 2H) |
| 80 | 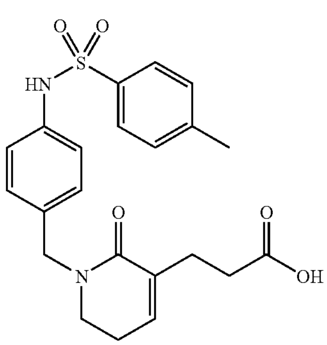 | 7.74(d, J=8.1 Hz, 4H), 7.18 (d, J=7.8 Hz, 2H), 6.93 (d, J=8.1, 2H), 4.53(s, 2H), 3.20(br t, 2H), 2.40 (s, 9H) |

Example 81

Preparation of N-hydroxy-3-(2-oxo-1-phenethyl-piperidine-3-yl)-propionamide (m)

Step 1. Preparation of [1-(2,4-dimethoxy-benzyl)-2-oxo-piperidine-3-yl]-acetic acid methyl ester (l)

3-[1-(2,4-dimethoxybenzyl)-2-oxo-1,2,5,6-tetrahydro-pyridin-3-yl]-propionic acid methyl ester was dissolved in alcohol solvent under nitrogen atmosphere. Then Pd—C was added thereto, and the mixture was hydrogenated under a hydrogen balloon for 1 to 2 hrs at room temperature. The reaction mixture was filtered and concentrated in vacuo. The resulting compound was purified with Silica gel column chromatography with a solvent mixture mixed with EtOAc/hexane (1:1) as an eluant to give [1-(2,4-dimethoxy-benzyl)-2-oxo-piperidine-3-yl]-acetic acid methyl ester (1) (yield: 74%).

$^1$H-NMR (300 MHz, CDCl$_3$) δ 7.13 (d, 1H, J=8.4 Hz), 6.42 (d, 2H, J=7.2 Hz), 4.51 (ab, 2H, J=32.9, 7.4 Hz), 3.76 (s, 6H), 3.66 (s, 3H), 3.24-3.18 (m, 2H), 2.93-2.72 (m, 2H), 2.56-2.43 (m, 1H), 1.98-1.55 (m, 4H)

Step 2. Preparation of N-hydroxy-3-(2-oxo-1-phenethyl-piperidine-3-yl)-propionamide (m)

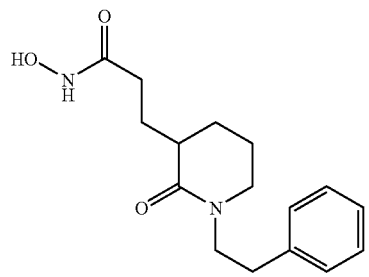

[1-(2,4-dimethoxy-benzyl)-2-oxo-piperidine-3-yl]acetic acid methyl ester (1) prepared by above Step 1 was reacted with amine salt to give N-hydroxy-3-(2-oxo-1-phenethyl-piperidine-3-yl)-propionamide (m).

$^1$H-NMR (300 MHz, CDCl$_3$) δ 7.26-7.17 (m 5H), 3.61-3.44 (m 2H) 3.08-2.83 (m 4H), 2.56-2.16 (m 4H)

Example 82

Preparation of 2-[1-(2,4-dimethoxy-benzyl)-2-oxo-1,2,5,6-tetrahydro-pyridin-3-yl]-N-hydroxy-acetamide (p1)

Step 1. Preparation of 3-(benzyl-but-3-enyl-carbamoyl)-but-3-enoic acid methyl ester (n)

2-Methylene-pentane dionate-5-methyl ester, EDC and DMAP were added to reaction solution dissolving the but-3-enyl-(2,4-dimethoxybenzyl)amine (b) prepared by above Step 1 of Example 1 in methylene chloride and the mixture was stirred for 5 hrs at room temperature to give 3-(benzyl-but-3-enyl-carbamoyl)-but-3-enoic acid methyl ester (n).

$^1$H-NMR (300 MHz, CDCl$_3$) δ 7.30-7.19 (m, 5H), 5.69 (br t, 1H), 5.23 (s, 2H), 5.00 (t, 2H, J=12.6 Hz), 4.74 (s, 2H), 3.61 (s, 3H), 3.42 (s, 4H), 2.30 (q, 2H, J=7.2 Hz)

Step 2. Preparation of [1-(2,4-dimethoxy-benzyl)-2-oxo-1,2,5,6-tetrahydro-pyridin-3-yl]-acetic acid methyl ester (o)

3-(benzyl-but-3-enyl-carbamoyl)-but-3-enoic acid methyl ester (n) prepared by above Step 1 was added to the catalyst solution containing Grubb's (I) catalysis such as ruthenium dissolved in organic solvent such as CH$_2$Cl$_2$ to give [1-(2,4-dimethoxy-benzyl)-2-oxo-1,2,5,6-tetrahydro-pyridin-3-yl]-acetic acid methyl ester (o).

$^1$H-NMR (300 MHz, CDCl$_3$) δ 7.17 (d, 1H, J=6.2 Hz), 6.42-6.36 (m, 3H), 4.54 (s, 2H), 3.76 (d, 6H, J=3.0 Hz), 3.66 (s, 3H), 3.35 (t, 2H, J=6.9), 3.28 (s, 2H), 2.29 (ab, 2H, J=11.3, 3.4 Hz)

Step 3. Preparation of 2-[1-(2,4-dimethoxy-benzyl)-2-oxo-1,2,5,6-tetrahydro-pyridin-3-yl]-N-hydroxy-acetamide (p1)

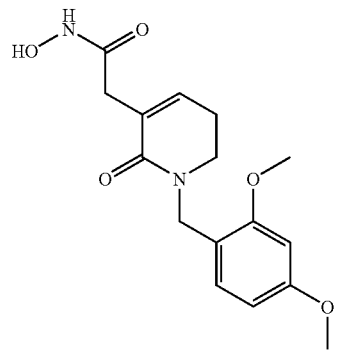

[1-(2,4-dimethoxy-benzyl)-2-oxo-1,2,5,6-tetrahydro-pyridin-3-yl]-acetic acid methyl ester (o) prepared by above Step 2 dissolved in alcohol solvent was reacted with amine salt to give 2-[1-(2,4-dimethoxy-benzyl)-2-oxo-1,2,5,6-tetrahydro-pyridin-3-yl]-N-hydroxy-acetamide (p1).

$^1$H-NMR (300 MHz, CDCl$_3$) δ 7.14 (d, J=8.7 Hz, 1H), 6.54 (br t, 1H) 6.44 (d, J=6.0 Hz, 2H), 4.55 (s, 2H), 3.78 (s, 6H), 3.41-3.32 (m, 2H), 3.20 (s, 2H), 2.0 (d, J=4.5 Hz, 2H)

Example 83

Preparation of 2-(1-benzyl-2-oxo-1,2,5,6-tetrahydro-pyridin-3-yl)-N-hydroxy-acetamide (p2)

2-(1-benzyl-2-oxo-1,2,5,6-tetrahydro-pyridin-3-yl)-N-hydroxy-acetamide (p2) was prepared by the similar procedure described in above Example 82 (See Table 17).

Example 84

Preparation of N-hydroxy-2-[1-(4-nitro-benzyl)-2-oxo-1,2,5,6-tetrahydro-pyridin-3-yl)-N-hydroxy-acetamide (p3)

N-hydroxy-2-[1-(4-nitro-benzyl)-2-oxo-1,2,5,6-tetrahydro-pyridin-3-yl)-N-hydroxy-acetamide (p3) was prepared by the similar procedure described in above Example 82 (See Table 17).

Example 85

Preparation of N-hydroxy-2-[2-oxo-1-(3-phenyl-propyl)-1,2,5,6-tetrahydro-pyridin-3-yl]-N-hydroxy-acetamide (p4)

N-hydroxy-2-[2-oxo-1-(3-phenyl-propyl)-1,2,5,6-tetrahydro-pyridin-3-yl]-N-hydroxy-acetamide (p4) was prepared by the similar procedure described in above Example 82 (See Table 17).

Example 86

Preparation of N-hydroxy-2-[2-oxo-1-(4-phenyl-butyl)-1,2,5,6-tetrahydro-pyridin-3-yl]-N-hydroxy-acetamide (p5)

N-hydroxy-2-[2-oxo-1-(4-phenyl-butyl)-1,2,5,6-tetrahydro-pyridin-3-yl]-N-hydroxy-acetamide (p5) was prepared by the similar procedure described in above Example 82 (See Table 17).

TABLE 17

| Example | Chemical structure | NMR spectrum data |
|---|---|---|
| 83 | 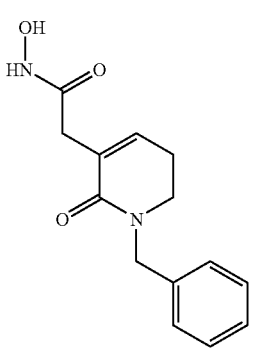 | 7.34–7.22 (m, 5H), 6.58 (t, J=4.5 Hz, 1H) 4.60 (s, 2H) 3.39–3.30(m, 3H) 3.20 (s, 2H) 2.39–2.30 (m, 2H) |
| 84 | 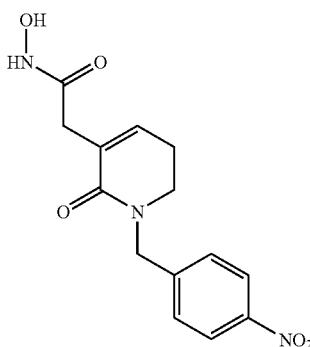 | 8.21 (d, J=8.7 Hz, 1H), 7.44 (d, J=8.7 Hz, 2H) 6.63 (t, J=4.3 Hz, 1H), 4.75 (s, 2H), 3.41(ab, J=6.5 Hz, 4H), 2.43(ab, J=6.2 Hz, 2H) |
| 85 | 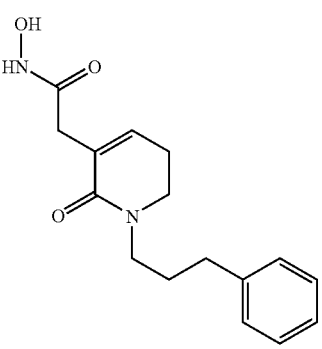 | 7.22 (d, J=6.5 Hz, 2H) 7.14(s, 3H) 6.51(br t, 1H) 3.43–3.32 (m, 5H) 3.11(s, 1H) 2.59(s, 2H) 2.29(s, 2H) 1.84(s, 2H) |
| 86 | 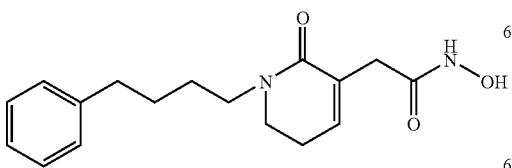 | 7.28–7.13 (m, 5H), 6.54(br t, 1H), 3.44–3.31 (m, 5H), 3.14(s, 1H) 2.62(t, J=7.1 Hz, 2H), 2.34(s, 2H), 1.58(t, J=3.4 Hz, 4H) |

Example 87

Preparation of [1-(2,4-dimethoxy-benzyl)-2-oxo-1,2,5,6-tetrahydro-pyridin-3-yl]-acetic acid (q1)

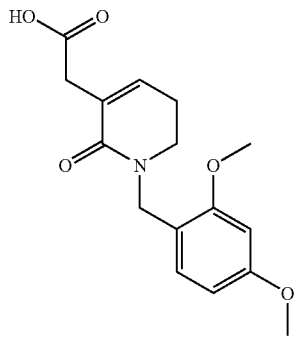

[1-(2,4-dimethoxy-benzyl)-2-oxo-1,2,5,6-tetrahydro-pyridin-3-yl]-acetic acid methyl ester (o) prepared by the Step 2 of Example 26 dissolved in TFA was reacted with LiOH to give [1-(2,4-dimethoxy-benzyl)-2-oxo-1,2,5,6-tetrahydro-pyridin-3-yl]-acetic acid (q1).

$^1$H-NMR (300 MHz, CDCl$_3$) δ 7.18 (d, J=8.7 Hz, 1H), 6.54 (t, J=4.3 Hz, 1H), 6.45 (d, J=6.6 Hz, 2H), 4.60 (s, 2H), 3.79 (s, 6H) 3.39 (t, J=7.3 Hz, 2H), 3.34 (s, 2H), 2.32 (ab, J=11.7 Hz, 3.6 Hz, 2H)

Example 88

Preparation of (1-benzyl-2-oxo-1,2,5,6-tetrahydro-pyridin-3-yl)-acetic acid (q2)

(1-benzyl-2-oxo-1,2,5,6-tetrahydro-pyridin-3-yl)-acetic acid (q2) was prepared by the similar procedure described in above Example 87 (See Table 18).

Example 89

Preparation of (2-oxo-1-phenethyl-1,2,5,6-tetrahydro-pyridin-3-yl)-acetic acid (q3)

(2-oxo-1-phenethyl-1,2,5,6-tetrahydro-pyridin-3-yl)-acetic acid (q3) was prepared by the similar procedure described in above Example 87 (See Table 18).

Example 90

Preparation of [2-oxo-1-(3-phenyl-propyl)-1,2,5,6-tetrahydro-pyridin-3-yl]-acetic acid (q4)

[2-oxo-1-(3-phenyl-propyl)-1,2,5,6-tetrahydro-pyridin-3-yl]-acetic acid (q4) was prepared by the similar procedure described in above Example 87 (See Table 18).

Example 91

Preparation of [2-oxo-1-(4-phenyl-butyl)-1,2,5,6-tetrahydro-pyridin-3-yl]-acetic acid (q5)

[2-oxo-1-(4-phenyl-butyl)-1,2,5,6-tetrahydro-pyridin-3-yl]-acetic acid (q5) was prepared by the similar procedure described in above Example 87 (See Table 18).

TABLE 18

| Example | Chemical structure | NMR spectrum data |
| --- | --- | --- |
| 88 | 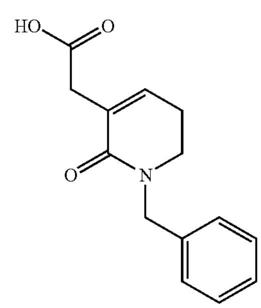 | 7.29–7.18 (m 5H) 6.50 (t, J=4.5 Hz, 1H), 4.58 (s, 2H), 3.31 (d, J=7.2 Hz 4H), 2.29 (ab, J=11.0 Hz, 3.5 Hz, 2H) |
| 89 | 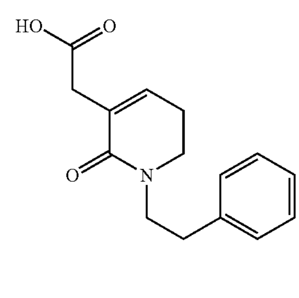 | 7.31–7.18 (m, 5H), 6.53 (t, J=4.5 Hz, 1H), 3.67 (t, J=7.2 Hz, 2H), 3.30 (s, 2H), 3.23 (t, J=7.2 Hz, 2H) 2.90 (t, J=7.2 Hz) 2.23 (ab, J=11.7 Hz, 3.6 Hz, 2H) |

TABLE 18-continued

| Example | Chemical structure | NMR spectrum data |
|---|---|---|
| 90 | 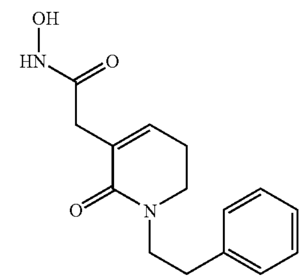 | 7.32–7.12 (m, 5H) 6.47(br t, 1H) 3.56(t, J=10.8 Hz, 2H), 3.11 (s, 4H) 2.78(d, J=6.0 Hz, 2H) 2.14(d, J=10.8 Hz, 2H) |
| 91 | 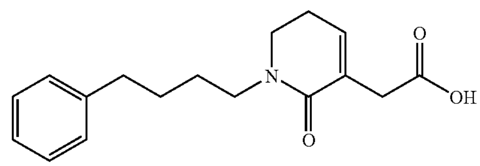 | 7.29–7.14 (m, 5H), 6.55(t, J=4.2 Hz, 1H), 3.46(t, J=6.7 Hz, 2H), 3.38(t, J=7.3 Hz, 2H), 3.31 (s, 2H) 2.64(t, J=7.1 Hz, 2H) 2.37(ab, J=6.3 Hz, 2H) 1.67–1.58(m, 4H) |

Example 92

Preparation of 2-[1-(2,4-dimethoxy-benzyl)-2-oxo-piperidine-3-yl]-N-hydroxy-acetamide (s1)

Step 1. Preparation of [1-(2,4-dimethoxy-benzyl)-2-oxo-piperidine-3-yl]acetic acid methyl ester (r)

26 mg of [1-(2,4-dimethoxy-benzyl)-2-oxo-1,2,5,6-tetrahydro-pyridin-3-yl]-acetic acid methyl ester (o) (0.08 mM) was dissolved in methanol solution under Ar atmosphere. 1.7 mg of 10% Pd—C was added thereto and the mixture was hydrogenated under a hydrogen balloon. The reaction mixture was stirred for 5 hrs at room temperature, filtered and concentrated in vacuo. The resulting compound was purified with Silica gel column chromatography to give 25 mg of [1-(2,4-dimethoxy-benzyl)-2-oxo-piperidine-3-yl]acetic acid methyl ester (r) (yield: 99%).

$^1$H-NMR (300 MHz, CDCl$_3$) δ 7.13 (d, J=8.4 Hz, 2H), 6.41 (dd, J=8.4 Hz, 2H), 6.41 (s, 1H), 4.51 (dd, J=32.7, 14.9 Hz, 2H), 3.76 (s, 6H), 3.66 (s, 3H), 3.22 (dd, J=7.5, 4.6 Hz, 2H), 2.90 (dd, J=15.9, 5.1 Hz, 1H), 2.76 (m, 1H), 2.52 (dd, J=16.2, 7.5 Hz, 2H), 1.98-1.55 (m, 4H)

Step 2. Preparation of 2-[1-(2,4-dimethoxy-benzyl)-2-oxo-piperidine-3-yl]-N-hydroxy-acetamide (s1)

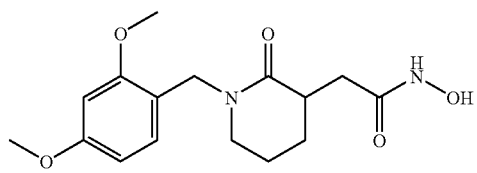

2-[1-(2,4-dimethoxy-benzyl)-2-oxo-piperidine-3-yl]-acetic acid methyl ester (r) prepared by the Step 1 was reacted with amine salt to give [1-(2,4-dimethoxy-benzyl)-2-oxo-piperidine-3-yl]-N-hydroxy-acetamide (s1).

$^1$H-NMR (300 MHz, CDCl$_3$) δ 7.15 (d, J=9.0 Hz, 1H), 6.46 (t, J=4.65, 2H), 4.56 (q, J=7.2 Hz, 23.7 Hz, 2H), 3.79 (s, 6H), 3.31-3.19 (m, 2H), 2.86-2.69 (m, 2H), 2.41 (d, J=14.1 Hz, 1H), 1.89-1.79 (m, 2H)

Example 93

Preparation of (2-oxo-1-phenethyl-piperidine-3-yl)-N-hydroxy-acetamide (s2)

(2-oxo-1-phenethyl-piperidine-3-yl)-acetic acid (s2) was prepared by the similar procedure described in above Example 92 (See Table 19).

Example 94

Preparation of [2-oxo-1-(3-phenyl-propyl)-piperidine-3-yl]-N-hydroxy-acetamide (s3)

[2-oxo-1-(3-phenyl-propyl)-piperidine-3-yl]-acetic acid (s3) was prepared by the similar procedure described in above Example 92 (See Table 19).

TABLE 19

| Example | Chemical structure | NMR spectrum data |
|---|---|---|
| 93 | 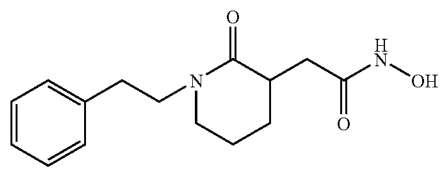 | 7.315–7.169(m, 5H), 3.60(t, J=7.35, 1H), 3.15(dd, J=4.8, 11.1, 1H), 2.917–2.856(m, 1H), 2.728–2.659(m, 1H), 1.698–1.426(m, 4H), 1.23(d, J=7.05, 5H) |
| 94 | 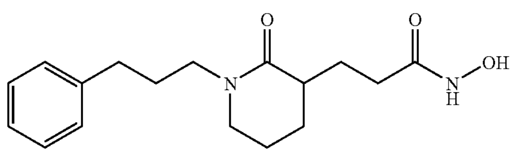 | 7.29–7.12(m, 5H) 3.47–3.35(m, 2H) 3.29–3.23(m, 2H)2.63–2.45(m, 4H) 2.03–1.80(m, 4H) 1.59–1.47(m, 2H), 1.33–1.19(m, 3H) |

Example 95

Preparation of 4-[1-(4-methoxy-benzyl)-2-oxo-1,2,5,6-tetrahydro-pyridin-3-yl]-N-hydroxy-butylamide (v1)

Step 1. Preparation of 5-[(4-methoxy-benzyl)-but-3-enyl-carbamoyl]-hex-5-enoic acid methyl ester (t)

2-Methylene-pentane dionate-5-methyl ester, EDC and DMAP were added to reaction solution dissolving the but-3-enyl-(2,4-dimethoxybenzyl)amine (b) prepared by above Step 1 of Example 1 in methylene chloride solution and the mixture was stirred for 5 hrs at room temperature to give 5-[(4-methoxy-benzyl)-but-3-enyl-carbamoyl]-hex-5-enoic acid methyl ester (t).

Step 2. Preparation of 4-[1-(4-methoxy-benzyl)-2-oxo-1,2,5,6-tetrahydro-pyridin-3-yl]-butyric acid methyl ester (u)

5-[(4-methoxy-benzyl)-but-3-enyl-carbamoyl]-hex-5-enoic acid methyl ester (t) prepared by above Step 1 was added to the catalyst solution containing Grubb's (I) catalysis such as ruthenium dissolved in organic solvent such as $CH_2Cl_2$ to give 4-[1-(4-methoxy-benzyl)-2-oxo-1,2,5,6-tetrahydro-pyridin-3-yl]-butyric acid methyl ester (u).

$^1$H-NMR (300 MHz, $CDCl_3$) δ 7.19 (d, J=8.4 Hz, 2H), 6.83 (d, J=8.4 Hz, 2H), 6.25 (t, J=4.2 Hz, 1H), 4.54 (s, 2H), 3.77 (s, 3H), 3.65 (s, 3H), 3.25 (t, J=6.9 Hz, 2H) 2.33 (t, J=7.3 Hz, 4H), 2.24 (q, J=4.5 Hz, 2H), 1.80 (t, J=7.2 Hz, 2H) 1.56 (s, 2H)

Step 3. Preparation of 4-[1-(4-methoxy-benzyl)-2-oxo-1,2,5,6-tetrahydro-pyridin-3-yl]-N-hydroxy-butylamide (v1)

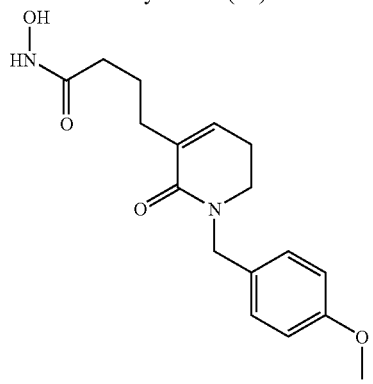

4-[1-(4-methoxy-benzyl)-2-oxo-1,2,5,6-tetrahydro-pyridin-3-yl]-butyric acid methyl ester (u) prepared by Step 2 dissolved in alcohol solvent was reacted with amine salt to give 4-[1-(4-methoxy-benzyl)-2-oxo-1,2,5,6-tetrahydro-pyridin-3-yl]-N-hydroxy-butylamide (v1).

$^1$H-NMR (300 MHz, $CDCl_3$) δ 7.19-7.15 (m, 2H), 6.83 (d, J=7.8 Hz, 2H), 6.28 (br t, 1H), 4.53 (s, 2H), 3.76 (s, 3H), 3.25 (dt, JA=7.5 Hz, JB=1.8 Hz, 2H), 2.38-2.23 (m, 6H), 1.85-1.76 (m, 2H)

Example 96

Preparation of 4-(1-phenethyl-2-oxo-1,2,5,6-tetrahydro-pyridin-3-yl)-N-hydroxy-butylamide (v2)

4-(1-phenethyl-2-oxo-1,2,5,6-tetrahydro-pyridin-3-yl)-N-hydroxy-butylamide (v2) was prepared by the similar procedure described in above Example 95 (See Table 20).

Example 97

Preparation of N-hydroxy-4-[2-oxo-1-(3-phenyl-propyl)-1,2,5,6-tetrahydro-pyridin-3-yl]-butylamide (v3)

N-hydroxy-4-[2-oxo-1-(3-phenyl-propyl)-1,2,5,6-tetrahydro-pyridin-3-yl]-butylamide (v3) was prepared by the similar procedure described in above Example 95 (See Table 20).

Example 98

Preparation of N-hydroxy-4-[2-oxo-1-(3-phenyl-butyl)-1,2,5,6-tetrahydro-pyridin-3-yl]-butylamide (v4)

N-hydroxy-4-[2-oxo-1-(3-phenyl-butyl)-1,2,5,6-tetrahydro-pyridin-3-yl]-butylamide (v4) was prepared by the similar procedure described in above Example 95 (See Table 20).

mixture was heated for 20 min at 80° C. The solvent was removed in vacuo and the remaining residue was recrystallized with mixture solution of methanol and ethylacetate to give 13 mg of 3-(2-oxo-1,2,5,6-tetrahydro-pyridin-3-yl)-propionic acid (g) (yield: 50%).

$^1$H-NMR (300 MHz, CD$_3$OD), δ 6.51 (m, 1H), 3.31 (m, 2H), 2.50 (m, 4H), 2.32 (m, 2H)

$^{13}$C-NMR (75 MHz, CD$_3$OD), δ 176.7, 168.6, 138.4, 134.5, 40.3, 34.1, 27.1, 25.0

TABLE 20

| Example | Chemical structure | NMR spectrum data |
| --- | --- | --- |
| 96 | 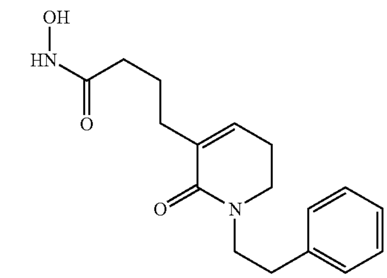 | 7.29–7.13(m, 5H), 6.24(br t, 1H), 3.56 (t, J=7.56 Hz 2H), 3.31–3.29 (m, 1H), 3.16 (t, J=6.9 Hz, 2H), 2.80(t, J=7.2 Hz, 2H), 2.14–2.03 (m, 5H), 1.66–1.61 (m, 2H) |
| 97 | 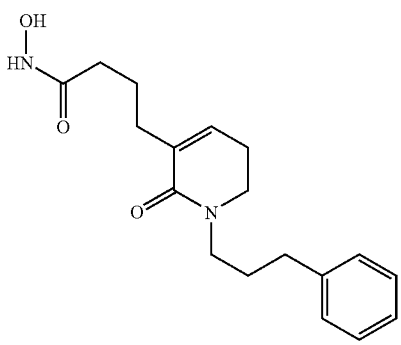 | 7.29–7.17(m, 5H); 6.32(br t, 1H), 3.46 (t, J=7.3 Hz, 2H), 3.35 (t, J=5.9 Hz, 2H), 2.63 (t, J=7.6 Hz, 2H), 2.37–2.28(m, 5H), 1.99–1.73 (m, 5H) |
| 98 | 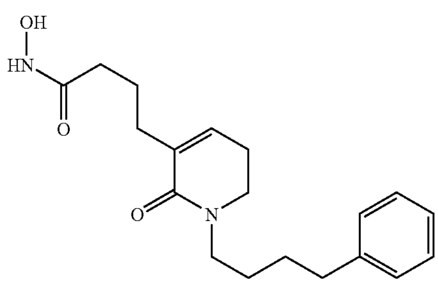 | 7.29–7.15(m, 5H), 6.31(br t, 1H),3.45 (t, J=6.5 Hz 2H), 3.32 (t, J=7.1 Hz, 2H), 2.64 (t, J=7.0 Hz, 2H), 2.27(d, J=7.2 Hz, 6H), 1.60 (s, 6H) |

Example 99

Preparation of 3-(2-oxo-1,2,5,6-tetrahydro-pyridin-3-yl)-propionic acid (g)

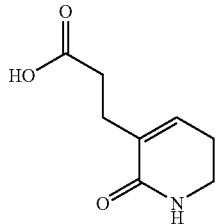

50 mg of 3-[1-(2,4-dimethoxybenzyl)-2-oxo-1,2,5,6-tetrahydro-pyridin-3-yl]-propionic acid (0.157 mM) was dissolved in 1 ml of trifluoroacetic acid solution. Then 0.074 ml of triethyl silane (0.465 mmol) was added thereto and the

Example 100

Preparation of N-Benzyloxy-3-(2-oxo-1,2,5,6-tetrahydro-pyridin-3-yl)-propionamide (h)

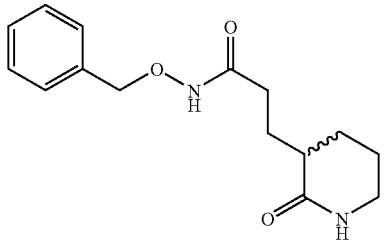

29 mg of 3-(2-oxo-1,2,5,6-tetrahydro-pyridin-3-yl)-propionic acid (g) was dissolved in 0.5 ml of DMF solution (0.171 mM). 30 mg of BnONH$_2$—HCl (0.188 mM), 0.033 ml of diisopropyl methylamine (0.189 mM), 43 mg of EDC (0.224 mM) and 5 mg of DMAP (0.041 mM) were added thereto and the mixture was stirred for overnight at room temperature. The mixture was diluted with 7 ml of ethyl acetate and washed with 5% HCl (1 ml) and 1 ml of sat. NaHCO$_3$ solution. The organic layer was dried over anhydrous MgSO$_4$, filtered and concentrated in vacuo. The resulting compound was purified by column chromatography on Silica gel with methanol/chloroform (1:20) solvent mixture as an eluant to give 126 mg of the title compound (h) (yield: 55%).

$^1$H-NMR (300 MHz, CDCl$_3$) δ 9.28 (s, br, 1H), 7.35 (m, 5H), 6.45 (s, br, 1H), 5.70 (s, br, 1H), 4.87 (s, 2H), 3.47 (s, br, 2H), 2.53 (m, 2H), 2.27 (m, 4H)

$^{13}$C-NMR (75 MHz, CDCl$_3$) δ 170.1, 166.9, 137.8, 135.6, 133.0, 129.1, 128.5, 78.0, 39.7, 32.8, 26.9, 24.1

Example 101

Preparation of 3-(1-Allyl-2-oxo-1,2,5,6-tetrahydro-pyridin-3-yl)-N-hydroxy-propionamide (j1)

Step 1. Preparation of 3-(2-oxo-1,2,5,6-tetrahydro-pyridin-3-yl)-propionic acid methyl ester (f)

310 mg of 3-[1-(2,4-dimethoxybenzyl)-2-oxo-1,2,5,6-tetrahydro-pyridin-3-yl]-propionic acid methyl ester (d) (0.93 mM) was dissolved in 3 ml of trifluoroacetic acid solution. Then 0.222 ml of triethyl silane (1.395 mmol) was added thereto and the mixture was heated for 20 min at 80° C. The solvent was removed in vacuo and the remaining residue was diluted in 20 ml of chloroform. The organic layer was washed with 5 ml of sat. NaHCO$_3$ solution and 5 ml of sat. NaCl solution. Then the organic layer was dried over anhydrous MgSO$_4$, filtered and concentrated in vacuo. The resulting compound was purified by column chromatography on Silica gel with EtOAc solvent as an eluant to give 126 mg of the title compound (f) (yield: 55%).

$^1$H-NMR (300 MHz, CDCl$_3$) δ 6.64 (s, br, 1H), 6.35 (t, J=3.0 Hz, 1H), 3.59 (s, 3H), 3.31 (m, 2H), 2.48 (m, 4H), 2.26 (m, 2H)

$^{13}$C-NMR (75 MHz, CDCl$_3$) δ 73.4, 166.8, 136.1, 133.5, 51.4, 39.5, 33.1, 26.0, 24.0

Step 2. Preparation of 3-(1-allyl-2-oxo-1,2,5,6-tetrahydro-pyridin-3-yl)-propionic acid methyl ester (i1)

0.220 ml of NaHMDS solution (1.0 M in THF, 0.22 mM) was added to 0.5 ml of the THF solution containing 40 mg of 3-(2-oxo-1,2,5,6-tetrahydro-pyridin-3-yl)-propionic acid methyl ester (0.218 mM) prepared by the Step 1 in a dropwise manner at −79° C. and stirred at −79° C. for 30 mins. After 0.028 ml of allyl bromide (0.327 mM) was added to the reaction mixture, the mixture was stirred at 0° C. for 3 hrs. The reaction mixture was quenched by 2 ml of sat. NH$_4$Cl solution and then the organic layer was extracted with 7 ml of ethyl acetate. The combined organic layer was washed with 2 ml of sat. NH$_4$Cl solution and 2 ml of sat. NaCl solution. Then the organic layer was dried over anhydrous MgSO$_4$, filtered and concentrated in vacuo. The resulting compound was purified by column chromatography on Silica gel with EtOAc/hexane (1:2) solvent mixture as an eluant to give 36 mg of the title compound (I 1) (yield: 74%).

$^1$H-NMR (300 MHz, CDCl$_3$) δ 6.28 (m, 1H), 5.74 (m, 1H), 5.14 (m, 2H), 3.99 (d, J=5.7 Hz 2H), 3.61 (s, 3H), 3.27 (t, J=6.9 Hz, 2H), 2.51 (m, 4H), 2.27 (m, 2H)

$^{13}$C-NMR (75 MHz, CDCl$_3$) δ 173.6, 164.6, 134.3, 134.1, 133.3, 117.1, 51.4, 49.0, 44.6, 33.3, 26.6, 23.8

Step 3. Preparation of 3-(1-allyl-2-oxo-1,2,5,6-tetrahydro-pyridin-3-yl)-N-hydroxy-propionamide (j 1)

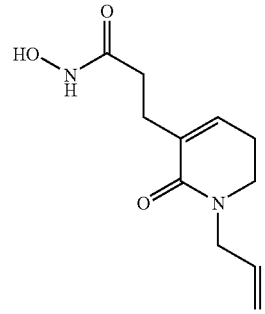

24 mg of 3-(1-allyl-2-oxo-1,2,5,6-tetrahydro-pyridin-3-yl)-propionic acid methyl ester (i1) prepared from the above Step 2 was dissolved in methanol solution (0.11 mM) and then 0.122 ml of 1.7M NH$_2$OK suspension solution (0.207 mM) was added thereto at 0° c. and stirred for 3 hrs at room temperature. The resulting mixture was neutralized with 0.02 ml of acetic acid, diluted with 10 ml of ethyl acetate solution, filtered and concentrated in vacuo. The resulting compound was purified by column chromatography on Silica gel with methanol/chloroform (1:10) solvent mixture as an eluant to give 11 mg of the title compound (j1) (yield: 48%).

$^1$H-NMR (300 MHz, CDCl$_3$): δ 6.39 (br t, 1H), 5.78-5.67 (m, 1H), 5.17 (d, J=5.4 Hz, 1H), 5.12 (s, 1H), 3.98 (d, J=5.4 Hz, 2H), 3.30 (t, J=7.0 Hz, 2H), 2.54-2.28 (m, 6H)

Example 102

Preparation of N-hydroxy-3-(1-methyl-2-oxo-1,2,5,6-tetrahydro-pyridin-3-yl)-propionamide (j2)

Step 1. Preparation of 3-(1-methyl-2-oxo-1,2,5,6-tetrahydro-pyridin-3-yl)-propionic acid methyl ester (i2)

0.22 ml of 1.0M NaHMDS solution in THF (0.22 mM) was added to 0.5 ml of THF solution containing 80 mg 3-(2-oxo-1,2,5,6-tetrahydro-pyridin-3-yl)-propionic acid methyl ester (f) prepared from the step 1 in Example 3 (0.44 mM) in a dropwise manner at −79° C. and then stirred for 30 min. After 0.48 ml of methyl bromide (0.48 mM) was added to the reaction mixture, the solution was stirred at 0° C. for 3 hrs. The reaction mixture was quenched by 2 ml of sat. NH$_4$Cl solution and then the organic layer was extracted with ethyl acetate (7 ml). The combined organic layer was washed with 2 ml of sat. NH$_4$Cl solution (2 ml) and 2 ml of sat. NaCl solution subsequently. Then the organic layer was dried over anhydrous MgSO$_4$, filtered and concentrated in vacuo. The resulting compound was purified by column chromatography on Silica gel with EtOAc solvent as an eluant to give 62 mg of the title compound (i2) (yield: 72%).

Step 2. Preparation of N-hydroxy-3-(1-methyl-2-oxo-1,2,5,6-tetrahydro-pyridin-3-yl)-propionamide (j2)

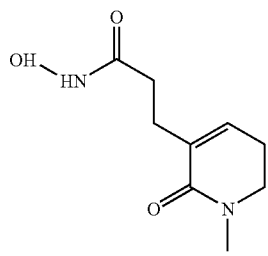

50 mg of 3-(1-methyl-2-oxo-1,2,5,6-tetrahydro-pyridin-3-yl)-propionic acid methyl ester prepared from the above Step 1 was dissolved in methanol (0.25 mM) and then 0.122 ml of 1.7M NH$_2$OK suspension solution in methanol (0.207 mM) was added thereto at 0° C. and the resulting mixture was stirred for 3 hrs at room temperature. The resulting mixture was neutralized with 0.02 ml of acetic acid, diluted with 10 ml of ethyl acetate, filtered and concentrated in vacuo. The resulting compound was purified by column chromatography on Silica gel with methanol/chloroform (1:20) solvent mixture as an eluant to give 19 mg of the title compound (j2) (yield: 35%).

$^1$H-NMR (300 MHz, CD$_3$OD) δ 6.15 (t, J=4.3 Hz, 1H), 3.41 (t, J=7.2 Hz, 2H), 2.97 (s, 3H), 2.51 (t, J=7.5 Hz, 2H), 2.35 (m, 2H), 2.22 (t, J=7.5 Hz, 2H)

Example 103

Preparation of N-hydroxy-3-(1-(naphthalene-2-yl-methyl)-2-oxo-1,2,5,6-tetrahydro-pyridin-3-yl)-propionamide 70 mg of 3-[1-(Naphthyl-2-yl)methyl-2-oxo-1,2,5,6-tetrahydro-pyridin-3-yl]-propionic acid methyl ester was dissolved in methanol solution (0.22 mM) and then 0.64 ml of 1.7M NH$_2$OK suspension in methanol (1.08 mM) was added thereto at 0° C. and the resulting mixture was stirred for 5 hrs at room temperature. The resulting mixture was neutralized with 0.02 ml of acetic acid and concentrated in vacuo. The resulting solid was filtered with 10% methanol/chloroform solvent mixture and concentrated in vacuo. The resulting compound was purified by column chromatography on Silica gel with methanol/chloroform (1:9) solvent mixture as an eluant to give 61 mg of the title compound (See Table 21) (yield: 95%).

Example 104

Preparation of N-hydroxy-3-[2-oxo-1-(2-thiophen-2-yl-ethyl)-1,2,5,6-tetrahydro-pyridin-3-yl]-propionamide 60 mg of 3-[2-oxo-1-(2-thiophen-2-yl)ethyl-1,2,5,6-tetrahydro-pyridin-3-yl]-propionic acid methyl ester was dissolved in methanol to be 0.20 mM solution and then 0.6 ml of 1.7M NH$_2$OK suspension solution in methanol (1.02 mM) was added thereto at 0° C. and the resulting mixture was stirred for 5 hrs at room temperature. The resulting mixture was neutralized with 0.02 ml of acetic acid and concentrated in vacuo. The resulting solid was filtered with 10% methanol/chloroform solvent mixture and concentrated in vacuo. The resulting compound was purified by column chromatography on Silica gel with methanol/chloroform (1:9) solvent mixture as an eluant to give 44 mg of the title compound (See Table 21) (yield: 73%).

TABLE 21

| Example | Chemical structure | NMR spectrum data |
|---|---|---|
| 103 | 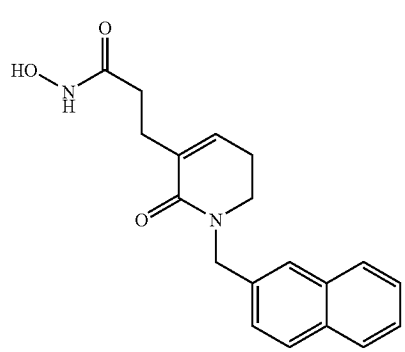 | 8.07–7.99 (m, 1H), 7.83–7.74 (m, 2H), 7.50–7.29 (m, 4H), 6.32 (br t, 1H), 5.01 (s, 2H), 3.44 (s, 2H), 3.15 (q, J=6.9 Hz, 2H), 2.71–2.54 (m, 2H), 2.42 (s, 2H), 2.09 (s, 2H) |

TABLE 21-continued

| Example | Chemical structure | NMR spectrum data |
| --- | --- | --- |
| 104 | 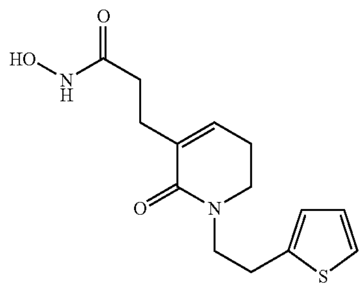 | 7.11 (d, J=4.8 Hz, 1H), 6.89 (t, J=3.9 Hz, 1H), 6.82 (s, 1H), 6.35 (br t, 1H), 3.64–3.59 (m, 2H), 3.22 (t, J=3.22 Hz, 2H), 3.09–3.04 (m, 2H), 2.54–2.50 (m, 2H), 2.35 (s, 2H), 2.20(s, 2H) |

Example 105

Preparation of 3-(1-Benzyl-2-oxo-2,5,6,7-tetrahydro-1H-azepin-3-yl)-N-hydroxy-propionamide (e1)

Step 1. Preparation of Benzyl-pent-4-enyl-amine (b)

0.397 ml of 5-Bromo-1-pentene (3.35 mmol) and 0.67 ml of diisopropyl ethylamine (3.96 mmol) were added to the reaction solution containing 0.74 ml of benzylamine (a) (4.93 mmol) dissolved in acetonitrile with stirring and the mixture was stirred at room temperature for overnight. The reaction mixture was washed with saturated NaCl solution, dried over MgSO$_4$, filtered and concentrated in vacuo. The resulting compound was purified with Silica gel column chromatography with EtOAc solvent as an eluant to give 236 mg of the pure title compound (b) (yield: 44%).

$^1$H-NMR (300 MHz, CDCl$_3$) δ 7.35-7.24 (m, 5H), 5.92-5.78 (m, 1H), 5.09-4.98 (m, 2H), 3.80 (s, 2H), 2.67 (t, J=7.5 Hz,), 2.14 (q, J=7.5 Hz, 2H), 1.69-1.59 (m, 2H), 1.41 (br, 1H)

Step 2. Preparation of Preparation of 4-(Benzyl-pent-4-enyl-carbamoyl)-pent-4-enoic acid methyl ester (c)

320 mg of 2-methylene-pentane dionate-5-methyl ester (2.02 mmol), 340 mg of EDC (2.02 mmol) and 50 mg of DMAP (0.405 mmol) were added to 0.5 M of reaction solution dissolving the compound (b) prepared by above step 1 in methylene chloride and the mixture was stirred for 5 hrs at room temperature. The resulting mixture was diluted with ethyl acetate, and washed with 5% HCl solution (10 ml) and 10 ml of saturated NaHCO$_3$ solution to separate into an organic layer and water layer. The organic layer was dried over anhydrous MgSO$_4$, filtered and concentrated in vacuo. The resultant was purified by Silica gel column chromatography with a solvent mixture mixed with EtOAc and hexanes (1:2) as an eluant to give 150 mg of 4-[but-3-enyl-(2,4-dimethoxybenzyl)-carbamoyl]-pent-4-enoic acid methyl ester (c) (yield: 35%).

$^1$H-NMR (300 MHz, CDCl$_3$) δ 7.31-7.14 (m, 5H), 5.81-5.64 (m, 1H) 5.12 (s, 1H), 5.04-4.97 (m, 3H), 3.65 (s, 2H), 3.56-3.46 (m, 3H), 3.42-3.36 (m, 1H), 3.33-3.31 (m, 1H), 2.85 (d, J=3 Hz, 2H), 2.65-2.45 (m, 4H), 2.07-2.01 (m, 2H), 1.69-1.59 (m, 2H)

Step 3. 3-(1-Benzyl-2-oxo-2,5,6,7-tetrahydro-1H-azepin-3-yl)-propionic acid methyl ester (d)

150 mg of the compound (c) (0.476 mmol) prepared by the above Step 2 was added to the catalyst solution containing 40 mg of ruthenium (0.047 mmol) dissolved in CH$_2$Cl$_2$. Then the mixture was stirred for 24 hrs at room temperature, filtered and concentrated in vacuo. The resultant was purified by Silica gel column chromatography with methanol/chloroform (1:10) solvent mixture as an eluant to give 108 mg of the title compound (d) (yield: 79%).

$^1$H-NMR (300 MHz, CDCl$_3$) δ 7.28-7.26 (m, 5H), 5.99-5.94 (m, 1H), 4.63 (s, 2H), 3.60 (S, 2H), 3.21 (t, J=6 Hz 2H), 2.65 (t, J=7.2 Hz, 2H), 2.48 (t, J=6.9 Hz, 2H), 2.08-2.01 (m, 2H), 1.67-1.57 (m, 2H)

Step 4. Preparation of 3-(1-Benzyl-2-oxo-2,5,6,7-tetrahydro-1H-azepin-3-yl)-N-hydroxy-propionamide (e1)

108 mg of compound (d) prepared by the above Step 3 was dissolved in methanol solution (0.376 mmol) and then 1.7 M methanolic suspension solution containing NH$_2$OK (1.315 ml, 2.63 mmol) was added thereto at 0° C. and the resulting mixture was stirred for 3 hrs at room temperature. The resulting mixture was neutralized with 0.02 ml of acetic acid, diluted with 10 ml of ethyl acetate solution, filtered and concentrated in vacuo. The resulting compound was purified by column chromatography on Silica gel with methanol/chloroform (1:10) solvent mixture as an eluant to give 46 mg of the title compound (e1) (yield: 43%).

$^1$H-NMR (300 MHz, CDCl$_3$) δ 7.28-7.24 (m, 5H), 6.20-6.02 (m, 2H), 4.65 (s, 2H), 3.26 (d, J=3 Hz, 2H), 2.66-2.52 (m, 4H), 2.08-2.05 (m, 2H), 1.65-1.64 (m, 2H)

Example 106

Preparation of N-Hydroxy-3-[2-oxo-1-(3-phenyl-ethyl)-2,5,6,7-tetrahydro-1H-azepin-3-yl]-propionamide (2e)

N-Hydroxy-3-[2-oxo-1-(4-phenylethyl)-2,5,6,7-tetrahydro-1H-azepin-3-yl]-propionamide (2e) was prepared by the similar procedure described in above Example 105 (See Table 22).

Example 107

Preparation of N-Hydroxy-3-[2-oxo-1-(3-phenyl-propyl)-2,5,6,7-tetrahydro-1H-azepin-3-yl]-propionamide (3e)

N-Hydroxy-3-[2-oxo-1-(3-phenyl-propyl)-2,5,6,7-tetrahydro-1H-azepin-3-yl]-propionamide (3e) was prepared by the similar procedure described in above Example 105 (See Table 22).

Example 108

Preparation of N-Hydroxy-3-[2-oxo-1-(4-phenyl-butyl)-2,5,6,7-tetrahydro-1H-azepin-3-yl]-propionamide (4e)

N-Hydroxy-3-[2-oxo-1-(4-phenyl-butyl)-2,5,6,7-tetrahydro-1H-azepin-3-yl]-propionamide (4e) was prepared by the similar procedure described in above Example 105 (See Table 22).

activity causes the substrate to occur emmition wavelength in the ranging from 360 nm to 460 nm.

Various concentrations of the compounds of the present invention ranging from 0.01 to 10 μM were reacted with HDAC enzyme at 25° C. for 20 minutes and equal volume of developer was added thereto. The fluorescence signal was detected at the wavelength in the range 350 to 460 nm using by fluorescence spectrometer. $IC_{50}$ value is defined as the concentration of the sample required to reduce the maximum fluorescence to a half and the result was shown in Table 23.

TABLE 22

| Example | Chemical Structure | NMR Spectral data |
|---|---|---|
| 106 | 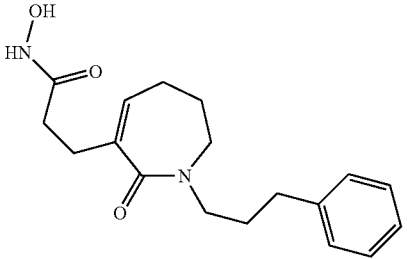 | 7.3–7.20 (m, 5H), 6.05 (t, J=6 Hz, 1H), 3.70 (t, J=6 Hz, 2H), 3.17, (t, J=6 Hz, 2H), 2.89(t, J=6 Hz, 2H), 2.58–2.35(m, 4H), 2.00 (t, J=6 Hz, 2H), 1.74(t, J=6 Hz, 2H) |
| 107 | 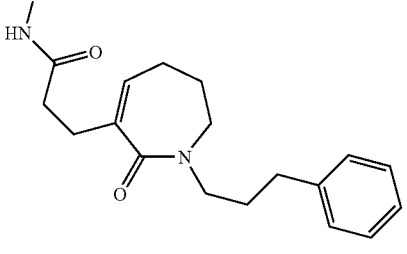 | 7.31–7.12 (m, 5H), 6.11–6.05 (m, 1H), 3.50 (br, 2H) 3.25(br, 2H), 2.76–2.47 (m, 6H), 2.17–2.09 (br, 2H), 1.91–1.88 (br, 2H) |
| 108 | 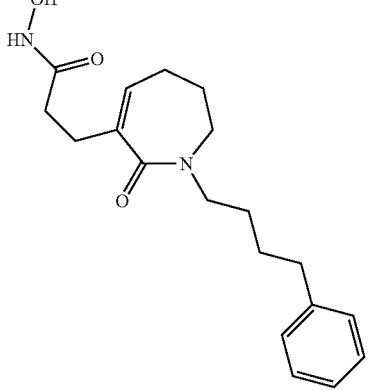 | 7.27–7.13 (m, 5H), 6.07–6.05 (m, 1H), 3.44(br, 2H), 3.22(br, 2H), 2.62–2.43(m, 6H), 2.09–2.07(br, 2H), 1.84–1.82(br, 2H), 1.65–1.55(br, 4H) |

Experimental Example 1

Effect of the Compound of the Present Invention on HDAC

To test the inhibiting effect of the compounds prepared from above Examples 1 to 108 on histone deacetylase (HDAC), HDAC Flourescent Activity Assay/Drug Discovery Kit (Biomol, USA) was used with nuclear extracts of HeLa cell as a HDAC source. Fluorogenic Histone Deacetylase Lysyl Substrate was used as substrate for HDAC and the test is based on the fact that the removal of acetyl group by HDAC As shown in Table 23, it was confirmed that compounds of the present invention showed potent inhibiting effect on the activity of HDAC enzyme.

Experimental Example 2

Effect of the Compound of the Present Invention on the Tumor Cell Growth

PC-3 cells (ATCC, US), human prostatic carcinoma cell line, were cultured in RMPI 1640 supplemented with 10% fetal bovine serum.

Appropriate concentrations of cells ($5 \times 10^4$ cells/ml) cultured in RMPI 1640 supplemented with 5% fetal bovine serum were poured into 96-well plate and incubated at 37° C. in 5% $CO_2$ condition. The day after the incubation, PC-3 cells were fixed on Time zero ($T_0$) plate by adding 50 μl/well of 50% trichloroacetic acid and the cell concentration was set to zero point by fixing the cells. In the cells treated with test samples, 50% TCA was added to each wells in 50 ul/well after 48 hrs to fix the cells. The final concentration of adding test compounds were 0.01, 0.03, 0.1, 0.3, 1 μg/ml respectively. Then, each fixed plate was washed, dried and 100 μl/well of 0.4% reaction solution containing sulforhodamine B (SRB) reagent dissolved in 0.1% acetic acid was added thereto to stain the cells. 30 minutes later, the cell was washed with 0.1% acetic acid, dried at room temperature, and 10 mM of TRIS base (pH 10.5) was added thereto to dissolve the staining agent. Finally, the absorbance detected at 540 nm was measured and the value was conversed into percentage comparing with that of control group. $IC_{50}$ (μg/ml), the concentration of the group required to inhibit the cancer cell growth by 50%, was calculated from the data (AA: $IC_{50}$'s<1, A: $IC_{50}$'s<5, B: $IC_{50}$'s<10 and C: $IC_{50}$'s>10). Also, the inhibiting activity of cell growth was expressed as various symbols in accordance with the potency of examples e.g., AA: closely equivalent (1~2 times), A: slightly weaker (3~5 times), B: weaker (5~10 times), C: very weaker (more than 10 times) than that of adriamycin used as a positive control group. The result was shown in Table 23.

As shown in Table 23, it was confirmed that compounds of the present invention inhibited HDAC directly and showed potent inhibiting effect on the activity of cancer cell growth, especially, PC-3 cancer cell.

TABLE 23

| Example | HDAC inhibition | Cell growth inhibition |
| --- | --- | --- |
| 1 | AA | A |
| 2 | AA | |
| 3 | AA | AA |
| 4 | AAA | A |
| 5 | C | |
| 6 | AA | B |
| 7 | AA | A |
| 8 | AA | A |
| 9 | C | A |
| 10 | | AA |
| 11 | | AA |
| 12 | AA | AA |
| 13 | AA | A |
| 14 | A | B |
| 15 | | |
| 16 | C | C |
| 17 | C | C |
| 18 | | B |
| 19 | | B |
| 20 | C | C |
| 21 | C | C |
| 22 | C | C |
| 23 | C | C |
| 24 | C | C |
| 25 | C | C |
| 26 | C | C |
| 27 | C | C |
| 28 | | A |
| 29 | | A |
| 30 | | A |
| 31 | A | A |
| 32 | A | A |
| 33 | A | A |
| 34 | | A |
| 35 | | A |
| 36 | | A |
| 37 | | A |
| 38 | | A |
| 39 | | A |
| 40 | | A |
| 41 | | B |
| 42 | | AA |
| 43 | | A |
| 44 | | B |
| 45 | | B |
| 46 | | B |
| 47 | | |
| 48 | | |
| 49 | AA | A |
| 50 | A | AA |
| 51 | A | C |
| 52 | | |
| 53 | | AA |
| 54 | C | A |
| 55 | AA | AA |
| 56 | AA | AAA |
| 57 | AA | AA |
| 58 | AA | B |
| 59 | AA | B |
| 60 | AA | B |
| 61 | AA | AA |
| 62 | AA | AA |
| 63 | C | C |
| 64 | C | C |
| 65 | C | C |
| 66 | C | C |
| 67 | C | C |
| 68 | C | C |
| 69 | C | C |
| 70 | C | |
| 71 | C | |
| 72 | C | |
| 73 | C | C |
| 74 | AA | C |
| 75 | AA | B |
| 76 | A | C |
| 77 | AA | A |
| 78 | C | |
| 79 | C | |
| 80 | C | |
| 81 | A | C |
| 82 | C | C |
| 83 | C | C |
| 84 | C | |
| 85 | C | |
| 86 | C | C |
| 87 | C | |
| 88 | C | |
| 89 | C | |
| 90 | C | |
| 91 | C | |
| 92 | C | C |
| 93 | C | |
| 94 | C | |
| 95 | C | C |
| 96 | C | |
| 97 | A | |
| 98 | A | |
| 99 | C | |
| 100 | C | |
| 101 | C | C |
| 102 | C | C |
| 103 | C | B |
| 104 | C | B |
| 105 | C | C |
| 106 | C | C |
| 107 | C | C |
| 108 | C | C |

Experimental Example 3

Toxicity Test

Methods

The acute toxicity tests on ICR mice (mean body weight 25±5g) and Sprague-Dawley rats (235±10g, Jung-Ang Lab Animal Inc.) were performed using the compounds of example 80. Four group consisting of 10 mice or rats was administrated orally with 4 mg/kg, 40 mg/kg, 400 mg/kg and 4,000 mg/kg of test sample or solvents (0.2 ml, i.p.) respectively and observed for 2 weeks.

Results

There were no treatment-related effects on mortality, clinical signs, body weight changes and gross findings in any group or either gender. These results suggested that the extract prepared in the present invention were potent and safe.

Hereinafter, the formulating methods and kinds of excipients will be described, but the present invention is not limited to them. The representative preparation examples were described as follows.

| Preparation of powder | |
|---|---|
| the compounds of example 80 | 50 mg |
| Lactose | 100 mg |
| Talc | 10 mg |

Powder preparation was prepared by mixing above components and filling sealed package.

| Preparation of tablet | |
|---|---|
| the compounds of example 80 | 50 mg |
| Corn Starch | 100 mg |
| Lactose | 100 mg |
| Magnesium Stearate | 2 mg |

Tablet preparation was prepared by mixing above components and entabletting.

| Preparation of capsule | |
|---|---|
| the compounds of example 80 | 50 mg |
| Corn starch | 100 mg |
| Lactose | 100 mg |
| Magnesium Stearate | 2 mg |

Tablet preparation was prepared by mixing above components and filling gelatin capsule by conventional gelatin preparation method.

| Preparation of injection | |
|---|---|
| the compounds of example 80 | 50 mg |
| Distilled water for injection | optimum amount |
| PH controller | optimum amount |

Injection preparation was prepared by dissolving active component, controlling pH to about 7.5 and then filling all the components in 2 ml ample and sterilizing by conventional injection preparation method.

| Preparation of liquid | |
|---|---|
| the compounds of example 80 | 0.1~80 g |
| Sugar | 5~10 g |
| Citric acid | 0.05~0.3% |
| Caramel | 0.005~0.02% |
| Vitamin C | 0.1~1% |
| Distilled water | 79~94% |
| $CO_2$ gas | 0.5~0.82% |

Liquid preparation was prepared by dissolving active component, filling all the components and sterilizing by conventional liquid preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

As described in the present invention, the 2-oxo-cyclic compound of the present invention have potent anti-cancer activity, therefore, it can be used as the therapeutics for treating and preventing the cancer disease comprising lung cancer, bone cancer, pancreatic cancer, skin cancer, cancer of the head and neck, cutaneous or intraocular melanoma, uterine cancer, ovarian cancer, rectal cancer or cancer of the anal region, stomach cancer, colon cancer, breast cancer, gynecologic tumors, Hodgkin's disease, cancer of the esophagus, cancer of the small intestine, cancer of the endocrine system, sarcomas of soft tissues, cancer of the urethra, cancer of the penis, prostate cancer, chronic or acute leukemia, solid tumors of childhood, lymphocytic lymphonas, cancer of the bladder, cancer of the kidney or ureter, or neoplasms of the central nervous system.

What is claimed is:

1. A pharmaceutical composition comprising; a compound represented by the following general formula (III), and a pharmaceutically acceptable salt or an isomer thereof:

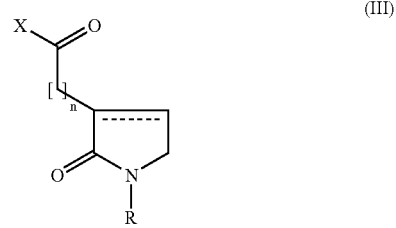

(III)

wherein

X is selected from the group consisting of a hydroxyl group, —NHOH, —NHOCH$_2$Ph,

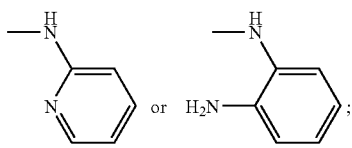

R is selected from the group consisting of a C1-C5 alkyl group, C2-C5 alkenyl group, C2-C5 alkynyl group, C3-C5 alkyl group, a heterocyclic group and aromatic aryl group;

n is an integer of 1 to 5; and dotted line ((-----)) means double bond.

2. The pharmaceutical composition of claim 1, wherein said R is selected from the group consisting of thiophenyl group, naphtyl group, pyrrolyl group, furyl group and biphenyl group.

3. The pharmaceutical composition of claim 2, wherein said compound is selected from the group consisting of;
   N-hydroxy-3-(1-naphthalene-2-ylmethyl-2-oxo-2,5-dihydro-1H-pyrrol-3-yl)-propionamide,
   N-hydroxy-3-(1-methyl-2-oxo-2,5-dihydro-1H-pyrrol-3-yl)-propionamide,
   3-(1-allyl-2-oxo-2,5-dihydro-1H-pyrrol-3-yl)-N-hydroxy-propionamide,
   N-hydroxy-3-[1-(2-naphthalene-1-yl-ethyl)-2-oxo-2,5-dihydro-1H-pyrrol-3-yl]-propionamide,
   N-hydroxy-3-[1-(2-naphthalene-2-yl-ethyl)-2-oxo-2,5-dihydro-1H-pyrrol-3-yl]-propionamide,
   N-hydroxy-3-[2-oxo-1-(2-thiophen-2-yl-ethyl)-2,5-dihydro-1H-pyrrol-3-yl]-propionamide,
   3-[1-(3-biphenyl-4-yl-propyl)-2-oxo-2,5-dihydro-1H-pyrrol-3-yl]-N-hydroxy-propionamide, and
   N-hydroxy-3-[1-(3-naphthalene-2-yl-propyl)-2-oxo-2,5-dihydro-1H-pyrrol-3-yl]-propionamide.

4. The pharmaceutical composition of claim 3, wherein said compound is N-hydroxy-3-[1-(2-naphthalene-2-yl-ethyl)-2-oxo-2,5-dihydro-1H-pyrrol-3-yl]-propionamide.

5. A method of treatment for prostate cancer to produce a beneficial effect comprising; administering a compound represented by the following general formula (III), and a pharmaceutically acceptable salt or an isomer thereof, to a Mammal in need thereof,

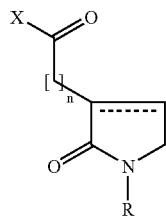

(III)

wherein

X is selected from the group consisting of a hydroxyl group, —NHOH, —NHOCH₂Ph,

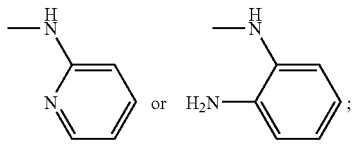

R is selected from the group consisting of a C1-C5 alkyl group, C2-C5 alkenyl group, C2-C5 alkynyl group, C3-C5 alkyl group, a heterocyclic group and aromatic aryl group;

n is an integer of 1 to 5; and dotted line ((-----)) means double bond.

6. The method of claim 5; wherein said R is selected from the group consisting of thiophenyl group, naphtyl group, pyrrolyl group, furyl group and biphenyl group.

7. The method of claim 6; wherein said compound is selected from the group consisting of;
   N-hydroxy-3-(1-naphthalene-2-ylmethyl-2-oxo-2,5-dihydro-1H-pyrrol-3-yl)-propionamide,
   N-hydroxy-3-(1-methyl-2-oxo-2,5-dihydro-1H-pyrrol-3-yl)-propionamide,
   3-(1-allyl-2-oxo-2,5-dihydro-1H-pyrrol-3-yl)-N-hydroxy-propionamide,
   N-hydroxy-3-[1-(2-naphthalene-1-yl-ethyl)-2-oxo-2,5-dihydro-1H-pyrrol-3-yl]-propionamide,
   N-hydroxy-3-[1-(2-naphthalene-2-yl-ethyl)-2-oxo-2,5-dihydro-1H-pyrrol-3-yl]-propionamide,
   N-hydroxy-3-[2-oxo-1-(2-thiophen-2-yl-ethyl)-2,5-dihydro-1H-pyrrol-3-yl]-propionamide,
   3-[1-(3-biphenyl-4-yl-propyl)-2-oxo-2,5-dihydro-1H-pyrrol-3-yl]-N-hydroxy-propionamide, and
   N-hydroxy-3-[1-(3-naphthalene-2-yl-propyl)-2-oxo-2,5-dihydro-1H-pyrrol-3-yl]-propionamide.

8. The method of claim 7; wherein said compound is N-hydroxy-3-[1-(2-naphthalene-2-yl-ethyl)-2-oxo-2,5-dihydro-1H-pyrrol-3-yl]-propionamide.

* * * * *